US012630628B2

(12) United States Patent
Ignatovich et al.

(10) Patent No.: US 12,630,628 B2
(45) Date of Patent: May 19, 2026

(54) ANTI-TIGIT ANTIBODIES AND METHODS OF USE THEREOF

(71) Applicant: AGENUS INC., Lexington, MA (US)

(72) Inventors: Olga Ignatovich, Lexington, MA (US); K. Mark Bushell, Lexington, MA (US); Dhan Sidhartha Chand, Woburn, MA (US); Beth Wensley, Lexington, MA (US)

(73) Assignee: Agenus Inc., Lexington, MA (US)

( * ) Notice: Subject to any disclaimer, the term of this patent is extended or adjusted under 35 U.S.C. 154(b) by 490 days.

(21) Appl. No.: 17/662,042

(22) Filed: May 4, 2022

(65) Prior Publication Data

US 2022/0389095 A1    Dec. 8, 2022

Related U.S. Application Data

(60) Provisional application No. 63/201,536, filed on May 4, 2021.

(51) Int. Cl.
| | |
|---|---|
| *C07K 16/28* | (2006.01) |
| *A61K 31/713* | (2006.01) |
| *A61K 39/00* | (2006.01) |
| *A61K 45/06* | (2006.01) |
| *A61K 47/68* | (2017.01) |
| *C12N 5/10* | (2006.01) |
| *C12N 15/63* | (2006.01) |

(52) U.S. Cl.
CPC ........ *C07K 16/2803* (2013.01); *A61K 31/713* (2013.01); *A61K 39/0011* (2013.01); *A61K 39/001176* (2018.08); *A61K 47/6817* (2017.08); *A61K 47/6849* (2017.08); *C12N 5/10* (2013.01); *C12N 15/63* (2013.01); *A61K 2039/507* (2013.01); *A61K 45/06* (2013.01); *C07K 2317/21* (2013.01); *C07K 2317/565* (2013.01)

(58) Field of Classification Search
CPC ........... C07K 16/2803; C07K 2317/21; C07K 2317/565; C07K 2317/70; C07K 2317/76; C07K 2317/94; A61K 31/713; A61K 39/0011; A61K 39/001176; A61K 47/6817; A61K 47/6849; A61K 45/06; A61K 2039/507; A61K 2039/505; C12N 5/10; C12N 15/63; Y02A 50/30; A61P 35/00; A61P 37/04
See application file for complete search history.

(56) References Cited

U.S. PATENT DOCUMENTS

| | | | | |
|---|---|---|---|---|
| 5,585,089 | A | * 12/1996 | Queen ..................... | C07K 16/00 |
| | | | | 424/143.1 |
| 8,211,431 | B2 | * 7/2012 | Throsby .................. | A61P 43/00 |
| | | | | 424/165.1 |
| 9,499,596 | B2 | 11/2016 | Clark et al. | |
| 9,695,238 | B2 | 7/2017 | Gao et al. | |
| 9,713,641 | B2 | 7/2017 | Hicklin et al. | |
| 9,725,515 | B2 * | 8/2017 | Anderson .............. | G08G 1/042 |
| RE46,534 | E | 9/2017 | Baldwin et al. | |
| 9,873,740 | B2 | 1/2018 | Grogan et al. | |
| 10,017,572 | B2 | 7/2018 | Grogan et al. | |
| 10,112,997 | B2 | 10/2018 | Gurney et al. | |
| 10,124,061 | B2 | 11/2018 | White et al. | |
| 10,144,778 | B2 | 12/2018 | Eisenbach-Schwartz et al. | |
| 10,189,902 | B2 | 1/2019 | Maurer et al. | |
| 10,329,349 | B2 | 6/2019 | Cooper et al. | |
| 10,501,737 | B2 | 12/2019 | Ishii | |
| 10,537,633 | B2 | 1/2020 | Tso et al. | |
| 10,537,637 | B2 | 1/2020 | Sheng et al. | |
| 11,021,537 | B2 | 6/2021 | Chand et al. | |
| 11,680,098 | B2 | 6/2023 | Chand et al. | |
| 2009/0258013 | A1 | 10/2009 | Clark et al. | |
| 2013/0287777 | A1 | 10/2013 | Duffy et al. | |
| 2013/0287797 | A1 | 10/2013 | Heider et al. | |
| 2016/0108123 | A1 | 4/2016 | Freeman et al. | |
| 2016/0152720 | A1 | 6/2016 | Kim et al. | |
| 2016/0193239 | A1 | 7/2016 | Baylin et al. | |
| 2016/0376371 | A1 | 12/2016 | Ravetch et al. | |
| 2017/0037127 | A1 | 2/2017 | Grogan et al. | |
| 2017/0107300 | A1 | 4/2017 | Kuchroo et al. | |
| 2017/0143825 | A1 | 5/2017 | Grogan | |
| 2017/0239338 | A1 | 8/2017 | Szalay et al. | |
| 2017/0260271 | A1 | 9/2017 | Igawa et al. | |
| 2017/0360932 | A1 | 12/2017 | Parry | |
| 2018/0066055 | A1 | 3/2018 | Williams et al. | |
| 2018/0078625 | A1 | 3/2018 | Moon et al. | |
| 2018/0155422 | A1 | 6/2018 | Bhatt et al. | |

(Continued)

FOREIGN PATENT DOCUMENTS

| | | |
|---|---|---|
| EP | 3712170 A1 | 9/2020 |
| WO | WO-2011109789 A2 | 9/2011 |

(Continued)

OTHER PUBLICATIONS

Almagro et. al., Front. Immunol. 2018; 8:1751 (Year: 2018).*
Chiu ML et al. Antibodies 2019 8, 55, 1-80 (Year: 2019).*
Haidar, J.N, et. al. A universal combinatorial design of antibody framework to graft distinct CDR sequences: a bioinformatics approach. Proteins: Structure, function, and bioinformatics, 80(3), pp. 896-912 (Year: 2011).*
PCT International Search Report from PCT/US2022/072110 dated Sep. 12, 2022.

(Continued)

*Primary Examiner* — Gregory S Emch
*Assistant Examiner* — Kathleen Cunningchen
(74) *Attorney, Agent, or Firm* — COOLEY LLP; Andrew T. Wilkins; David M. Lee

(57) ABSTRACT

The instant disclosure provides isolated antibodies that specifically bind to TIGIT (e.g., human TIGIT). Also provided are pharmaceutical compositions comprising these antibodies, nucleic acids encoding these antibodies, expression vectors and host cells for making these antibodies, and methods of treating a subject using these antibodies.

18 Claims, 33 Drawing Sheets
Specification includes a Sequence Listing.

(56) References Cited

U.S. PATENT DOCUMENTS

| | | | |
|---|---|---|---|
| 2018/0169239 A1 | 6/2018 | Grogan | |
| 2018/0185480 A1 | 7/2018 | Mandelboim et al. | |
| 2018/0251548 A1 | 9/2018 | Sabzevari et al. | |
| 2018/0355040 A1 | 12/2018 | Chand et al. | |
| 2018/0371083 A1 | 12/2018 | Williams et al. | |
| 2019/0077869 A1 | 3/2019 | Fiedler et al. | |
| 2020/0040082 A1 | 2/2020 | Piasecki et al. | |
| 2020/0062859 A1 | 2/2020 | Piasecki et al. | |
| 2020/0255516 A1 | 8/2020 | Fu et al. | |
| 2020/0331999 A1 | 10/2020 | Zhang et al. | |
| 2021/0101977 A1 | 4/2021 | Chand et al. | |
| 2022/0089732 A1 | 3/2022 | Chand et al. | |
| 2023/0014036 A1 | 1/2023 | Chand et al. | |
| 2024/0141039 A1 | 5/2024 | Chand et al. | |
| 2024/0141047 A1 | 5/2024 | Chand et al. | |
| 2024/0209082 A1 | 6/2024 | Chand et al. | |

FOREIGN PATENT DOCUMENTS

| | | | |
|---|---|---|---|
| WO | 2013165894 A2 | 11/2013 | |
| WO | WO-2013184912 A2 | 12/2013 | |
| WO | 2015024060 A1 | 2/2015 | |
| WO | WO-2016004875 A1 | 1/2016 | |
| WO | WO-2016011264 A1 | 1/2016 | |
| WO | WO-2016180781 A1 | 11/2016 | |
| WO | WO-2016191643 A2 | 12/2016 | |
| WO | WO-2017023749 A1 | 2/2017 | |
| WO | WO-2017030823 A2 | 2/2017 | |
| WO | 2017053748 A2 | 3/2017 | |
| WO | WO-2017040790 A1 | 3/2017 | |
| WO | WO-2017048824 A1 | 3/2017 | |
| WO | WO-2017059095 A1 | 4/2017 | |
| WO | WO-2017062619 A2 | 4/2017 | |
| WO | WO-2017062820 A1 | 4/2017 | |
| WO | WO-2017123981 A1 | 7/2017 | |
| WO | WO-2017223085 A2 | 12/2017 | |
| WO | WO-2018053242 A1 | 3/2018 | |
| WO | WO-2018102536 A1 | 6/2018 | |
| WO | WO-2018183889 A1 | 10/2018 | |
| WO | WO-2018204363 A1 | 11/2018 | |
| WO | WO-2018204405 A1 | 11/2018 | |
| WO | WO-2018229163 A1 | 12/2018 | |
| WO | WO-2018234793 A2 | 12/2018 | |
| WO | WO-2019062832 A1 | 4/2019 | |
| WO | 2019091449 A1 | 5/2019 | |
| WO | WO-2019129221 A1 | 7/2019 | |
| WO | WO-2019129261 A1 | 7/2019 | |
| WO | WO-2019137548 A1 | 7/2019 | |
| WO | WO-2019152574 A1 | 8/2019 | |
| WO | WO-2019154415 A1 | 8/2019 | |
| WO | WO-2019165434 A1 | 8/2019 | |
| WO | WO-2019168382 A1 | 9/2019 | |
| WO | 2020092554 A1 | 5/2020 | |
| WO | 2020132034 A1 | 6/2020 | |
| WO | 2020185739 A1 | 9/2020 | |
| WO | 2020242919 A1 | 12/2020 | |
| WO | 2020263879 A1 | 12/2020 | |
| WO | 2021042019 A1 | 3/2021 | |

OTHER PUBLICATIONS

U.S. Appl. No. 15/968,094 2018-03555040 U.S. Pat. No. 11,021,537, filed May 1, 2018 Dec. 13, 2018 Jun. 1, 2021, Dhan Sihartha Chand.

U.S. Appl. No. 17/240,944 2022-0089732, filed Apr. 26, 2021 Mar. 24, 2022, Dhan Sidhartha Chand.

Agenus, "Corporate Presentation," Cantor Fitzgerald Global Healthcare Conference. Sep. 2017.

Agenus, "Integrated Immunotherapy: Enabling Best-in-Class I-O Combinations," Non-Confidential Overview. Nov. 2017.

Blake et al., "Molecular Pathways: Targeting CD96 and TIGIT for Cancer Immunotherapy," Clin Cancer Res. Nov. 1, 2016;22(21):5183-5188.

Cattaruzza et al., "Pharmacodynamic biomarkers for anti-TIGIT treatment and prevalence of TIGIT expression in multiple solid tumor types," OncoMed Pharmaceuticals. 2017.

Chauvin et al., "TIGIT and PD-1 impair tumor antigen-specific CD8? T cells in melanoma patients," J Clin Invest. May 2015;125(5):2046-58.

Chew et al., "TIGIT Marks Exhausted T Cells, Correlates with Disease Progression, and Serves as a Target for Immune Restoration in HIV and SIV Infection," PLOS Pathog. Jan. 7, 2016;12(1):e1005349.

Dougall et al., "TIGIT and CD96: new checkpoint receptor targets for cancer immunotherapy," Immunol Rev. Mar. 2017;276(1):112-120.

Gur et al., "Binding of the Fap2 protein of Fusobacterium nucleatum to human inhibitory receptor TIGIT protects tumors from immune cell attack," Immunity. Feb. 17, 2015;42(2):344-355.

He et al., "CD155T/TIGIT Signaling Regulates CD8 + T-cell Metabolism and Promotes Tumor Progression in Human Gastric Cancer," Cancer Res. Nov. 15, 2017;77(22):6375-6388.

Hung et al., "TIGIT and PD-1 dual checkpoint blockade enhances antitumor immunity and survival in GBM," Oncoimmunology. May 24, 2018;7(8):e1466769.

Johnston et al., "The immunoreceptor TIGIT regulates antitumor and antiviral CD8(+) T cell effector function," Cancer Cell. Dec. 8, 2014;26(6):923-937.

Joller et al., "Treg cells expressing the coinhibitory molecule TIGIT selectively inhibit proinflammatory Th1 and Th17 cell responses," Immunity. Apr. 17, 2014;40(4):569-81.

Kurtulus et al., "TIGIT predominantly regulates the immune response via regulatory T cells," J Clin Invest. Nov. 2, 2015;125(11):4053-62.

Lozano et al., "The TIGIT/CD226 axis regulates human T cell function," J Immunol. Apr. 15, 2012;188(8):3869-75.

Manieri et al., "TIGIT: A Key Inhibitor of the Cancer Immunity Cycle," Trends Immunol. Jan. 2017;38(1):20-28.

Meibohm et al., "The role of pharmacokinetics and pharmacodynamics in the development of biotech drugs," Pharmacokinetics and Pharmacodynamics of Biotech Drugs: Principles and Case Studies in Drug Development. Weinheim, Germany: Wiley-VCH (2006): 46-91.

Pauken and Wherry, "TIGIT and CD226: tipping the balance between costimulatory and coinhibitory molecules to augment the cancer immunotherapy toolkit," Cancer Cell. Dec. 8, 2014;26(6):785-787.

PCT International Search Report and Written Opinion from PCT/US2018/030453, dated Jul. 17, 2018.

Samanta et al., "Structural, mutational and biophysical studies reveal a canonical mode of molecular recognition between immune receptor TIGIT and nectin-2," Mol Immunol. Jan. 2017;81:151-159.

Stanietsky et al., "The interaction of TIGIT with PVR and PVRL2 inhibits human NK cell cytotoxicity," Proc Natl Acad Sci U S A. Oct. 20, 2009;106(42):17858-63.

Stein, "Next generation immunomodulatory antibodies: optimizing therapeutic impact," 2017.

Stengel et al., "Structure of TIGIT immunoreceptor bound to poliovirus receptor reveals a cell-cell adhesion and signaling mechanism that requires cis-trans receptor clustering," Proc Natl Acad Sci USA. Apr. 3, 2012;109(14):5399-404.

White et al., "Antibody-targeted immunotherapy for treatment of malignancy," Annu Rev Med. 2001; 52: 125-45.

Yu et al., "The surface protein TIGIT suppresses T cell activation by promoting the generation of mature immunoregulatory dendritic cells," Nat Immunol. Jan. 2009;10(1):48-57.

Zhou et al., "Intrinsic Expression of Immune Checkpoint Molecule TIGIT Could Help Tumor Growth in vivo by Suppressing the Function of NK and CD8 + T Cells," Front Immunol. Nov. 29, 2018;9:2821.

Lazar et al., "Engineered antibody Fc variants with enhanced effector function" Proc. Natl. Acad. Sci. USA., 2016. 103(11); pp. 4005-4010.

Ha et al., Immunoglobulin Fc Heterodimer Platform Technology: From Design to Application in Therapeutic Antibodies and Proteins Fron. Immunol. 2016. 7(349); 16 pages.

(56)  References Cited

OTHER PUBLICATIONS

Aguilera et al., "CD96 targeted antibodies need not block CD96-CD155 interactions to promote NK cell anti-metastatic activity", Oncoimmunology, 2018, 7(5):e1424677, pp. e1424677-1-e1424677-10.

Gorvel et al., "Targeting the "PVR-TIGIT axis" with immune checkpoint therapies", F1000Research, 2020, 9(F1000 Faculty Rev):354, pp. 1-10.

Oganesyan et al., "Structural characterization of a mutated, ADCC-enhanced human Fc fragment", Molecular Immunology, 2008, 45(7):1872-1882.

Spasevska et al., "Advances in Bispecific Antibodies Engineering: Novel Concepts for Immunotherapies", Journal of Blood Disorders and Transfusion, 2015, 6(1):1000243, pp. 1-8.

Ward et al., "Abstract 253: Anti-TIGIT Antibodies Require Enhanced FcGammaR Co-Engagement for Optimal T and NK Cell-Dependent Anti-Tumor Immunity", Journal of Immunotherapy and Cancer, 2020, 8(Suppl 3):A153.

International Preliminary Report on Patentability received for PCT Application No. PCT/US2018/030453, completed on Jul. 31, 2019, 14 pages.

International Preliminary Report on Patentability received for PCT Application No. PCT/US2022/072099, mailed on Nov. 16, 2023, 15 pages.

International Preliminary Report on Patentability received for PCT Application No. PCT/US2022/072110, mailed on Nov. 16, 2023, 8 pages.

International Search Report and Written Opinion received for PCT Application No. PCT/US2020/048700, mailed on Dec. 8, 2020, 20 pages.

International Search Report and Written Opinion received for PCT Application No. PCT/US2022/072099, mailed on Oct. 6, 2022, 23 pages.

Mittal et al., "CD96 Is an Immune Checkpoint That Regulates CD8+ T-cell Antitumor Function Free", Cancer Immunology Research, Apr. 2019, 7(4):559-571.

* cited by examiner

Elution time in cation exchange chromatography

BA159

Reference antibody

Thermal melt: unfolding

BA159

Reference antibody

Thermal melt: aggregation

BA159

Reference antibody

FcRn affinity chromatography

FcRn affinity chromatography

Elution time in cation exchange chromatography

Thermal melt: unfolding

BA159

BA160

Thermal melt: aggregation

BA159

BA160

Elution time in cation exchange chromatography

Elution time in cation exchange chromatography

Average hydrodynamic diameter

Average hydrodynamic diameter

Reference antibody

Interchain disulphide bonding under stress conditions

Interchain disulphide bonding under stress conditions

Interchain disulphide bonding under stress conditions

Clipping under various conditions

Clipping under various conditions

Elution time under stress conditions in size exclusion chromatography

Elution time under stress conditions in size exclusion chromatography

BA159 5x Freeze-thaw

Elution time under stress conditions in size exclusion chromatography

Elution time under stress conditions in size exclusion chromatography

Elution time under stress conditions in size exclusion chromatography

Elution time under stress conditions in size exclusion chromatography

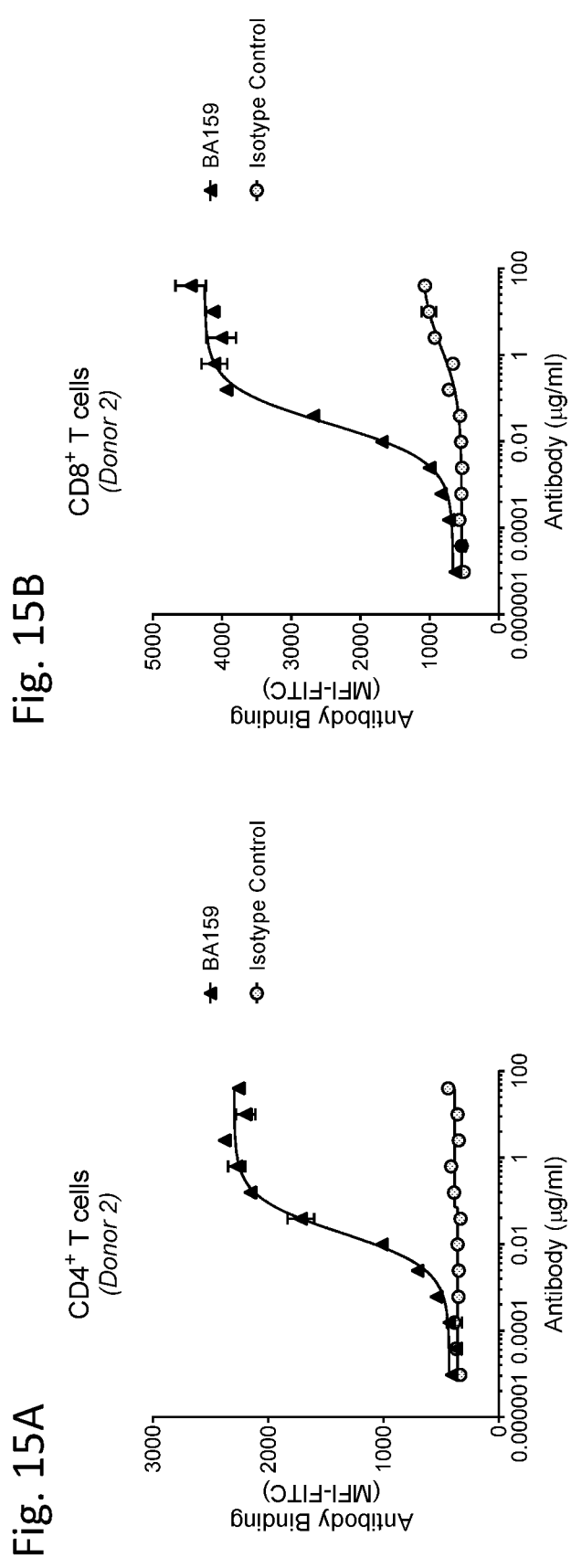
Binding profiles to activated human CD4+ and CD8+ T cells

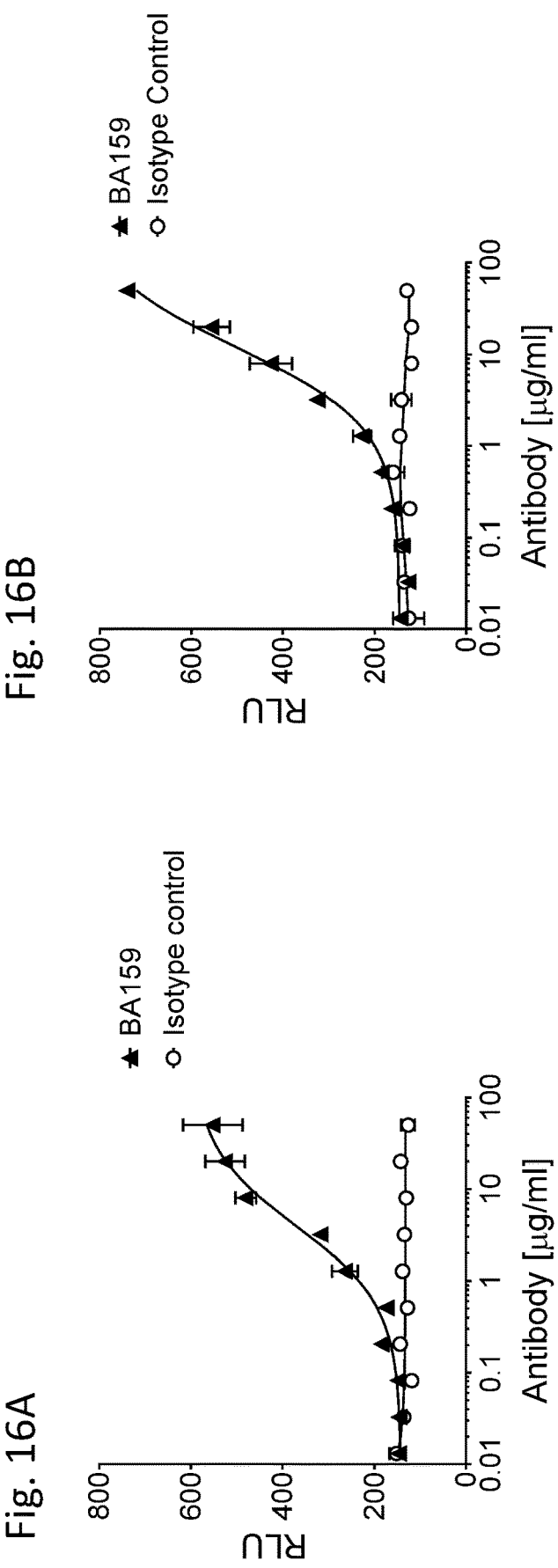
Reporter Assay: TIGIT/PVR cell-based reporter blocking assay

Reporter Assay: TIGIT/PVR cell-based reporter blocking assay

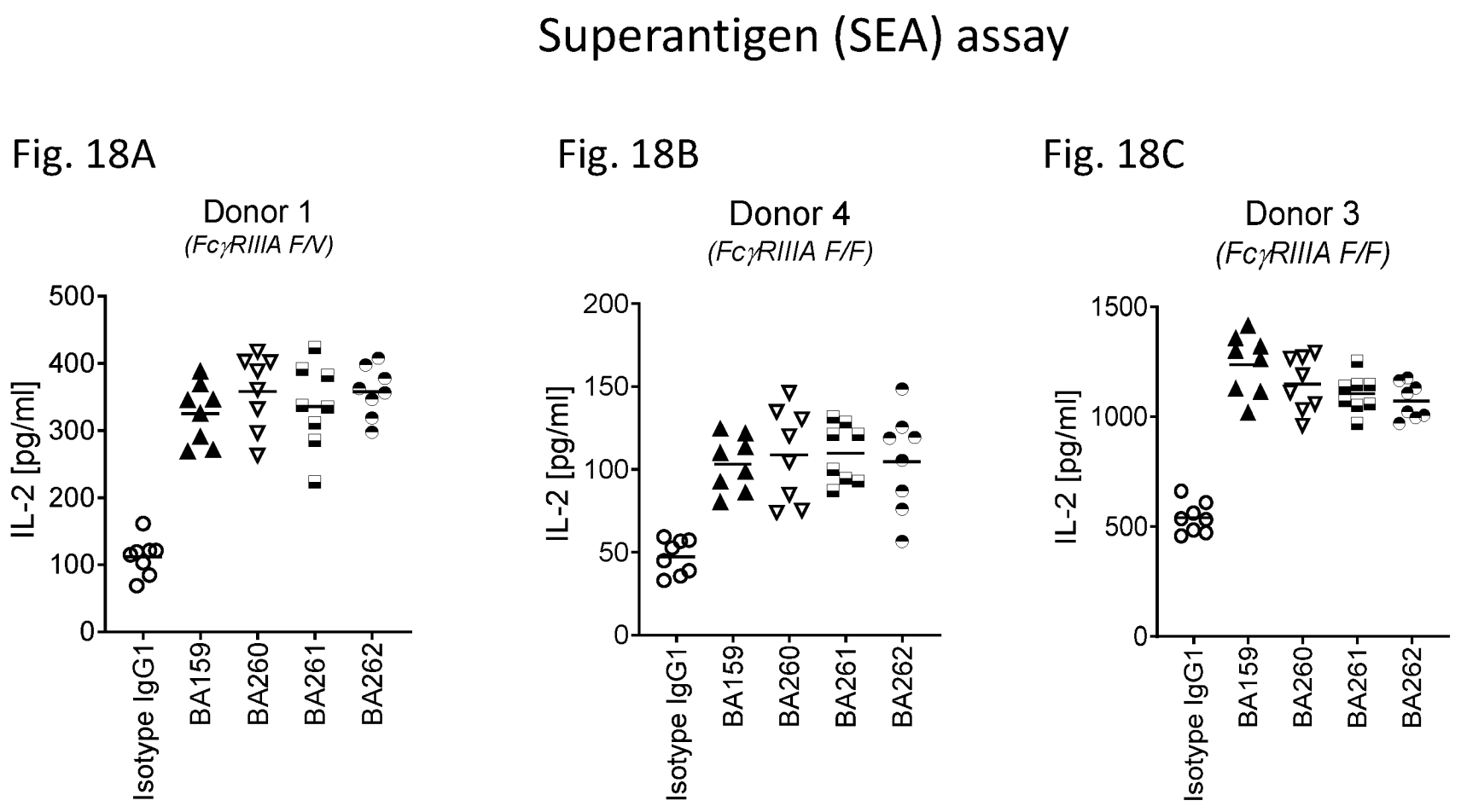

Superantigen (SEA) assay

Fig. 18A

Donor 1
(FcγRIIIA F/V)

IL-2 [pg/ml]

Isotype IgG1    BA159    BA260    BA261    BA262

Fig. 18B

Donor 4
(FcγRIIIA F/F)

IL-2 [pg/ml]

Isotype IgG1    BA159    BA260    BA261    BA262

Fig. 18C

Donor 3
(FcγRIIIA F/F)

IL-2 [pg/ml]

Isotype IgG1    BA159    BA260    BA261    BA262

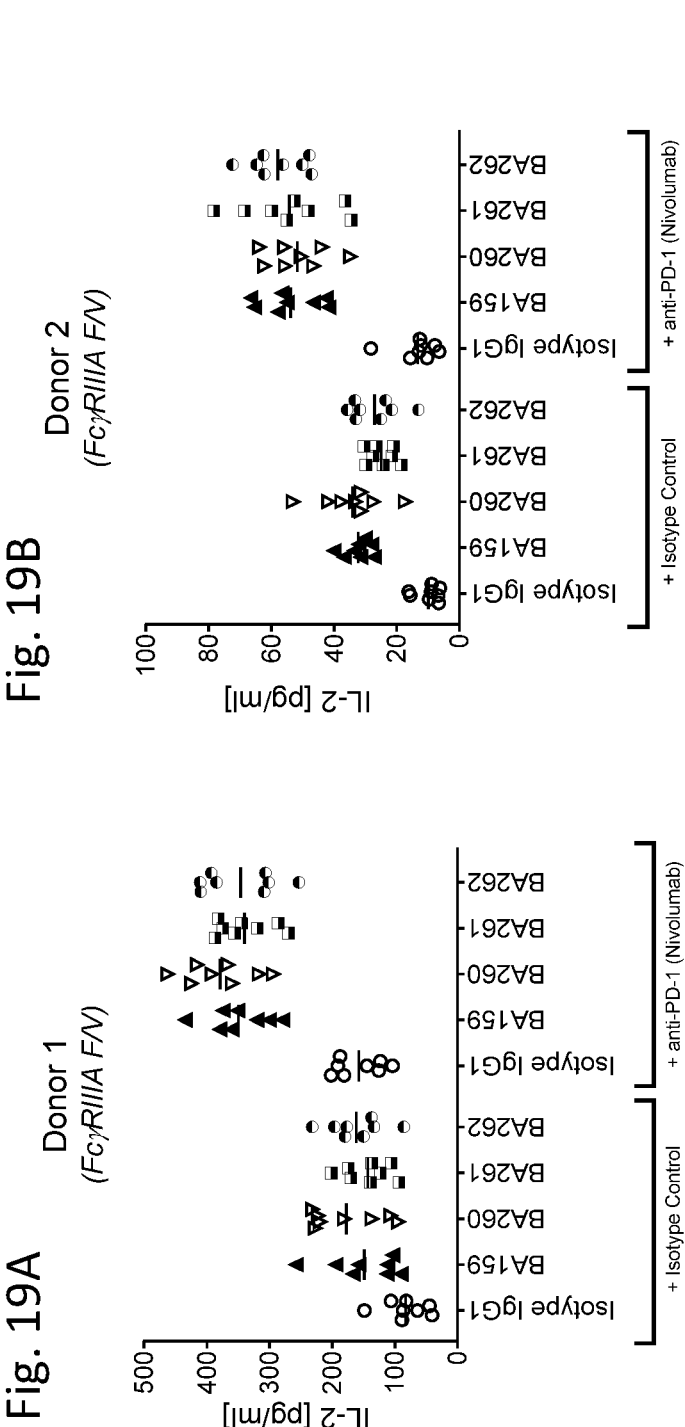
Superantigen (SEA) assay – combination with anti-PD-1

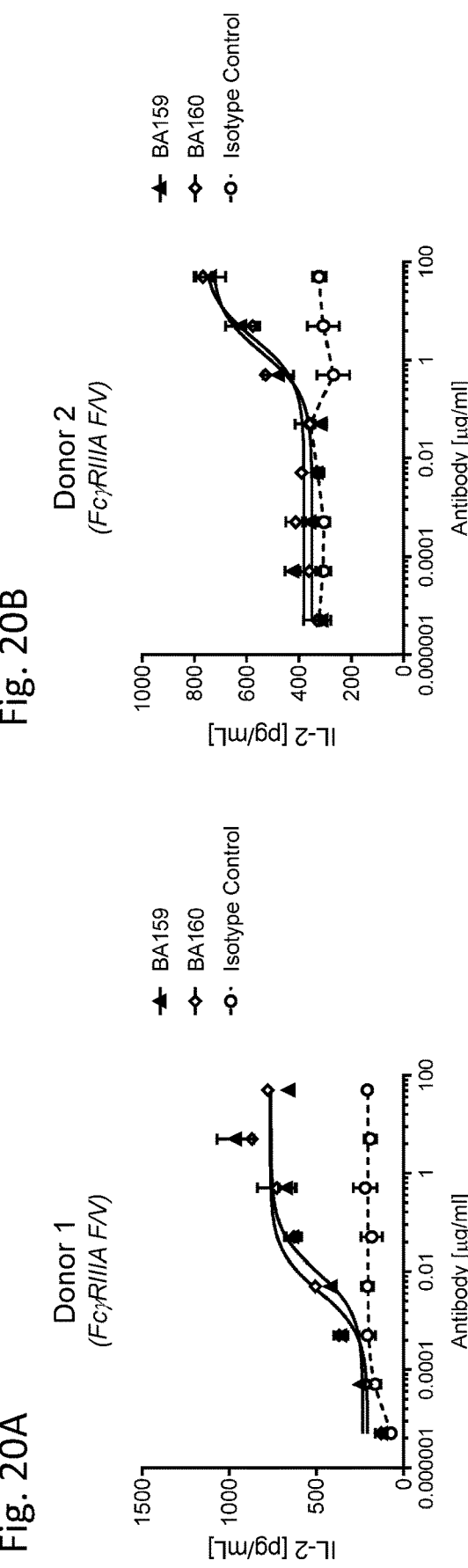
Superantigen (SEA) assay

SEQUENCE LISTING

```
<160> NUMBER OF SEQ ID NOS: 24

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Ser Tyr Gly Ile Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide
```

<400> SEQUENCE: 2

Gly Ile Thr Pro Phe Phe Asn Arg Val Asp Val Ala Glu Lys Phe Gln
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Synthetic peptide

<400> SEQUENCE: 3

Asp Leu Arg Arg Gly Gly Val Gly Asp Ala Phe Asp Ile
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide

<400> SEQUENCE: 4

Thr Gly Thr Ser Ser Asp Val Gly Ser His Asn Tyr Val Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Glu Val Ser Tyr Arg Pro Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Ser Ser Tyr Thr Pro Ser Ser Ala Thr Val
1               5                   10

<210> SEQ ID NO 7
<211> LENGTH: 122
<212> TYPE: PRT
<213> ORGANISM: Artificial Sequence
<220> FEATURE:
<223> OTHER INFORMATION: Synthetic peptide

<400> SEQUENCE: 7

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ala Ser Tyr
            20                  25                  30

Gly Ile Ser Trp Val Arg Gln Ala Pro Gly Gln Gly Leu Glu Trp Met
        35                  40                  45

```
Gly Gly Ile Thr Pro Phe Phe Asn Arg Val Asp Val Ala Glu Lys Phe
    50                  55                  60

Gln Gly Arg Val Thr Ile Thr Ala Asp Lys Ser Thr Ser Thr Ala Tyr
65                  70                  75                  80

Ile Glu Leu Ser Ser Leu Arg Ser Glu Asp Thr Ala Val Tyr Tyr Cys
                85                  90                  95

Ala Arg Asp Leu Arg Arg Gly Gly Val Gly Asp Ala Phe Asp Ile Trp
                100                 105                 110

Gly Arg Gly Thr Leu Val Thr Val Ser Ser
        115                 120
```

<210> SEQ ID NO 8
<211> LENGTH: 122
<212> TYPE: PRT
<213> ORGANISM: Artificial Sequence
<220> FEATURE:
<223> OTHER INFORMATION: Synthetic peptide

<400> SEQUENCE: 8

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ala Ser Tyr
                20                  25                  30

Gly Ile Ser Trp Val Arg Gln Ala Pro Gly Gln Gly Leu Glu Trp Met
        35                  40                  45

Gly Gly Ile Thr Pro Phe Phe Asn Arg Val Asp Val Ala Glu Lys Phe
    50                  55                  60

Gln Gly Arg Val Thr Ile Thr Ala Asp Thr Ser Thr Asn Thr Val Tyr
65                  70                  75                  80

Ile Glu Leu Ser Ser Leu Arg Ser Glu Asp Thr Ala Val Tyr Tyr Cys
                85                  90                  95

Ala Arg Asp Leu Arg Arg Gly Gly Val Gly Asp Ala Phe Asp Ile Trp
                100                 105                 110

Gly Arg Gly Thr Leu Val Thr Val Ser Ser
        115                 120
```

<210> SEQ ID NO 9
<211> LENGTH: 110
<212> TYPE: PRT
<213> ORGANISM: Artificial Sequence
<220> FEATURE:
<223> OTHER INFORMATION: Synthetic peptide

<400> SEQUENCE: 9

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser His
                20                  25                  30

Asn Tyr Val Ser Trp Tyr Gln Gln His Pro Gly Lys Ala Pro Lys Leu
        35                  40                  45

Met Ile Tyr Glu Val Ser Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Pro Ser
                85                  90                  95

Ser Ala Thr Val Phe Gly Ala Gly Thr Lys Leu Thr Val Leu
                100                 105                 110
```

```
<210> SEQ ID NO 10
<211> LENGTH: 110
<212> TYPE: PRT
<213> ORGANISM: Artificial Sequence
<220> FEATURE:
<223> OTHER INFORMATION: Synthetic peptide

<400> SEQUENCE: 10

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser His
            20                  25                  30

Asn Tyr Val Ser Trp Tyr Gln Gln His Pro Gly Lys Ala Pro Lys Leu
        35                  40                  45

Met Ile Tyr Glu Val Ser Tyr Arg Pro Ser Glu Ile Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Pro Ser
                85                  90                  95

Ser Ala Thr Val Phe Gly Ala Gly Thr Lys Leu Thr Val Leu
            100                 105                 110

<210> SEQ ID NO 11
<211> LENGTH: 452
<212> TYPE: PRT
<213> ORGANISM: Artificial Sequence
<220> FEATURE:
<223> OTHER INFORMATION: Synthetic peptide

<400> SEQUENCE: 11

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ala Ser Tyr
            20                  25                  30

Gly Ile Ser Trp Val Arg Gln Ala Pro Gly Gln Gly Leu Glu Trp Met
        35                  40                  45

Gly Gly Ile Thr Pro Phe Phe Asn Arg Val Asp Val Ala Glu Lys Phe
    50                  55                  60

Gln Gly Arg Val Thr Ile Thr Ala Asp Lys Ser Thr Ser Thr Ala Tyr
65                  70                  75                  80

Ile Glu Leu Ser Ser Leu Arg Ser Glu Asp Thr Ala Val Tyr Tyr Cys
                85                  90                  95

Ala Arg Asp Leu Arg Arg Gly Gly Val Gly Asp Ala Phe Asp Ile Trp
            100                 105                 110

Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

-continued

```
Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Asp Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Leu Pro
            325                 330                 335

Glu Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
        435                 440                 445

Ser Pro Gly Lys
    450
```

```
<210> SEQ ID NO 12
<211> LENGTH: 452
<212> TYPE: PRT
<213> ORGANISM: Artificial Sequence
<220> FEATURE:
<223> OTHER INFORMATION: Synthetic peptide

<400> SEQUENCE: 12

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ala Ser Tyr
            20                  25                  30

Gly Ile Ser Trp Val Arg Gln Ala Pro Gly Gln Gly Leu Glu Trp Met
        35                  40                  45

Gly Gly Ile Thr Pro Phe Phe Asn Arg Val Asp Val Ala Glu Lys Phe
    50                  55                  60

Gln Gly Arg Val Thr Ile Thr Ala Asp Thr Ser Thr Asn Thr Val Tyr
65                  70                  75                  80

Ile Glu Leu Ser Ser Leu Arg Ser Glu Asp Thr Ala Val Tyr Tyr Cys
            85                  90                  95
```

```
Ala Arg Asp Leu Arg Arg Gly Gly Val Gly Asp Ala Phe Asp Ile Trp
        100                 105                 110

Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Asp Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Leu Pro
                325                 330                 335

Glu Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 13
<211> LENGTH: 216
<212> TYPE: PRT
<213> ORGANISM: Artificial Sequence
<220> FEATURE:
<223> OTHER INFORMATION: Synthetic peptide -continued

<400> SEQUENCE: 13

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser His
                20                  25                  30

Asn Tyr Val Ser Trp Tyr Gln Gln His Pro Gly Lys Ala Pro Lys Leu
            35                  40                  45

Met Ile Tyr Glu Val Ser Tyr Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Pro Ser
                85                  90                  95

Ser Ala Thr Val Phe Gly Ala Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

```
<210> SEQ ID NO 14
<211> LENGTH: 215
<212> TYPE: PRT
<213> ORGANISM: Artificial Sequence
<220> FEATURE:
<223> OTHER INFORMATION: Synthetic peptide
```

<400> SEQUENCE: 14

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser His
                20                  25                  30

Asn Tyr Val Ser Trp Tyr Gln Gln His Pro Gly Lys Ala Pro Lys Leu
            35                  40                  45

Met Ile Tyr Glu Val Ser Tyr Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Pro Ser
                85                  90                  95

Ser Ala Thr Val Phe Gly Ala Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125
```

-continued

```
Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Thr Glu Cys
    210                 215

<210> SEQ ID NO 15
<211> LENGTH: 216
<212> TYPE: PRT
<213> ORGANISM: Artificial Sequence
<220> FEATURE:
<223> OTHER INFORMATION: Synthetic peptide

<400> SEQUENCE: 15

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser His
                20                  25                  30

Asn Tyr Val Ser Trp Tyr Gln Gln His Pro Gly Lys Ala Pro Lys Leu
                35                  40                  45

Met Ile Tyr Glu Val Ser Tyr Arg Pro Ser Glu Ile Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Pro Ser
                85                  90                  95

Ser Ala Thr Val Phe Gly Ala Gly Thr Lys Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Thr Glu Cys Ser
    210                 215

<210> SEQ ID NO 16
<211> LENGTH: 330
<212> TYPE: PRT
<213> ORGANISM: Artificial Sequence
<220> FEATURE:
<223> OTHER INFORMATION: Synthetic peptide
```

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 17
<211> LENGTH: 106
<212> TYPE: PRT
<213> ORGANISM: Artificial Sequence
<220> FEATURE:
<223> OTHER INFORMATION: Synthetic peptide

<400> SEQUENCE: 17

Gly Gln Pro Lys Ala Ala Pro Ser Val Thr Leu Phe Pro Pro Ser Ser
1               5                   10                  15

-continued

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 18
<211> LENGTH: 105
<212> TYPE: PRT
<213> ORGANISM: Artificial Sequence
<220> FEATURE:
<223> OTHER INFORMATION: Synthetic peptide

<400> SEQUENCE: 18

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys
            100                 105

<210> SEQ ID NO 19
<211> LENGTH: 451
<212> TYPE: PRT
<213> ORGANISM: Artificial Sequence
<220> FEATURE:
<223> OTHER INFORMATION: Synthetic peptide

<400> SEQUENCE: 19

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ala Ser Tyr
            20                  25                  30

Gly Ile Ser Trp Val Arg Gln Ala Pro Gly Gln Gly Leu Glu Trp Met
            35                  40                  45

Gly Gly Ile Thr Pro Phe Phe Asn Arg Val Asp Val Ala Glu Lys Phe
    50                  55                  60

Gln Gly Arg Val Thr Ile Thr Ala Asp Lys Ser Thr Ser Thr Ala Tyr
65                  70                  75                  80

Ile Glu Leu Ser Ser Leu Arg Ser Glu Asp Thr Ala Val Tyr Tyr Cys
                85                  90                  95

Ala Arg Asp Leu Arg Arg Gly Gly Val Gly Asp Ala Phe Asp Ile Trp
            100                 105                 110

-continued

```
Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Asp Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Leu Pro
                325                 330                 335

Glu Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
    435                 440                 445

Ser Pro Gly
    450
```

```
<210> SEQ ID NO 20
<211> LENGTH: 451
<212> TYPE: PRT
<213> ORGANISM: Artificial Sequence
<220> FEATURE:
<223> OTHER INFORMATION: Synthetic peptide

<400> SEQUENCE: 20
```

```
Glu Val Gln Leu Val Gln Ser Gly Ala Glu Val Lys Lys Pro Gly Ser
1               5                   10                  15
```

-continued

```
Ser Val Lys Val Ser Cys Lys Ala Ser Gly Tyr Thr Phe Ala Ser Tyr
        20                  25                  30

Gly Ile Ser Trp Val Arg Gln Ala Pro Gly Gln Gly Leu Glu Trp Met
        35                  40                  45

Gly Gly Ile Thr Pro Phe Phe Asn Arg Val Asp Val Ala Glu Lys Phe
    50                  55                  60

Gln Gly Arg Val Thr Ile Thr Ala Asp Thr Ser Thr Asn Thr Val Tyr
65                  70                  75                  80

Ile Glu Leu Ser Ser Leu Arg Ser Glu Asp Thr Ala Val Tyr Tyr Cys
                85                  90                  95

Ala Arg Asp Leu Arg Arg Gly Gly Val Gly Asp Ala Phe Asp Ile Trp
            100                 105                 110

Gly Arg Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Asp Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Leu Pro
                325                 330                 335

Glu Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430
```

-continued

```
Met His Glu Ala Leu His Asn His Tyr Thr Gln Lys Ser Leu Ser Leu
        435                 440                 445

Ser Pro Gly
    450

<210> SEQ ID NO 21
<211> LENGTH: 215
<212> TYPE: PRT
<213> ORGANISM: Artificial Sequence
<220> FEATURE:
<223> OTHER INFORMATION: Synthetic peptide

<400> SEQUENCE: 21

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser His
            20                  25                  30

Asn Tyr Val Ser Trp Tyr Gln Gln His Pro Gly Lys Ala Pro Lys Leu
        35                  40                  45

Met Ile Tyr Glu Val Ser Tyr Arg Pro Ser Glu Ile Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Pro Ser
                85                  90                  95

Ser Ala Thr Val Phe Gly Ala Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215

<210> SEQ ID NO 22
<211> LENGTH: 329
<212> TYPE: PRT
<213> ORGANISM: Artificial Sequence
<220> FEATURE:
<223> OTHER INFORMATION: Synthetic peptide

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

-continued

```
Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Arg Val Glu Pro Lys Ser Cys Asp Lys Thr His Thr Cys Pro Pro Cys
            100             105             110

Pro Ala Pro Glu Leu Leu Gly Gly Pro Asp Val Phe Leu Phe Pro Pro
            115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
                180             185             190

His Gln Asp Trp Leu Asn Gly Lys Glu Tyr Lys Cys Lys Val Ser Asn
            195             200             205

Lys Ala Leu Pro Leu Pro Glu Glu Lys Thr Ile Ser Lys Ala Lys Gly
    210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
                245             250             255

Pro Ser Asp Ile Ala Val Glu Trp Glu Ser Asn Gly Gln Pro Glu Asn
                260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Ser Leu Ser Leu Ser Pro Gly
                325
```

```
<210> SEQ ID NO 23
<211> LENGTH: 118
<212> TYPE: PRT
<213> ORGANISM: Homo sapiens

<400> SEQUENCE: 23
```

```
Met Met Thr Gly Thr Ile Glu Thr Thr Gly Asn Ile Ser Ala Glu Lys
1               5               10              15

Gly Gly Ser Ile Ile Leu Gln Cys His Leu Ser Ser Thr Thr Ala Gln
                20              25              30

Val Thr Gln Val Asn Trp Glu Gln Gln Asp Gln Leu Leu Ala Ile Cys
            35              40              45

Asn Ala Asp Leu Gly Trp His Ile Ser Pro Ser Phe Lys Asp Arg Val
    50              55              60

Ala Pro Gly Pro Gly Leu Gly Leu Thr Leu Gln Ser Leu Thr Val Asn
65              70              75              80

Asp Thr Gly Glu Tyr Phe Cys Ile Tyr His Thr Tyr Pro Asp Gly Thr
                85              90              95
```

-continued

```
Tyr Thr Gly Arg Ile Phe Leu Glu Val Leu Glu Ser Ser Val Ala Glu
            100                 105                 110

His Gly Ala Arg Phe Gln
        115

<210> SEQ ID NO 24
<211> LENGTH: 119
<212> TYPE: PRT
<213> ORGANISM: Macaca fascicularis

<400> SEQUENCE: 24

Met Met Thr Gly Thr Ile Glu Thr Thr Gly Asn Ile Ser Ala Lys Lys
1               5                   10                  15

Gly Gly Ser Val Ile Leu Gln Cys His Leu Ser Ser Thr Met Ala Gln
            20                  25                  30

Val Thr Gln Val Asn Trp Glu Gln His Asp His Ser Leu Leu Ala Ile
        35                  40                  45

Arg Asn Ala Glu Leu Gly Trp His Ile Tyr Pro Ala Phe Lys Asp Arg
    50                  55                  60

Val Ala Pro Gly Pro Gly Leu Gly Leu Thr Leu Gln Ser Leu Thr Met
65                  70                  75                  80

Asn Asp Thr Gly Glu Tyr Phe Cys Thr Tyr His Thr Tyr Pro Asp Gly
            85                  90                  95

Thr Tyr Arg Gly Arg Ile Phe Leu Glu Val Leu Glu Ser Ser Val Ala
            100                 105                 110

Glu His Ser Ala Arg Phe Gln
        115
```

ANTI-TIGIT ANTIBODIES AND METHODS OF USE THEREOF

1. RELATED APPLICATION

This application benefits priority to U.S. Provisional Application No. 63/201,536, filed on May 4, 2021, the entirety of which is herein incorporated by reference.

2. SEQUENCE LISTING

The contents of the electronically submitted sequence listing in ASCII text file (Name: 190517_SL; Size 39,552 bytes; Date of Creation: Apr. 28, 2022) is herein incorporated by reference in its entirety.

3. FIELD

The instant disclosure relates to anti-TIGIT antibodies and methods of using the same.

4. BACKGROUND

The protein T-cell immunoreceptor with Ig and ITIM domains (TIGIT), also known as VSIG9 or VSTM3, is a type I transmembrane protein in the immunoglobulin (Ig) superfamily. It has a single Ig domain, a type I transmembrane domain, a single intracellular immunoreceptor tyrosine-based inhibitory motif (ITIM), and a single immunoglobulin tail tyrosine (ITT)-like phosphorylation motif and is expressed on activated CD4-positive/CD25-positive regulatory T cells (Tregs), memory CD45RO-positive T cells, and natural killer (NK) cells, but not naïve T cells.

CD155 (also known as poliovirus receptor (PVR)) is highly expressed on monocytes and dendritic cells, and is capable of activating effector T cells and NK cells, as well as attenuating the activity of Tregs, through binding to its two receptors CD226 and CD96. TIGIT binds to CD155 and has been shown to antagonize the interaction of CD155 with CD226 and CD96, thereby suppressing T cell- and NK cell-mediated immune activity.

Given the role of human TIGIT in modulating immune responses, therapeutic agents designed to block TIGIT ligand interactions hold great promise for the treatment of diseases that involve immune suppression.

5. SUMMARY

The instant disclosure provides antibodies that specifically bind to TIGIT (e.g., human TIGIT). Also provided are pharmaceutical compositions comprising these antibodies, nucleic acids encoding these antibodies, expression vectors and host cells for making these antibodies, and methods of treating a subject using these antibodies.

In one aspect, the instant disclosure provides an isolated antibody that specifically binds to human TIGIT, the antibody comprising:

(a) a VH comprising the CDRH1, CDRH2, and CDRH3 amino acid sequences of the VH amino acid sequence of SEQ ID NO: 7; and/or (b) a VL comprising the CDRL1, CDRL2, and CDRL3 amino acid sequences of the VL amino acid sequence of SEQ ID NO: 9, wherein the VH comprises lysine at amino acid position 12, serine at amino acid position 16, lysine at amino acid position 73, serine at amino acid position 76, alanine at amino acid position 78, and/or arginine at amino acid positions 83, respectively, and wherein the VL comprises lysine at amino acid position 45, glycine at amino acid position 57, valine at amino acid position 58, and/or alanine at amino acid positions 80, in each case numbered according to Kabat.

In certain embodiments:

(a) the VH comprises lysine, serine, lysine, serine, alanine, and arginine at amino acid positions 12, 16, 73, 76, 78, and 83, respectively, and the VL comprises lysine, glycine, valine, and alanine at amino acid positions 45, 57, 58, and 80, respectively;

(b) the VH comprises lysine, serine, and arginine at amino acid positions 12, 16, and 83, respectively, and the VL comprises lysine and alanine at amino acid positions 45 and 80, respectively;

(c) the VH comprises lysine, serine, lysine, serine, alanine, and arginine at amino acid positions 12, 16, 73, 76, 78, and 83, respectively, and the VL comprises lysine and alanine at amino acid positions 45 and 80, respectively; or (d) the VH comprises lysine, serine, and arginine at amino acid positions 12, 16, and 83, respectively, and the VL comprises lysine, glycine, valine, and alanine at amino acid positions 45, 57, 58, and 80, respectively, numbered according to Kabat.

In certain embodiments, the antibody comprises the CDRH1, CDRH2, CDRH3, CDRL1, CDRL2, and CDRL3 amino acid sequences of SEQ ID NOs: 1, 2, 3, 4, 5, and 6, respectively.

In certain embodiments, the antibody comprises the VH amino acid sequence of SEQ ID NO: 7 or 8. In another embodiment, the amino acid sequence of the VH consists of the amino acid sequence of SEQ ID NO: 7 or 8. In another embodiment, the antibody comprises the VL amino acid sequence of SEQ ID NO: 9 or 10. In another embodiment, the VL consists of the amino acid sequence of SEQ ID NO: 9 or 10.

In another aspect, the instant disclosure provides an isolated antibody that specifically binds to human TIGIT, the antibody comprising a VH comprising the amino acid sequence of SEQ ID NO: 7 or 8, and/or a VL comprising the amino acid sequence of SEQ ID NO: 9 or 10. In certain embodiments, the amino acid sequence of the VH consists of the amino acid sequence of SEQ ID NO: 7 or 8, and/or the amino acid sequence of the VL consists of the amino acid sequence of SEQ ID NO: 9 or 10. In another embodiment, the antibody comprises the VH and VL amino acid sequences of SEQ ID NOs: 7 and 9; 7 and 10; 8 and 9; or 8 and 10, respectively. In another embodiment, the amino acid sequences of the VH and VL consist of the amino acid sequences of SEQ ID NOs: 7 and 9; 7 and 10; 8 and 9; or 8 and 10, respectively.

In certain embodiments, the antibody comprises a heavy chain constant region selected from the group consisting of human $IgG_1$, $IgG_2$, $IgG_3$, $IgG_4$, $IgA_1$, and $IgA_2$. In another embodiment, the antibody comprises an $IgG_1$ heavy chain constant region. In another embodiment, the antibody comprises a heavy chain constant region comprising the amino acid sequence of SEQ ID NO: 16 or 22. In another embodiment, the amino acid sequence of the $IgG_1$ heavy chain constant region comprises an N297A mutation, numbered according to the EU numbering system.

In certain embodiments, the antibody comprises a heavy chain constant region that is a variant of a wild type heavy chain constant region, wherein the variant heavy chain constant region binds to an FcγR with higher affinity than the wild type heavy chain constant region binds to the FcγR. In another embodiment, the FcγR is FcγRIIB or FcγRIIIA In certain embodiments, the amino acid sequence of the IgG₁ heavy chain constant region comprises S267E and L328F mutations, numbered according to the EU numbering system. In another embodiment, the amino acid sequence of the IgG₁ heavy chain constant region comprises at least one mutation selected from the group consisting of S239D, A330L, and I332E mutations, numbered according to the EU numbering system. In another embodiment, the amino acid sequence of the IgG₁ heavy chain constant region comprises S239D, A330L, and I332E mutations, numbered according to the EU numbering system.

In certain embodiments, the antibody comprises a heavy chain comprising the amino acid sequence of SEQ ID NO: 11, 12, 19, or 20. In another embodiment, the heavy chain consists of the amino acid sequence of SEQ ID NO: 11, 12, 19, or 20. In another embodiment, the antibody comprises a light chain constant region comprising the amino acid sequence of SEQ ID NO: 17 or 18. In another embodiment, the antibody comprises a light chain comprising the amino acid sequence of SEQ ID NO: 13, 14, 15, or 21. In another embodiment, the light chain consists of the amino acid sequence of SEQ ID NO: 13, 14, 15, or 21.

In another aspect, the instant disclosure provides an isolated antibody that specifically binds to human TIGIT, wherein the antibody comprises a heavy chain comprising the amino acid sequence of SEQ ID NO: 11, 12, 19, or 20, and/or a light chain comprising the amino acid sequence of SEQ ID NO: 13, 14, 15, or 21.

In certain embodiments, the amino acid sequence of the heavy chain consists of the amino acid sequence of SEQ ID NO: 11, 12, 19, or 20, and/or the amino acid sequence of the light chain consists of the amino acid sequence of SEQ ID NO: 13, 14, 15, or 21. In another embodiment, the heavy chain and light chain comprise the amino acid sequences of SEQ ID NOs: 11 and 13; 11 and 14; 11 and 15; 11 and 21; 12 and 13; 12 and 14; 12 and 15; 12 and 21; 19 and 13; 19 and 14; 19 and 15; 19 and 21; 20 and 13; 20 and 14; 20 and 15; or 20 and 21, respectively. In another embodiment, the heavy chain and the light chain consist of the amino acid sequences of SEQ ID NOs: 11 and 13; 11 and 14; 11 and 15; 11 and 21; 12 and 13; 12 and 14; 12 and 15; 12 and 21; 19 and 13; 19 and 14; 19 and 15; 19 and 21; 20 and 13; 20 and 14; 20 and 15; or 20 and 21, respectively.

In certain embodiments, the antibody is multispecific. In another embodiment, the isolated antibody is conjugated to a cytotoxic agent, cytostatic agent, toxin, radionuclide, or detectable label. In another embodiment, the isolated antibody is conjugated to an antibody.

In another aspect, the instant disclosure provides an isolated polynucleotide encoding the VH and/or the VL, or a heavy chain and/or a light chain, of an isolated antibody disclosed herein.

In another aspect, the instant disclosure provides a vector comprising a polynucleotide disclosed herein.

In another aspect, the instant disclosure provides a recombinant host cell comprising:
(a) a polynucleotide disclosed herein;
(b) a vector disclosed herein;
(c) a polynucleotide encoding the VH and the VL, or a heavy chain and a light chain, of an isolated antibody disclosed herein;
(d) a vector comprising a polynucleotide encoding the VH and the VL, or a heavy chain and a light chain, of an isolated antibody disclosed herein;

(e) a first polynucleotide encoding the VH or a heavy chain of an isolated antibody disclosed herein, and a second polynucleotide encoding the VL or a light chain of an isolated antibody disclosed herein; or
(f) a first vector comprising a first polynucleotide encoding the VH or a heavy chain of an isolated antibody disclosed herein, and a second vector comprising a second polynucleotide encoding the VL or a light chain of an isolated antibody disclosed herein.

In another aspect, the instant disclosure provides a pharmaceutical composition comprising an isolated antibody disclosed herein, a polynucleotide disclosed herein, a vector disclosed herein, or a host cell disclosed herein, and a pharmaceutically acceptable carrier or excipient.

In another aspect, the instant disclosure provides a method of producing an isolated antibody, the method comprising culturing a host cell disclosed herein under suitable conditions so that the polynucleotide is expressed and the isolated antibody is produced.

In another aspect, the instant disclosure provides a method of producing an isolated antibody, the method comprising expressing in a cell:
(a) a first polynucleotide encoding the VH of an antibody disclosed herein and a second polynucleotide encoding the VL of an antibody disclosed herein; or
(b) a first polynucleotide encoding a heavy chain of an antibody disclosed herein and a second polynucleotide encoding a light chain of an antibody disclosed herein, under suitable conditions so that the polynucleotides are expressed and the antibody is produced.

In another aspect, the instant disclosure provides a method of enhancing an immune response in a subject, the method comprising administering to the subject an effective amount of an isolated antibody disclosed herein, a polynucleotide disclosed herein, a vector disclosed herein, a host cell disclosed herein, or a pharmaceutical composition disclosed herein.

In another aspect, the instant disclosure provides a method of treating cancer in a subject, the method comprising administering to the subject an effective amount of an isolated antibody disclosed herein, a polynucleotide disclosed herein, a vector disclosed herein, a host cell disclosed herein, or a pharmaceutical composition disclosed herein.

In certain embodiments, the isolated antibody, polynucleotide, vector, host cell, or pharmaceutical composition is administered, systemically, intravenously, subcutaneously, intratumorally, or is delivered to a tumor draining lymph node.

In certain embodiments, the method further comprises administering an additional therapeutic agent to the subject.

In certain embodiments, the additional therapeutic agent is a chemotherapeutic agent.

In certain embodiments, the additional therapeutic agent is a checkpoint targeting agent. In another embodiment, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-VISTA antibody, an antagonist anti-TIGIT antibody, an antagonist anti-CEACAM1 antibody, an antagonist anti-CD96 antibody, an agonist anti-GITR antibody, and an agonist anti-OX40 antibody. In another embodiment, the additional therapeutic agent is an anti-PD-1 antibody, optionally wherein the anti-PD-1 antibody is pembrolizumab or nivolumab.

In certain embodiments, the additional therapeutic agent is an inhibitor of indoleamine-2,3-dioxygenase (IDO). In another embodiment, the inhibitor is selected from the group consisting of epacadostat, F001287, indoximod, and NLG919.

In certain embodiments, the additional therapeutic agent is a vaccine. In another embodiment, the vaccine comprises a heat shock protein peptide complex (HSPPC) comprising a heat shock protein complexed with an antigenic peptide. In another embodiment, the heat shock protein is hsc70 and is complexed with a tumor-associated antigenic peptide. In another embodiment, the heat shock protein is gp96 protein and is complexed with a tumor-associated antigenic peptide, optionally wherein the HSPPC is derived from a tumor obtained from a subject.

In another aspect, the instant disclosure provides a method of treating an infectious disease in a subject, the method comprising administering to the subject an effective amount of an isolated antibody disclosed herein, a polynucleotide disclosed herein, a vector disclosed herein, a host cell disclosed herein, or a pharmaceutical composition disclosed herein.

6. BRIEF DESCRIPTION OF THE DRAWINGS

Figures 10A, 10B:
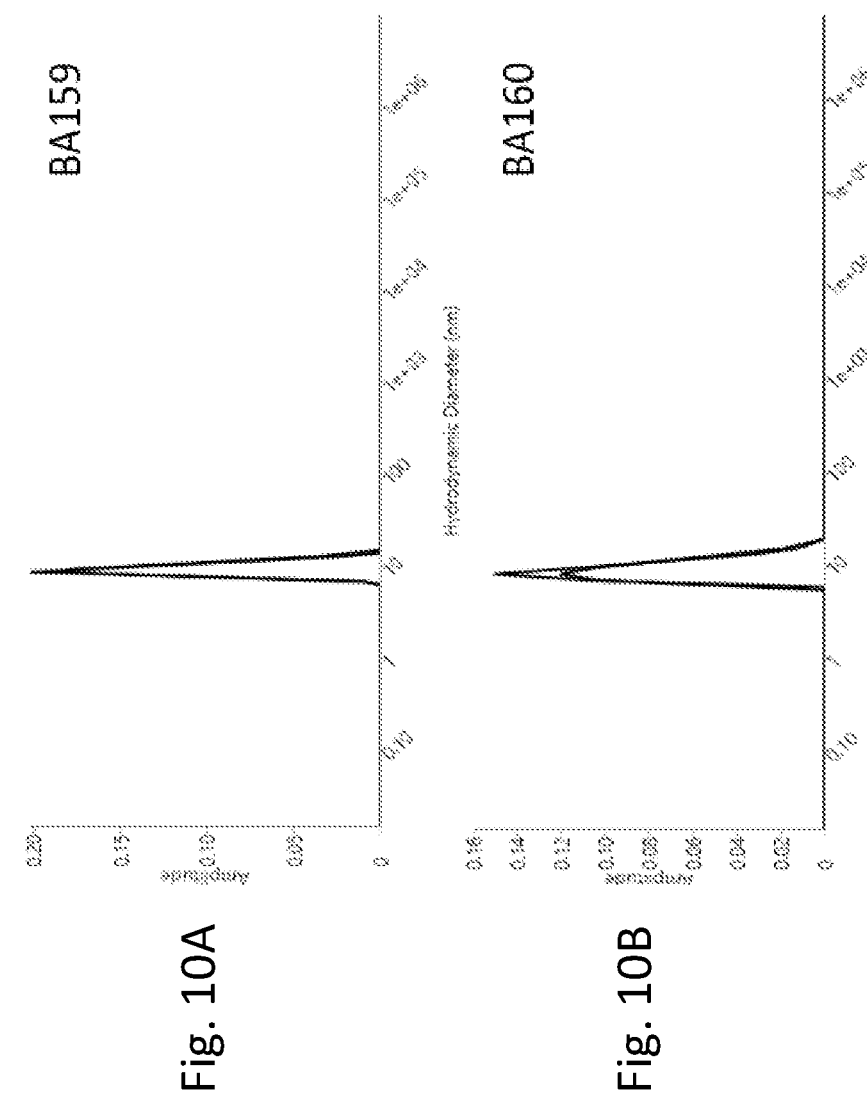
Figure 10C:
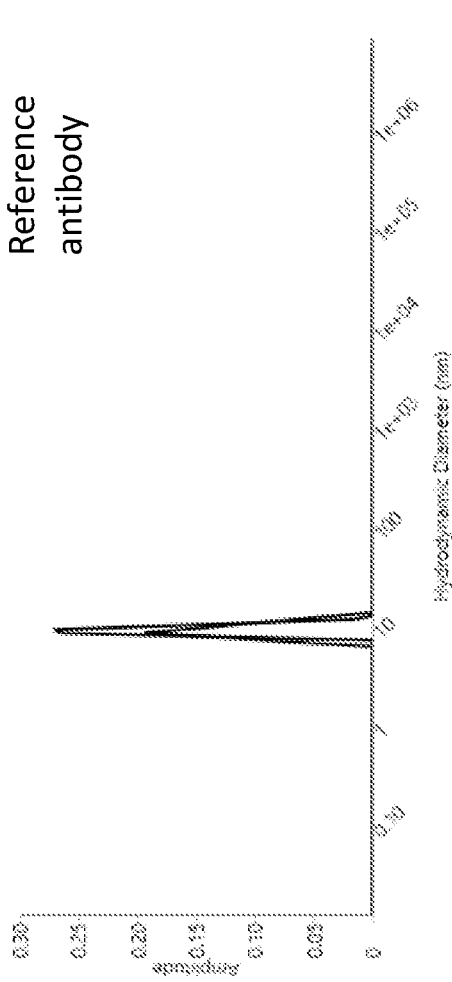

FIG. 10A-FIG. 10C are a series of dynamic light scattering mass distribution graphs showing the calculated average hydrodynamic diameter for BA159 (FIG. 10A), BA160 (FIG. 10B), and an anti-TIGIT reference antibody (FIG. 10C). Each experiment was run in duplicate and both are shown on the same graph. The amplitude is plotted against hydrodynamic diameter.

Figures 11A, 11B:
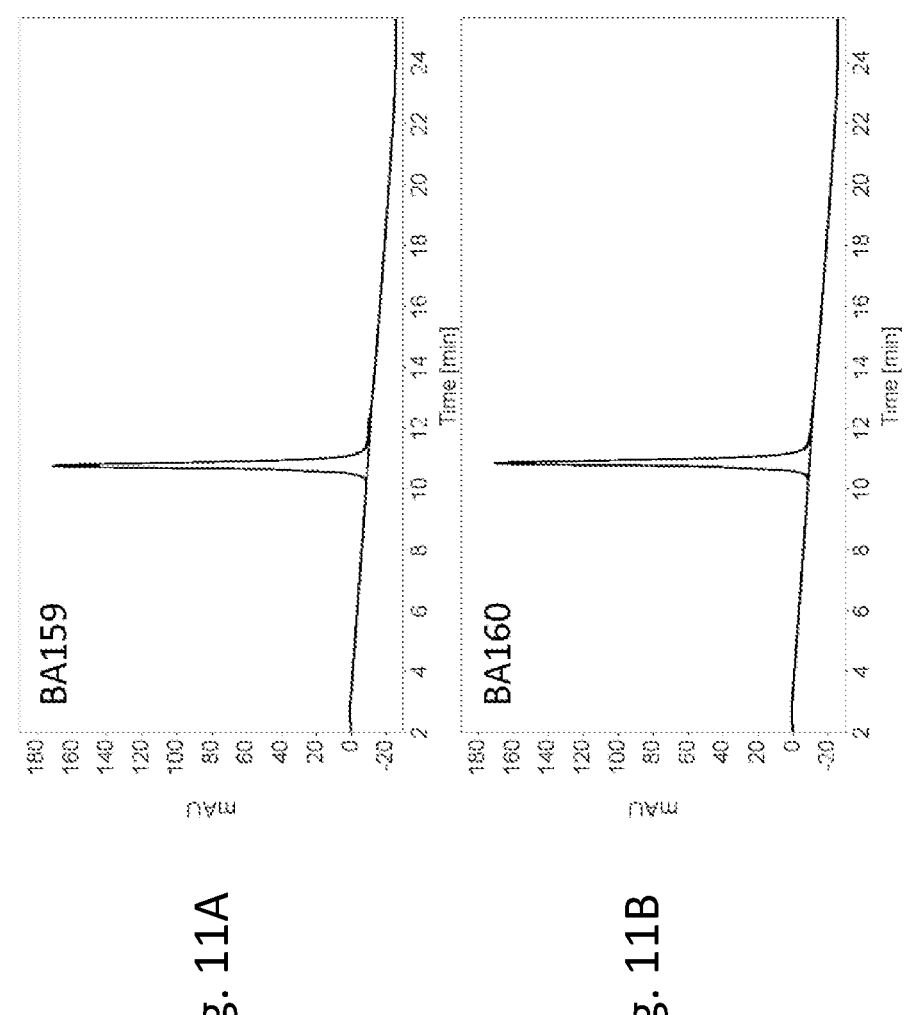
Figure 11C:
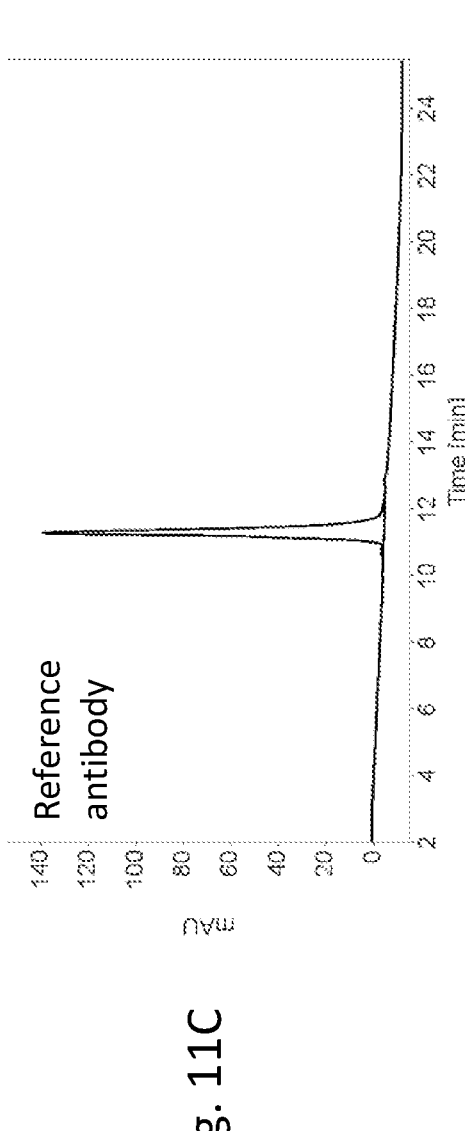
Figures 12A, 12B, 12C:
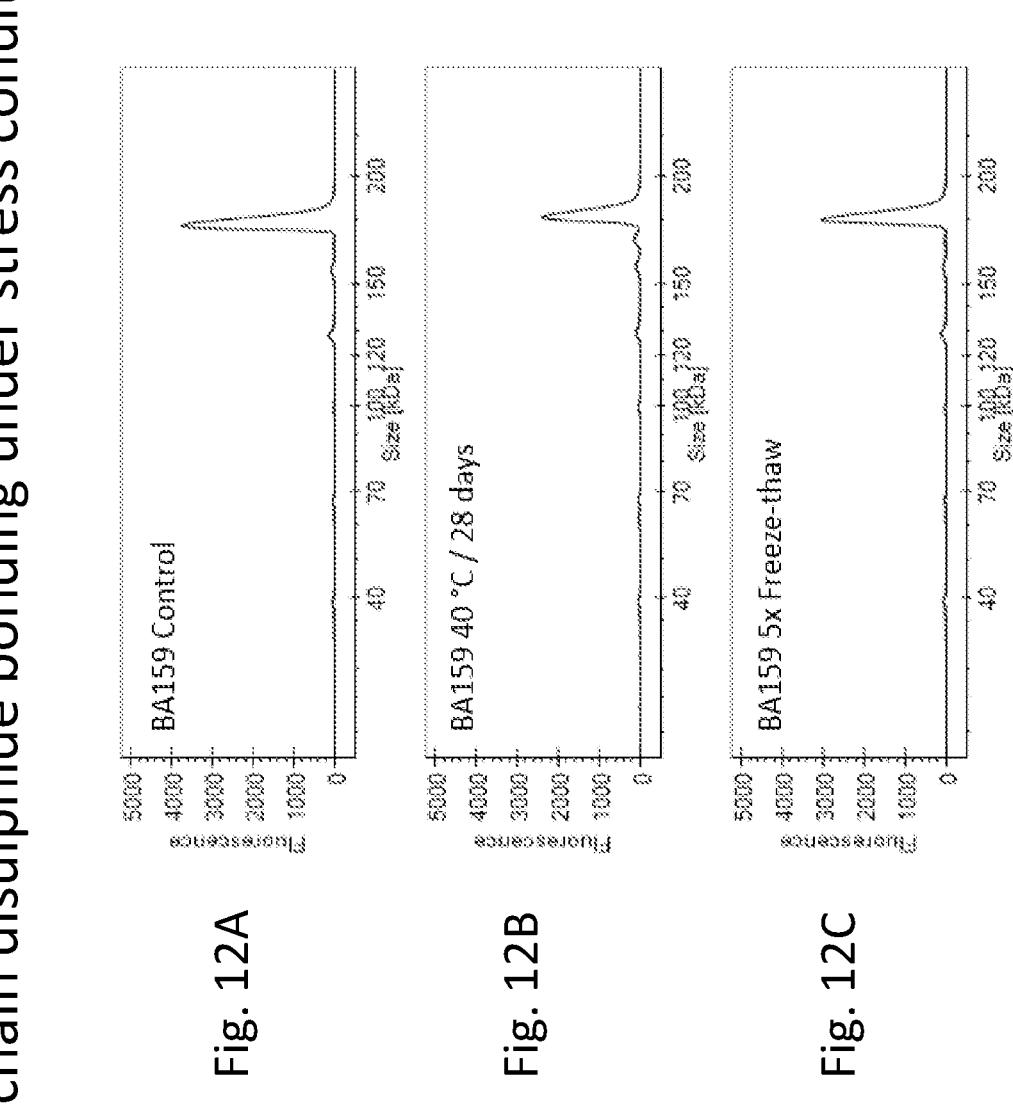
Figures 12D, 12E, 12F:
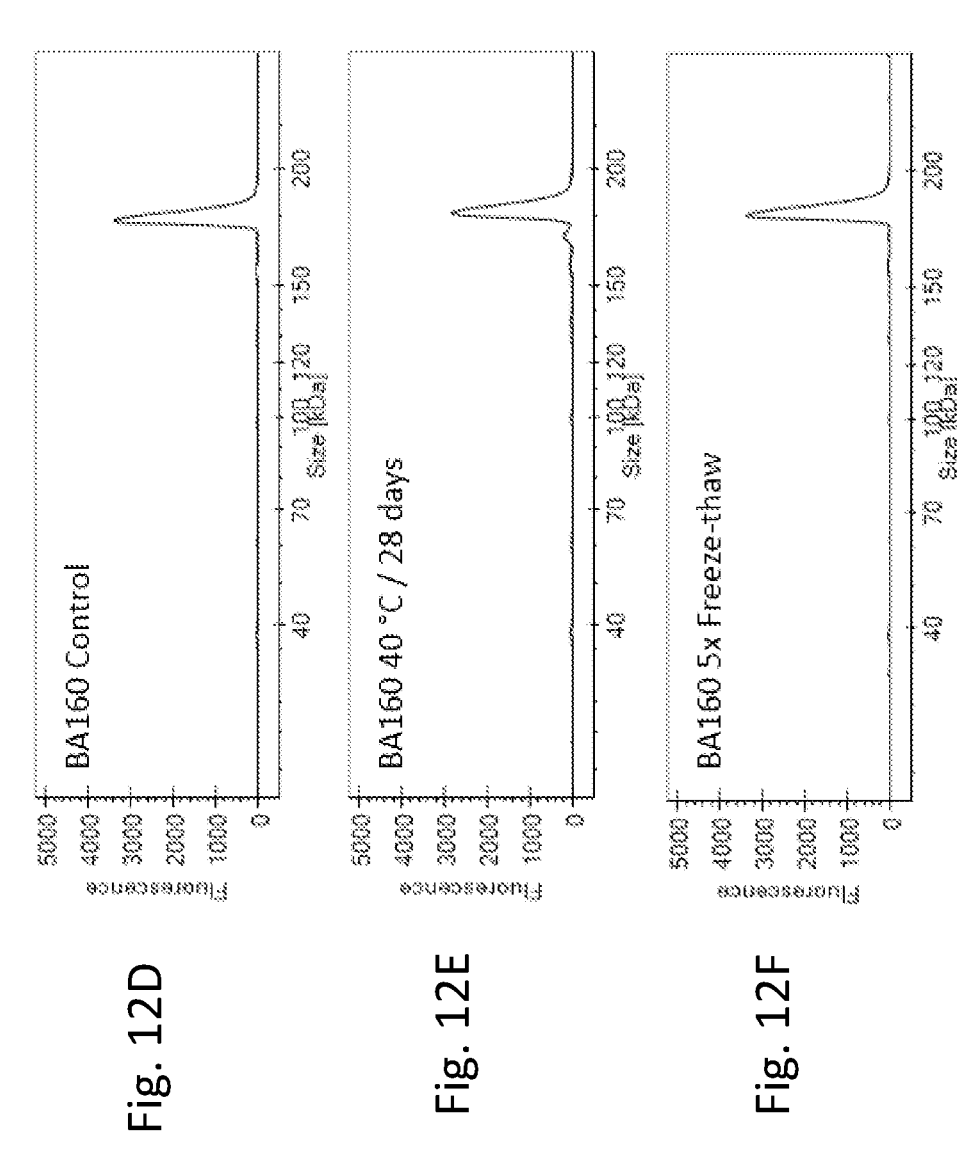
Figures 12G, 12H, 12I:
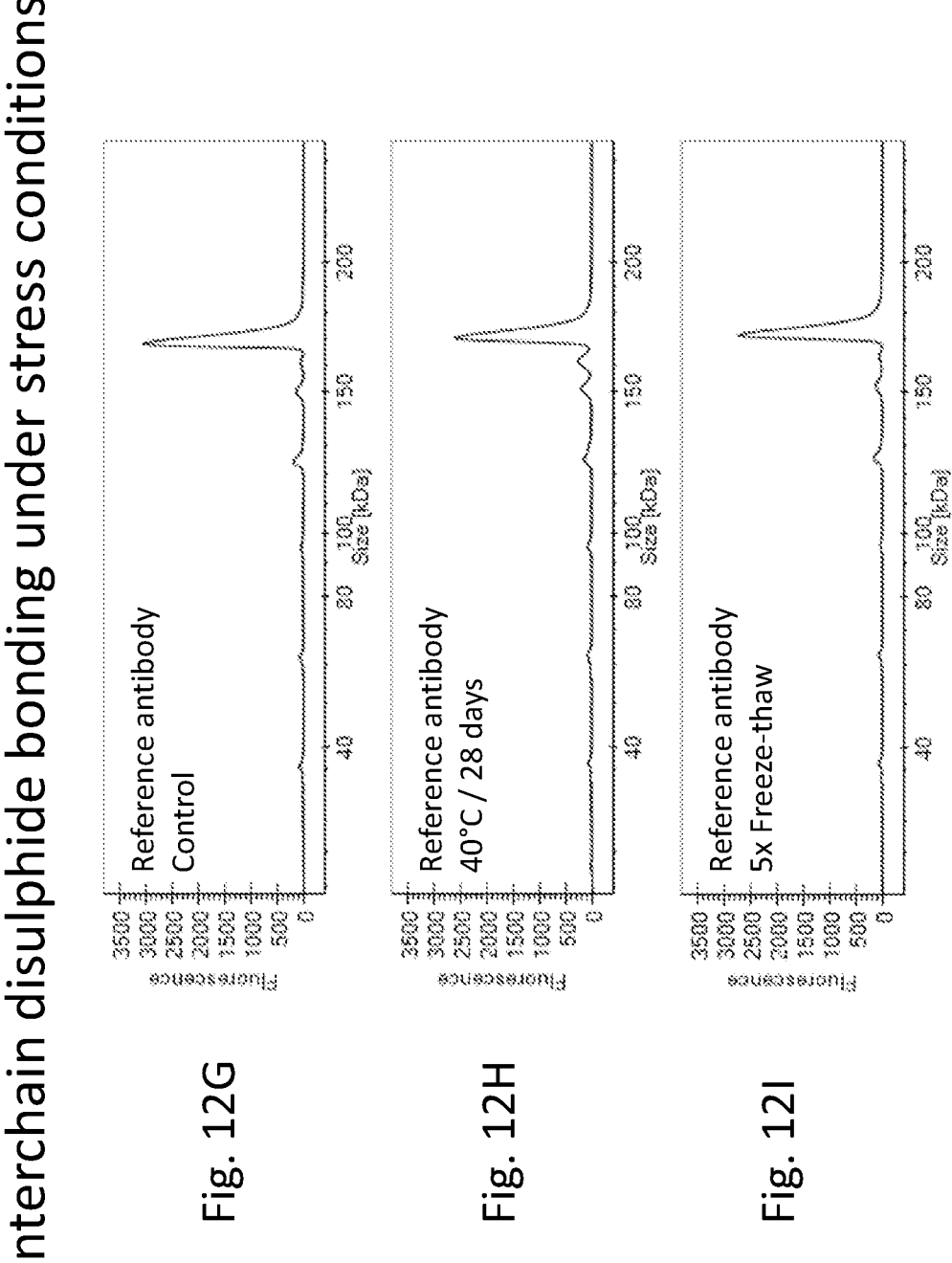
Figures 13A, 13B, 13C:
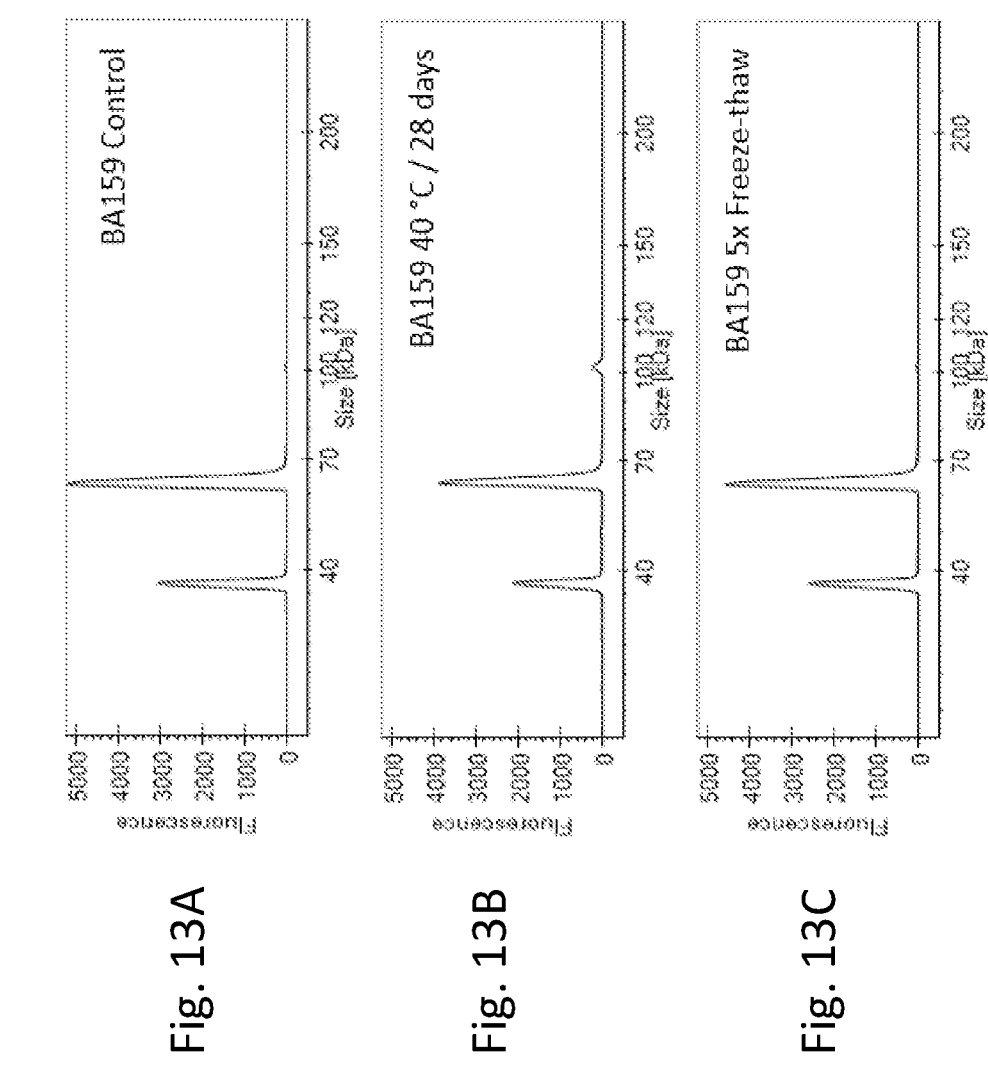
Figures 13D, 13E, 13F:
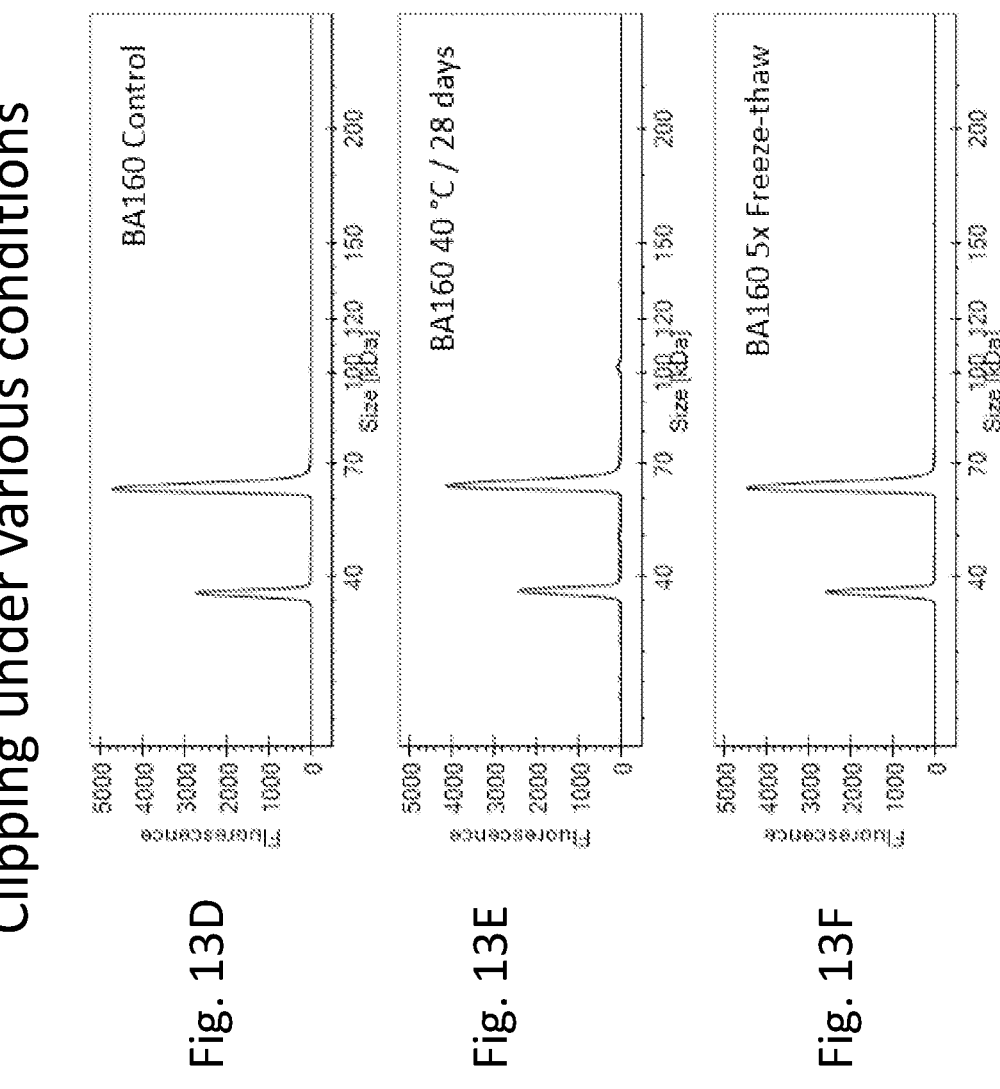
Figures 13G, 13H, 13I:
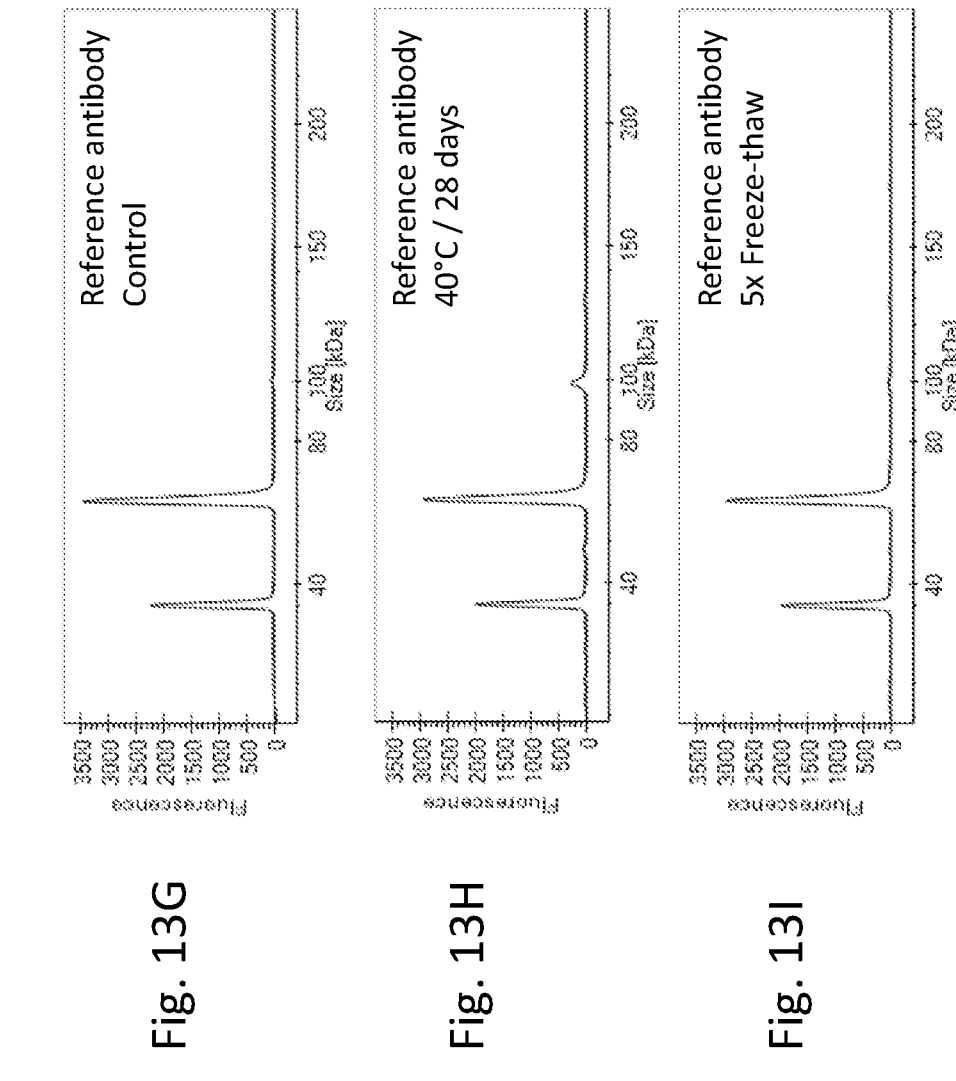
Figures 14A, 14B:
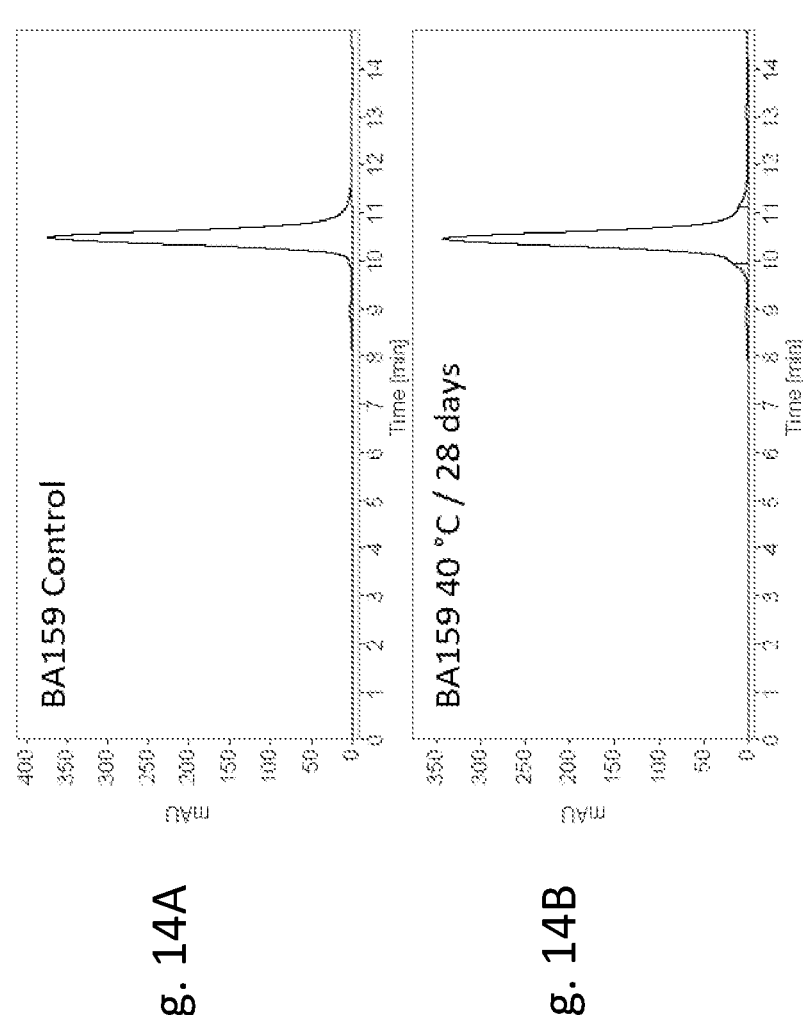
Figure 14C:
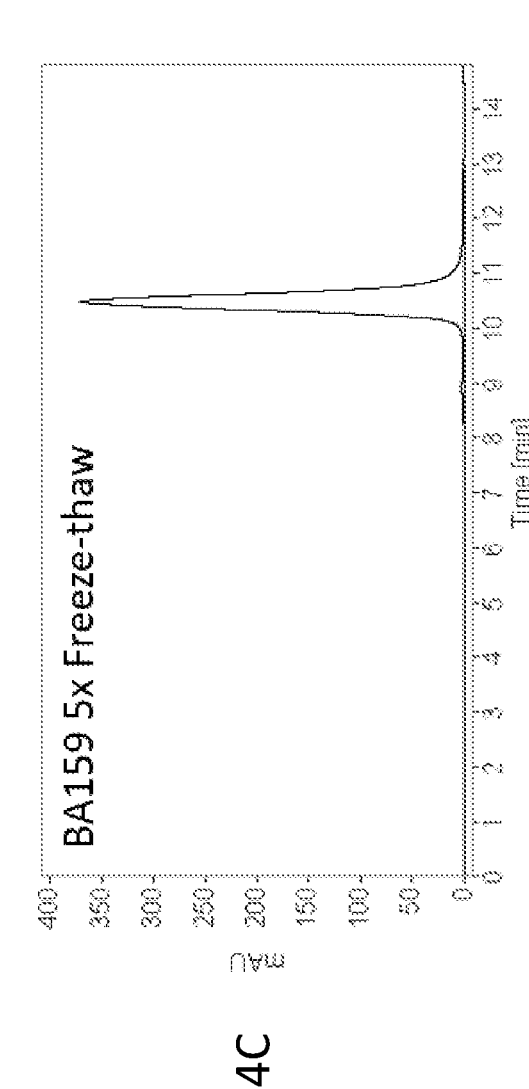
Figures 14D, 14E:
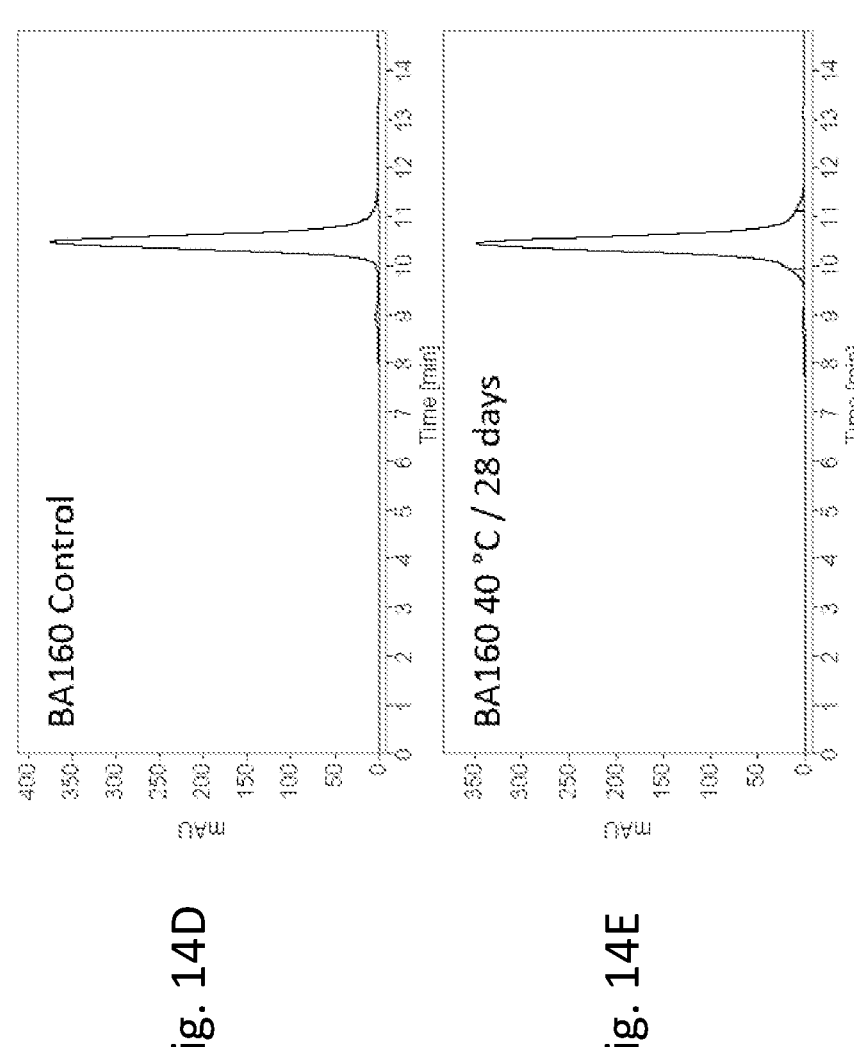
Figure 14F:
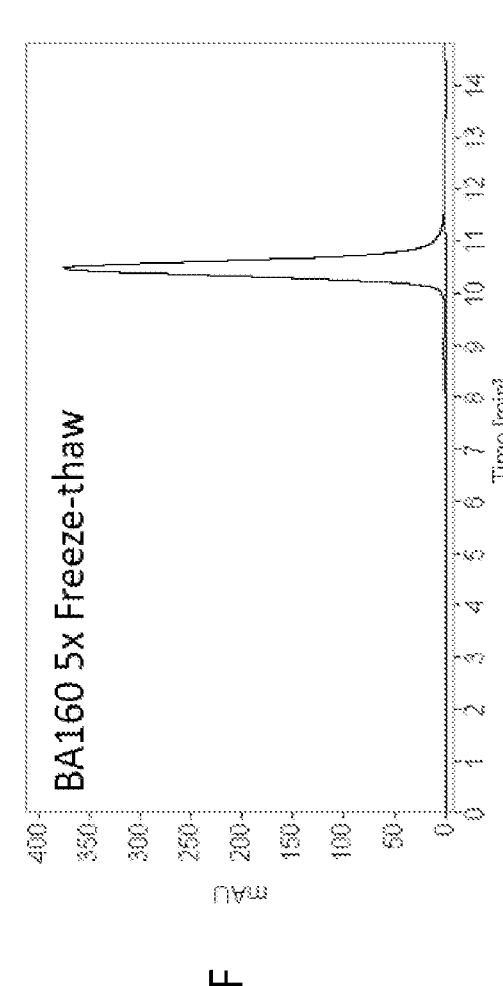
Figures 14G, 14H:
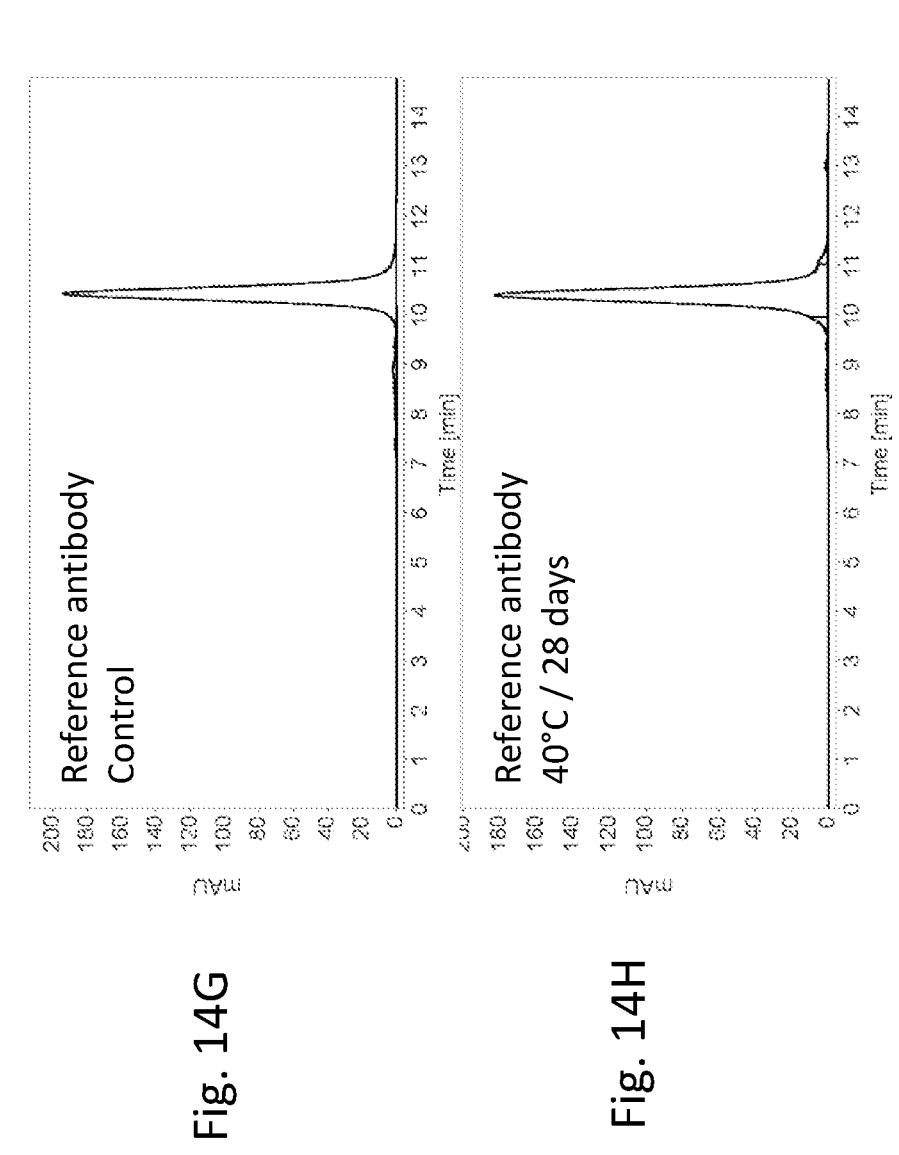
Figure 14I:
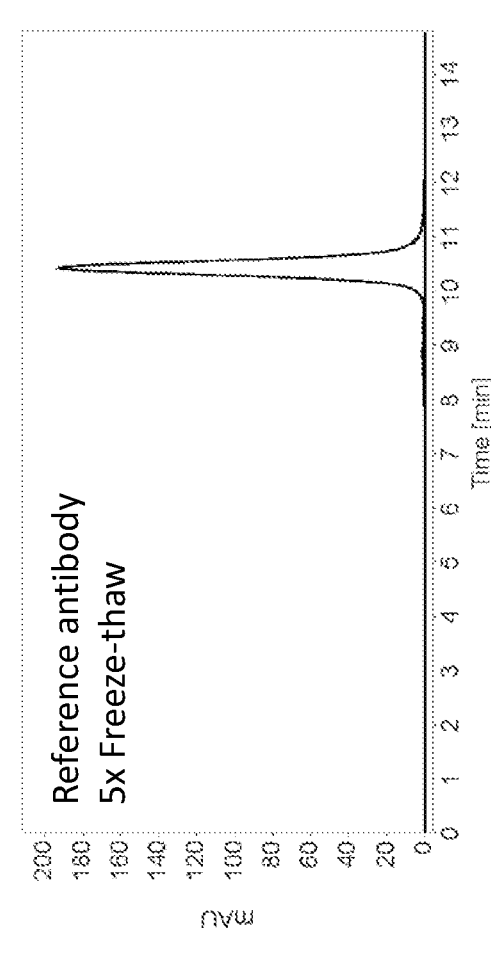

FIG. 11A-FIG. 11C are a series of hydrophobic interaction chromatography traces showing the elution time for BA159 (FIG. 11A), BA160 (FIG. 11B), and an anti-TIGIT reference antibody (FIG. 11C). The absorbance at 229 nm is plotted against retention time.

FIG. 12A-FIG. 12I are a series of non-reducing CE SDS electropherograms showing any changes to interchain disulphide bonding for BA159 (FIG. 12A-FIG. 12C), BA160 (FIG. 12D-FIG. 12F), and an anti-TIGIT reference antibody (FIG. 12G-FIG. 12I) when subjected to no stress, high temperature hold, and repeated freeze-thawing. The fluorescence of molecules running at different sizes is shown.

FIG. 13A-FIG. 13I are a series of reducing CE SDS electropherograms showing any clipping for BA159 (FIG. 13A-FIG. 13C), BA160 (FIG. 13D-FIG. 13F), and an anti-TIGIT reference antibody (FIG. 13G-FIG. 13I) when subjected to no stress, high temperature hold, and repeated freeze-thawing. The fluorescence of molecules running at different sizes is shown.

FIG. 14A-FIG. 14I are a series of size exclusion chromatography traces showing the elution time of BA159 (FIG. 14A-FIG. 14C), BA160 (FIG. 14D-FIG. 14F), and an anti-TIGIT reference antibody (FIG. 14G-FIG. 14I) when subjected to no stress, high temperature hold, and repeated freeze-thawing. The absorbance at 214 nm is plotted against retention time.

FIG. 15A and FIG. 15B are graphs showing the ability of BA159 and an isotype control antibody to bind to activated healthy donor PBMCs over a range of antibody concentrations as measured by mean fluorescence intensity (MFI). FIG. 15A shows binding to CD4+ T cells and FIG. 15B shows binding to CD8+ T cells.

FIG. 16A and FIG. 16B are graphs showing the ability of BA159 and an isotype control antibody to induce luciferase expression as a surrogate for TCR activation and CD226 pathway activation in a reporter assay in which Jurkat reporter cells were co-cultured with CHO cells engineered to express PVR and a TCR activator (artificial antigen-presenting cell (aAPC)). Luciferase expression, shown as relative light units (RLU), was measured in the presence of dose range of BA159 or isotype antibody. FIG. 16A and FIG. 16B represent independent experiments performed on two different days.

Figure 17:
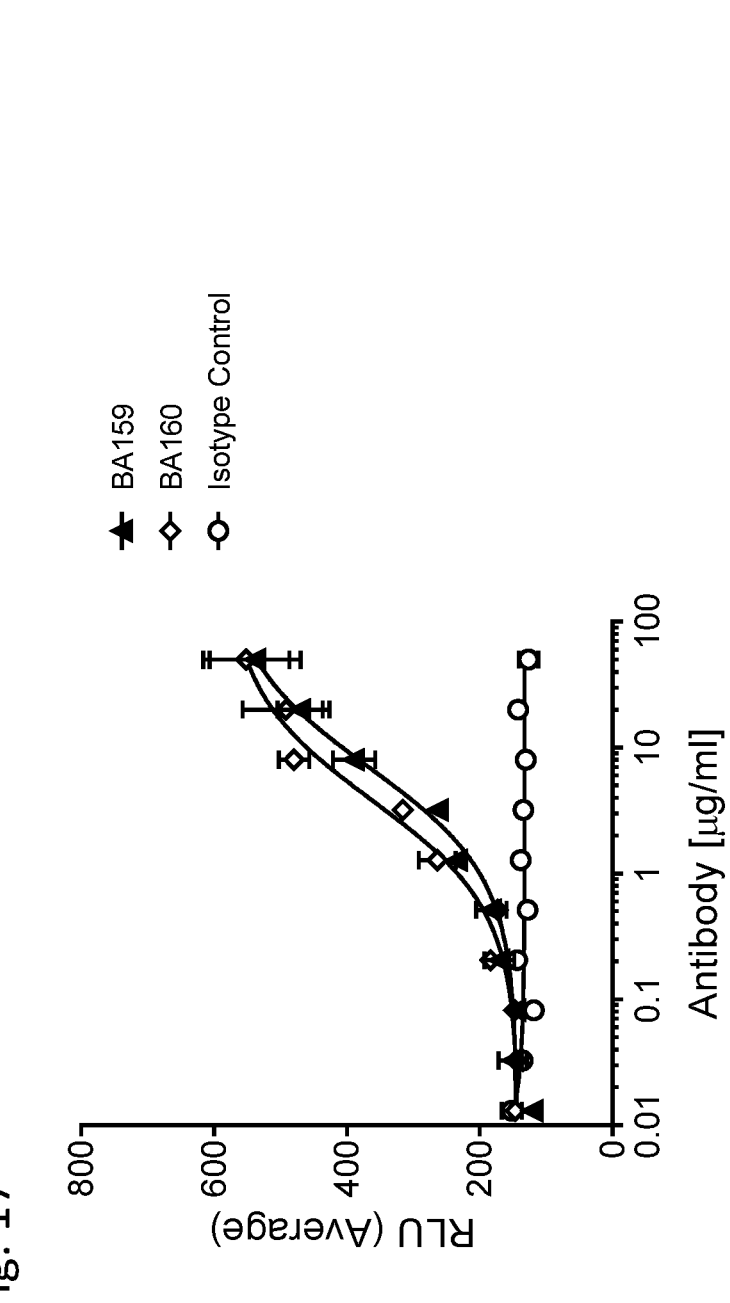

FIG. 17 is a graph showing the ability of BA159, BA160, and an isotype control antibody to block binding of TIGIT, expressed on Jurkat cells, to PVR, expressed on CHO cells. Blocking is expressed as relative light units (RLU) over a range of antibody concentrations.

FIG. 18A-FIG. 18C are a series of graphs showing the ability of BA159, BA260, BA261, BA262, and an isotype control antibody to promote IL-2 secretion by SEA-stimulated PBMCs over a range of antibody concentrations. Each panel represents a different donor.

FIG. 19A and FIG. 19B are graphs showing the ability of BA159, BA260, BA261, BA262, and an isotype control antibody to promote IL-2 secretion by SEA-stimulated PBMCs over a range of antibody concentrations in the presence or absence of an anti-PD-1 antibody. Each panel represents a different donor.

FIG. 20A and FIG. 20B are graphs showing the ability of BA159, BA160, and an isotype control antibody to promote IL-2 secretion by SEA-stimulated PBMCs over a range of antibody concentrations. Each panel represents a different donor.

7. DETAILED DESCRIPTION

The instant disclosure provides isolated anti-TIGIT antibodies. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing immune cell activation, and hence, are useful for treating cancer in a subject or treating or preventing an infectious disease in a subject.

7.1 Definitions

As used herein, the term "TIGIT" refers to T-cell immunoreceptor with Ig and ITIM domains (also known as VSIG9 or VSTM3) that in humans is encoded by the TIGIT gene. As used herein, the term "human TIGIT" refers to a TIGIT protein encoded by a wild-type human TIGIT gene (e.g., GenBank™ accession number NM_173799.3) or an extracellular domain of such a protein. An exemplary amino acid sequence of an extracellular domain of a mature human TIGIT protein is provided as SEQ ID NO: 23. An exemplary amino acid sequence of an extracellular domain of a mature cynomolgus TIGIT protein is provided as SEQ ID NO: 24.

As used herein, the terms "antibody" and "antibodies" include full-length antibodies, antigen-binding fragments of full-length antibodies, and molecules comprising antibody CDRs, VH regions, and/or VL regions. Examples of antibodies include, without limitation, monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affibodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclass (e.g., IgG$_2$a or IgG$_2$b) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody.

"Multispecific antibodies" are antibodies (e.g., bispecific antibodies) that specifically bind to two or more different antigens or two or more different regions of the same antigen. Multispecific antibodies include bispecific antibodies that contain two different antigen-binding sites (exclusive of the Fc region). Multispecific antibodies can include, for example, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, heteroconjugate antibodies, linked-single-chain antibodies or linked-single-chain Fvs (scFv), camelized antibodies, affybodies, linked Fab fragments, F(ab')$_2$ fragments, chemically-linked Fvs, and disulfide-linked Fvs (sdFv). Multispecific antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclass (e.g., IgG$_2$a or IgG$_2$b) of immunoglobulin molecule. In certain embodiments, multispecific antibodies described herein are IgG antibodies, or a class (e.g., human IgG$_1$, IgG$_2$, or IgG$_4$) or subclass thereof.

As used herein, the term "CDR" or "complementarity determining region" means the noncontiguous antigen combining sites found within the variable regions of heavy and light chain polypeptides. These particular regions have been described by, for example, Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. In certain embodiments, the term "CDR" is a CDR as defined by MacCallum et al., J. Mol. Biol. 262:732-745 (1996) and Martin A. "Protein Sequence and Structure Analysis of Antibody Variable Domains," in *Antibody Engineering*, Kontermann and Dithel, eds., Chapter 31, pp. 422-439, Springer-Verlag, Berlin (2001). In certain embodiments, the term "CDR" is a CDR as defined by Kabat et al., J. Biol. Chem. 252, 6609-6616 (1977) and Kabat et al., Sequences of protein of immunological interest. (1991). In certain embodiments, heavy chain CDRs and light chain CDRs of an antibody are defined using different conventions. In certain embodiments, heavy chain CDRs and/or light chain CDRs are defined by performing structural analysis of an antibody and identifying residues in the variable region(s) predicted to make contact with an epitope region of a target molecule (e.g., human and/or cynomolgus TIGIT). CDRH1, CDRH2, and CDRH3 denote the heavy chain CDRs, and CDRL1, CDRL2, and CDRL3 denote the light chain CDRs.

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable region are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In certain embodiments, the variable region is a primate (e.g., non-human primate) variable region. In certain embodiments, the variable region comprises rodent or murine CDRs and primate (e.g., non-human primate) framework regions (FRs).

As used herein, the terms "VH" and "VL" refer to antibody heavy and light chain variable regions, respectively, as described in Kabat et al., (1991) Sequences of Proteins of Immunological Interest (NIH Publication No. 91-3242, Bethesda), which is herein incorporated by reference in its entirety.

As used herein, the term "constant region" is common in the art. The constant region is an antibody portion, e.g., a carboxyl terminal portion of a light and/or heavy chain, which is not directly involved in binding of an antibody to antigen but which can exhibit various effector functions, such as interaction with an Fc receptor (e.g., Fc gamma receptor).

As used herein, the term "heavy chain" when used in reference to an antibody can refer to any distinct type, e.g., alpha ($\alpha$), delta ($\delta$), epsilon ($\varepsilon$), gamma ($\gamma$), and mu ($\mu$), based on the amino acid sequence of the constant region, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa ($\kappa$) or lambda (k), based on the amino acid sequence of the constant region. Light chain amino acid sequences are well known in the art. In specific embodiments, the light chain is a human light chain.

As used herein, the terms "specifically binds," "specifically recognizes," "immunospecifically binds," and "immunospecifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), or other assays known in the art. In a specific embodiment, molecules that specifically bind to an antigen bind to the antigen with a KA that is at least 2 logs (e.g., factors of 10), 2.5 logs, 3 logs, 4 logs or greater than the KA when the molecules bind non-specifically to another antigen.

As used herein, the term "EU numbering system" refers to the EU numbering convention for the constant regions of an antibody, as described in Edelman, G. M. et al., Proc. Natl. Acad. USA, 63, 78-85 (1969) and Kabat et al., Sequences of Proteins of Immunological Interest, U.S. Dept. Health and Human Services, 5th edition, 1991, each of which is herein incorporated by reference in its entirety.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In certain embodiments, the subject is a human or non-human mammal. In certain embodiments, the subject is a human.

As used herein with respect to an antibody or polynucleotide, the term "isolated" refers to an antibody or polynucleotide that is separated from one or more contaminants (e.g., polypeptides, polynucleotides, lipids, or carbohydrates, etc.) which are present in a natural source of the antibody or polynucleotide. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides" described herein are additionally contemplated as polynucleotides that may be, but need not be, isolated.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecule described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

7.2 Anti-TIGIT Antibodies

In one aspect, the instant disclosure provides antibodies that specifically bind to TIGIT (e.g., human TIGIT or cynomolgus TIGIT). The amino acid sequences of exemplary antibodies are set forth in Table 1.

TABLE 1

| | Amino acid sequences of exemplary anti-TIGIT antibodies. | |
|---|---|---|
| Description | Amino Acid Sequence | SEQ ID NO |
| BA159 BA160 BA260 BA261 BA262 | SYGIS | 1 |
| HCDR1 | | |
| BA159 BA160 BA260 BA261 BA262 | GITPFFNRVDVAEKFQG | 2 |
| HCDR2 | | |
| BA159 BA160 BA260 BA261 BA262 | DLRRGGVGDAFDI | 3 |
| HCDR3 | | |
| BA159 BA160 BA260 BA261 BA262 | TGTSSDVGSHNYVS | 4 |
| LCDR1 | | |
| BA159 BA160 BA260 BA261 BA262 | EVSYRPS | 5 |
| LCDR2 | | |
| BA159 BA160 BA260 BA261 BA262 | SSYTPSSATV | 6 |
| LCDR3 | | |
| BA159 BA160 BA261 | EVQLVQSGAEVKKPGSSVKVSCKASGYTFASYGISWVRQAP GQGLEWMGGITPFFNRVDVAEKFQGRVTITADKSTSTAYIE LSSLRSEDTAVYYCARDLRRGGVGDAFDIWGRGTLVTVSS | 7 |
| VH | | |
| BA260 BA262 | EVQLVQSGAEVKKPGSSVKVSCKASGYTFASYGISWVRQAP GQGLEWMGGITPFFNRVDVAEKFQGRVTITADTSTNTVYIE LSSLRSEDTAVYYCARDLRRGGVGDAFDIWGRGTLVTVSS | 8 |
| VH | | |
| BA159 BA160 BA262 | QSALTQPRSVSGSPGQSVTISCTGTSSDVGSHNYVSWYQQH PGKAPKLMIYEVSYRPSGVSNRFSGSKSGNTASLTISGLQA EDEADYYCSSYTPSSATVFGAGTKLTVL | 9 |
| VL | | |
| BA260 BA261 | QSALTQPRSVSGSPGQSVTISCTGTSSDVGSHNYVSWYQQH PGKAPKLMIYEVSYRPSEISNRFSGSKSGNTASLTISGLQA EDEADYYCSSYTPSSATVFGAGTKLTVL | 10 |

TABLE 1-continued

Amino acid sequences of exemplary
anti-TIGIT antibodies.

| Description | Amino Acid Sequence | SEQ ID NO |
|---|---|---|
| VL | | |
| BA159 BA160 BA261 heavy chain | EVQLVQSGAEVKKPGSSVKVSCKASGYTFASYGISWVRQAP GQGLEWMGGITPFFNRVDVAEKFQGRVTITADKSTSTAYIE LSSLRSEDTAVYYCARDLRRGGVGDAFDIWGRGTLVTVSSA STKGPSVFPLAPSSKSTSGGTAALGCLVKDYFPEPVTVSWN SGALTSGVHTFPAVLQSSGLYSLSSVVTVPSSSLGTQTYIC NVNHKPSNTKVDKRVEPKSCDKTHTCPPCPAPELLGGPDVF LFPPKPKDTLMISRTPEVTCVVVDVSHEDPEVKFNWYVDGV EVHNAKTKPREEQYNSTYRVVSVLTVLHQDWLNGKEYKCKV SNKALPLPEEKTISKAKGQPREPQVYTLPPSREEMTKNQVS LTCLVKGFYPSDIAVEWESNGQPENNYKTTPPVLDSDGSFF LYSKLTVDKSRWQQGNVFSCSVMHEALHNHYTQKSLSLSPG K | 11 |
| BA260 BA262 heavy chain | EVQLVQSGAEVKKPGSSVKVSCKASGYTFASYGISWVRQAP GQGLEWMGGITPFFNRVDVAEKFQGRVTITADTSTNTVYIE LSSLRSEDTAVYYCARDLRRGGVGDAFDIWGRGTLVTVSSA STKGPSVFPLAPSSKSTSGGTAALGCLVKDYFPEPVTVSWN SGALTSGVHTFPAVLQSSGLYSLSSVVTVPSSSLGTQTYIC NVNHKPSNTKVDKRVEPKSCDKTHTCPPCPAPELLGGPDVF LFPPKPKDTLMISRTPEVTCVVVDVSHEDPEVKFNWYVDGV EVHNAKTKPREEQYNSTYRVVSVLTVLHQDWLNGKEYKCKV SNKALPLPEEKTISKAKGQPREPQVYTLPPSREEMTKNQVS LTCLVKGFYPSDIAVEWESNGQPENNYKTTPPVLDSDGSFF LYSKLTVDKSRWQQGNVFSCSVMHEALHNHYTQKSLSLSPG K | 12 |
| BA159 BA262 light chain | QSALTQPRSVSGSPGQSVTISCTGTSSDVGSHNYVSWYQQH PGKAPKLMIYEVSYRPSGVSNRFSGSKSGNTASLTISGLQA EDEADYYCSSYTPSSATVFGAGTKLTVLGQPKAAPSVTLFP PSSEELQANKATLVCLISDFYPGAVTVAWKADSSPVKAGVE TTTPSKQSNNKYAASSYLSLTPEQWKSHRSYSCQVTHEGST VEKTVAPTECS | 13 |
| BA160 light chain | QSALTQPRSVSGSPGQSVTISCTGTSSDVGSHNYVSWYQQH PGKAPKLMIYEVSYRPSGVSNRFSGSKSGNTASLTISGLQA EDEADYYCSSYTPSSATVFGAGTKLTVLGQPKAAPSVTLFP PSSEELQANKATLVCLISDFYPGAVTVAWKADSSPVKAGVE TTTPSKQSNNKYAASSYLSLTPEQWKSHRSYSCQVTHEGST VEKTVAPTEC | 14 |
| BA260 BA261 light chain | QSALTQPRSVSGSPGQSVTISCTGTSSDVGSHNYVSWYQQH PGKAPKLMIYEVSYRPSEISNRFSGSKSGNTASLTISGLQA EDEADYYCSSYTPSSATVFGAGTKLTVLGQPKAAPSVTLFP PSSEELQANKATLVCLISDFYPGAVTVAWKADSSPVKAGVE TTTPSKQSNNKYAASSYLSLTPEQWKSHRSYSCQVTHEGST VEKTVAPTECS | 15 |
| BA159 BA160 BA260 BA261 BA262 heavy chain constant region | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPELLGGPDV FLFPPKPKDTLMISRTPEVTCVVVDVSHEDPEVKFNWYVDG VEVHNAKTKPREEQYNSTYRVVSVLTVLHQDWLNGKEYKCK VSNKALPLPEEKTISKAKGQPREPQVYTLPPSREEMTKNQV SLTCLVKGFYPSDIAVEWESNGQPENNYKTTPPVLDSDGSF FLYSKLTVDKSRWQQGNVFSCSVMHEALHNHYTQKSLSLSP GK | 16 |
| BA159 BA260 BA261 BA262 light chain constant region | GQPKAAPSVTLFPPSSEELQANKATLVCLISDFYPGAVTVA WKADSSPVKAGVETTTPSKQSNNKYAASSYLSLTPEQWKSH RSYSCQVTHEGSTVEKTVAPTECS | 17 |
| BA160 light chain constant region | GQPKAAPSVTLFPPSSEELQANKATLVCLISDFYPGAVTVA WKADSSPVKAGVETTTPSKQSNNKYAASSYLSLTPEQWKSH RSYSCQVTHEGSTVEKTVAPTEC | 18 |

TABLE 1-continued

Amino acid sequences of exemplary
anti-TIGIT antibodies.

| Description | Amino Acid Sequence | SEQ ID NO |
|---|---|---|
| BA159<br>BA160<br>BA261<br>delta<br>K heavy<br>chain | EVQLVQSGAEVKKPGSSVKVSCKASGYTFASYGISWVRQAP<br>GQGLEWMGGITPFFNRVDVAEKFQGRVTITADKSTSTAYIE<br>LSSLRSEDTAVYYCARDLRRGGVGDAFDIWGRGTLVTVSSA<br>STKGPSVFPLAPSSKSTSGGTAALGCLVKDYFPEPVTVSWN<br>SGALTSGVHTFPAVLQSSGLYSLSSVVTVPSSSLGTQTYIC<br>NVNHKPSNTKVDKRVEPKSCDKTHTCPPCPAPELLGGPDVF<br>LFPPKPKDTLMISRTPEVTCVVVDVSHEDPEVKFNWYVDGV<br>EVHNAKTKPREEQYNSTYRVVSVLTVLHQDWLNGKEYKCKV<br>SNKALPLPEEKTISKAKGQPREPQVYTLPPSREEMTKNQVS<br>LTCLVKGFYPSDIAVEWESNGQPENNYKTTPPVLDSDGSFF<br>LYSKLTVDKSRWQQGNVFSCSVMHEALHNHYTQKSLSLSPG | 19 |
| BA260<br>BA262<br>delta<br>K heavy<br>chain | EVQLVQSGAEVKKPGSSVKVSCKASGYTFASYGISWVRQAP<br>GQGLEWMGGITPFFNRVDVAEKFQGRVTITADTSTNTVYIE<br>LSSLRSEDTAVYYCARDLRRGGVGDAFDIWGRGTLVTVSSA<br>STKGPSVFPLAPSSKSTSGGTAALGCLVKDYFPEPVTVSWN<br>SGALTSGVHTFPAVLQSSGLYSLSSVVTVPSSSLGTQTYIC<br>NVNHKPSNTKVDKRVEPKSCDKTHTCPPCPAPELLGGPDVF<br>LFPPKPKDTLMISRTPEVTCVVVDVSHEDPEVKFNWYVDGV<br>EVHNAKTKPREEQYNSTYRVVSVLTVLHQDWLNGKEYKCKV<br>SNKALPLPEEKTISKAKGQPREPQVYTLPPSREEMTKNQVS<br>LTCLVKGFYPSDIAVEWESNGQPENNYKTTPPVLDSDGSFF<br>LYSKLTVDKSRWQQGNVFSCSVMHEALHNHYTQKSLSLSPG | 20 |
| BA260<br>BA261<br>delta S<br>light<br>chain | QSALTQPRSVSGSPGQSVTISCTGTSSDVGSHNYVSWYQQH<br>PGKAPKLMIYEVSYRPSEISNRFSGSKSGNTASLTISGLQA<br>EDEADYYCSSYTPSSATVFGAGTKLTVLGQPKAAPSVTLFP<br>PSSEELQANKATLVCLISDFYPGAVTVAWKADSSPVKAGVE<br>TTTPSKQSNNKYAASSYLSLTPEQWKSHRSYSCQVTHEGST<br>VEKTVAPTEC | 21 |
| BA159<br>BA160<br>BA260<br>BA261<br>BA262<br>delta<br>K<br>heavy<br>chain<br>constant<br>region | ASTKGPSVFPLAPSSKSTSGGTAALGCLVKDYFPEPVTVSW<br>NSGALTSGVHTFPAVLQSSGLYSLSSVVTVPSSSLGTQTYI<br>CNVNHKPSNTKVDKRVEPKSCDKTHTCPPCPAPELLGGPDV<br>FLFPPKPKDTLMISRTPEVTCVVVDVSHEDPEVKFNWYVDG<br>VEVHNAKTKPREEQYNSTYRVVSVLTVLHQDWLNGKEYKCK<br>VSNKALPLPEEKTISKAKGQPREPQVYTLPPSREEMTKNQV<br>SLTCLVKGFYPSDIAVEWESNGQPENNYKTTPPVLDSDGSF<br>FLYSKLTVDKSRWQQGNVFSCSVMHEALHNHYTQKSLSLSP<br>G | 22 |

TABLE 2

Exemplary TIGIT sequences.

| Description | Amino Acid Sequence | SEQ ID NO |
|---|---|---|
| Exemplary<br>Human TIGIT<br>extracellular<br>domain | MMTGTIETTGNISAEKGGSI<br>ILQCHLSSTTAQVTQVNWEQ<br>QDQLLAICNADLGWHISPSF<br>KDRVAPGPGLGLTLQSLTVN<br>DTGEYFCIYHTYPDGTYTGR<br>IFLEVLESSVAEHGARFQ | 23 |
| Exemplary Cyno<br>TIGIT<br>extracellular<br>domain | MMTGTIETTGNISAKKGGSV<br>ILQCHLSSTMAQVTQVNWEQ<br>HDHSLLAIRNAELGWHIYPA<br>FKDRVAPGPGLGLTLQSLTM<br>NDTGEYFCTYHTYPDGTYRG<br>RIFLEVLESSVAEHSARFQ | 24 |

In certain embodiments, the instant disclosure provides an isolated antibody that specifically binds to TIGIT (e.g., human TIGIT or cynomolgus TIGIT), the antibody comprising a VH domain comprising one, two, or all three of the CDRs of a VH domain set forth in Table 1. In certain embodiments, the antibody comprises the CDRH1 of a VH domain set forth in Table 1. In certain embodiments, the antibody comprises the CDRH2 of a VH domain set forth in Table 1. In certain embodiments, the antibody comprises the CDRH3 of a VH domain set forth in Table 1.

In certain embodiments, the instant disclosure provides an isolated antibody that specifically binds to TIGIT (e.g., human TIGIT or cynomolgus TIGIT), the antibody comprising a VL domain comprising one, two, or all three of the CDRs of a VL domain disclosed in Table 1. In certain embodiments, the antibody comprises the CDRL1 of a VL domain set forth in Table 1. In certain embodiments, the antibody comprises the CDRL2 of a VL domain set forth in Table 1. In certain embodiments, the antibody comprises the CDRL3 of a VL domain set forth in Table 1.

The individual CDRs of an antibody disclosed herein can be determined according to any CDR numbering scheme known in the art.

In certain embodiments, one or more of the CDRs of an antibody disclosed herein can be determined according to Kabat et al., J. Biol. Chem. 252, 6609-6616 (1977) and Kabat et al., Sequences of protein of immunological interest (1991), each of which is herein incorporated by reference in its entirety.

In certain embodiments, the instant disclosure provides antibodies that specifically bind to TIGIT (e.g., human TIGIT or cynomolgus TIGIT) and comprise CDRs of an antibody disclosed in Table 1 herein as determined by the Kabat numbering scheme.

In certain embodiments, one or more of the CDRs of an antibody disclosed herein can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties).

In certain embodiments, the instant disclosure provides antibodies that specifically bind to TIGIT (e.g., human TIGIT or cynomolgus TIGIT) and comprise CDRs of an antibody disclosed in Table 1 herein, as determined by the Chothia numbering system.

In certain embodiments, one or more of the CDRs of an antibody disclosed herein can be determined according to MacCallum R M et al., (1996) J Mol Biol 262: 732-745, herein incorporated by reference in its entirety. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001), herein incorporated by reference in its entirety.

In certain embodiments, the instant disclosure provides antibodies that specifically bind to TIGIT (e.g., human TIGIT or cynomolgus TIGIT) and comprise CDRs of an antibody disclosed in Table 1 herein, as determined by the MacCallum numbering system.

In certain embodiments, the CDRs of an antibody disclosed herein can be determined according to the IMGT numbering system as described in: Lefranc M-P, (1999) The Immunologist 7: 132-136; Lefranc M-P et al., (1999) Nucleic Acids Res 27: 209-212, each of which is herein incorporated by reference in its entirety; and Lefranc M-P et al., (2009) Nucleic Acids Res 37: D1006-D1012.

In certain embodiments, the instant disclosure provides antibodies that specifically bind to TIGIT (e.g., human TIGIT or cynomolgus TIGIT) and comprise CDRs of an antibody disclosed in Table 1 herein, as determined by the IMGT numbering system.

In certain embodiments, the CDRs of an antibody disclosed herein can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety.

In certain embodiments, the instant disclosure provides antibodies that specifically bind to TIGIT (e.g., human TIGIT or cynomolgus TIGIT) and comprise CDRs of an antibody disclosed in Table 1 herein as determined by the AbM numbering scheme.

In certain embodiments, the CDRs of an antibody disclosed herein can be determined according to the AHo numbering system, as described in Honegger and Plückthun, A., J. Mol. Biol. 309:657-670 (2001), herein incorporated by reference in its entirety.

In certain embodiments, the instant disclosure provides antibodies that specifically bind to TIGIT (e.g., human TIGIT or cynomolgus TIGIT) and comprise CDRs of an antibody disclosed in Table 1 herein, as determined by the AHo numbering system.

In certain embodiments, the individual CDRs of an antibody disclosed herein are each independently determined according to one of the Kabat, Chothia, MacCallum, IMGT, AHo, or AbM numbering schemes, or by structural analysis of the multispecific molecule, wherein the structural analysis identifies residues in the variable region(s) predicted to make contact with an epitope region of TIGIT.

In certain embodiments, the instant disclosure provides antibodies that specifically bind to TIGIT (e.g., human TIGIT or cynomolgus TIGIT) and comprise a VH comprising the CDRH1, CDRH2, and CDRH3 region amino acid sequences of a VH set forth in SEQ ID NO: 7 or 8, and a VL comprising the CDRL1, CDRL2, and CDRL3 region amino acid sequences of a VL set forth in SEQ ID NO: 9 or 10, wherein each CDR is independently determined according to one of the Kabat, Chothia, MacCallum, IMGT, AHo, or AbM numbering schemes, or by structural analysis of the multispecific molecule, wherein the structural analysis identifies residues in the variable region(s) predicted to make contact with an epitope region of TIGIT (e.g., human TIGIT or cynomolgus TIGIT).

In certain embodiments, the instant disclosure provides an isolated antibody that specifically binds to TIGIT (e.g., human TIGIT or cynomolgus TIGIT), wherein the isolated antibody comprises a VH comprising the CDRH1, CDRH2, and CDRH3 amino acid sequences set forth in SEQ ID NOs: 1, 2, and 3, respectively.

In certain embodiments, the instant disclosure provides an isolated antibody that specifically binds to TIGIT (e.g., human TIGIT or cynomolgus TIGIT), wherein the isolated antibody comprises a VL comprising the CDRL1, CDRL2, and CDRL3 amino acid sequences set forth in SEQ ID NOs: 4, 5, and 6, respectively.

In certain embodiments, the instant disclosure provides an isolated antibody that specifically binds to TIGIT (e.g., human TIGIT or cynomolgus TIGIT), wherein the isolated antibody comprises a VH comprising CDRH1, CDRH2, and CDRH3 regions, and a VL comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 2, 3, 4, 5, and 6, respectively.

In certain embodiments, the instant disclosure provides an isolated antibody that specifically binds to TIGIT (e.g., human TIGIT or cynomolgus TIGIT) comprising a VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 7 or 8. In certain embodiments, the instant disclosure provides an isolated antibody that specifically binds to TIGIT (e.g., human TIGIT or cynomolgus TIGIT), comprising a VH comprising an amino acid sequence set forth in SEQ ID NO: 7 or 8. In certain embodiments, the amino acid sequence of the VH consists of the amino acid sequence set forth in SEQ ID NO: 7 or 8.

In certain embodiments, the instant disclosure provides an isolated antibody that specifically binds to TIGIT (e.g., human TIGIT or cynomolgus TIGIT), comprising a VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 9 or 10. In certain embodiments, the instant disclosure provides an isolated antibody that specifically binds to TIGIT (e.g., human TIGIT or cynomolgus TIGIT), comprising a VL comprising an amino acid sequence set forth in SEQ ID NO: 9 or 10. In certain embodiments, the amino acid sequence of the VL consists of the amino acid sequence set forth in SEQ ID NO: 9 or 10.

In certain embodiments, the instant disclosure provides an isolated antibody that specifically binds to TIGIT (e.g., human TIGIT or cynomolgus TIGIT), comprising a VH comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 7 or 9, and a VL comprising an amino acid sequence that is at least 75%, 80%, 85%, 90%, 95%, or 100% (e.g., at least 86, 87, 88, 89, 90, 91, 92, 93, 94, 95, 96, 97, 98, or 99%) identical to the amino acid sequence set forth in SEQ ID NO: 9 or 10. In certain embodiments, the instant disclosure provides an isolated antibody that specifically binds to TIGIT (e.g., human TIGIT or cynomolgus TIGIT), comprising a VH comprising an amino acid sequence of SEQ ID NO: 7 or 8, and a VL comprising an amino acid sequence of SEQ ID NO: 9 or 10. In certain embodiments, the amino acid sequence of the VH consists of the amino acid sequence set forth in SEQ ID NO: 7 or 8; and the amino acid sequence of the VL consists of the amino acid sequence set forth in SEQ ID NO: 9 or 10.

In certain embodiments, the instant disclosure provides an isolated antibody that specifically binds to TIGIT (e.g., human TIGIT or cynomolgus TIGIT), comprising the VH and VL amino acid sequences set forth in SEQ ID NOs: 7 and 9; 7 and 10; 8 and 9; or 8 and 10, respectively. In certain embodiments, the amino acid sequences of VH and VL consist of the amino acid sequences set forth in SEQ ID NOs: 7 and 9; 7 and 10; 8 and 9; or 8 and 10, respectively.

In certain embodiments, the instant disclosure provides an isolated antibody that cross-competes for binding to TIGIT (e.g., human TIGIT or cynomolgus TIGIT) with an antibody comprising the VH and VL amino acid sequences set forth in SEQ ID NOs: 7 and 9; 7 and 10; 8 and 9; or 8 and 10, respectively.

In certain embodiments, the instant disclosure provides an isolated antibody that binds to the same or an overlapping epitope of TIGIT (e.g., an epitope of human TIGIT or an epitope of cynomolgus TIGIT) as an antibody described herein, e.g., an antibody comprising the VH and VL amino acid sequences set forth in SEQ ID NOs: 7 and 9; 7 and 10; 8 and 9; or 8 and 10, respectively.

In certain embodiments, the epitope of an antibody can be determined by, e.g., NMR spectroscopy, surface plasmon resonance (BIAcore®), X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, all of which are herein incorporated by reference in their entireties). Antibody: antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds. Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed. Carter C W; Roversi P et al., (2000) Acta Crystallogr D Biol Crystallogr 56(Pt 10): 1316-1323, all of which are herein incorporated by reference in their entireties). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. In addition, or antibodies that recognize and bind to the same or overlapping epitopes of TIGIT (e.g., human TIGIT or cynomolgus TIGIT) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as TIGIT (e.g., human TIGIT or cynomolgus TIGIT). Numerous types of competitive binding assays are known, for example: solid phase direct or indirect radioimmunoassay (MA), solid phase direct or indirect enzyme immunoassay (ETA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label MA using 1-125 label (see Morel G A et al., (1988) Mol Immunol 25(1): 7-15); solid phase direct biotin-avidin EIA (see Cheung R C et al., (1990) Virology 176: 546-52); and direct labeled MA (see Moldenhauer G et al., (1990) Scand J Immunol 32: 77-82), all of which are herein incorporated by reference in their entireties. Typically, such an assay involves the use of purified antigen (e.g., TIGIT, such as human TIGIT or cynomolgus TIGIT) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually, the test immunoglobulin is present in excess. Usually, when a competing antibody is present in excess, it will inhibit specific binding of a reference or antibody to a common antigen by at least 50-55%, 55-60%, 60-65%, 65-70%, 70-75%, or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, ed. Harlow E & Lane D editors supra, pp. 386-389, all of which are herein incorporated by reference in their entireties.

In certain embodiments, the antibody inhibits the binding of human TIGIT to human CD155 (also known as poliovirus receptor (PVR)). In certain embodiments, the binding of human TIGIT to human CD155 is reduced by more than 50%, 55%, 60%, 65%, 70%, 75%, 80%, 85%, 90%, 95%, 96%, 97%, 98%, or 99% in the presence of the antibody relative to the binding of human TIGIT to human CD155 in the absence of the antibody.

In certain embodiments, the antibody inhibits a soluble fragment of human TIGIT from binding to a soluble fragment of human CD155. In certain embodiments, the binding of a soluble fragment of human TIGIT to a soluble fragment of human CD155 is reduced by more than 50%, 55%, 60%, 65%, 70%, 75%, 80%, 85%, 90%, 95%, 96%, 97%, 98%, or 99% in the presence of the antibody relative to the binding of a soluble fragment of human TIGIT to a soluble fragment of human CD155 in the absence of the antibody.

In certain embodiments, the antibody inhibits a TIGIT-expressing cell from binding to a soluble fragment of human CD155. In certain embodiments, the binding of a TIGIT-expressing cell to a soluble fragment of human CD155 is reduced by more than 50%, 55%, 60%, 65%, 70%, 75%, 80%, 85%, 90%, 95%, 96%, 97%, 98%, or 99% in the presence of the antibody relative to the binding of a TIGIT-expressing cell to a soluble fragment of human CD155 in the absence of the antibody.

In certain embodiments, the antibody inhibits a TIGIT-expressing cell from binding to a cell expressing human CD155. In certain embodiments, the binding of a TIGIT-expressing cell to a CD155-expressing cell is reduced by more than 50%, 55%, 60%, 65%, 70%, 75%, 80%, 85%, 90%, 95%, 96%, 97%, 98%, or 99% in the presence of the antibody relative to the binding of a TIGIT-expressing cell to a CD155-expressing cell in the absence of the antibody.

In certain embodiments, the instant disclosure provides an isolated antibody that specifically binds to TIGIT (e.g., human TIGIT or cynomolgus TIGIT), the antibody comprising a heavy chain comprising the amino acid sequence set forth in SEQ ID NO: 11, 12, 19, or 20. In certain embodiments, the amino acid sequence of the heavy chain consists of the amino acid sequence set forth in SEQ ID NO: 11, 12, 19, or 20.

In certain embodiments, the instant disclosure provides an isolated antibody that specifically binds to TIGIT (e.g., human TIGIT or cynomolgus TIGIT), the antibody comprising a light chain comprising the amino acid sequence set forth in SEQ ID NO: 13, 14, 15, or 21. In certain embodiments, the amino acid sequence of the light chain consists of an amino acid sequence selected from the group consisting of SEQ ID NO: 13, 14, 15, or 21.

In certain embodiments, the instant disclosure provides an isolated antibody that specifically binds to TIGIT (e.g., human TIGIT or cynomolgus TIGIT), comprising the heavy chain and light chain, wherein the heavy chain and light chain comprise the amino acid sequences of SEQ ID NOs: 11 and 13; 11 and 14; 11 and 15; 11 and 21; 12 and 13; 12 and 14; 12 and 15; 12 and 21; 19 and 13; 19 and 14; 19 and 15; 19 and 21; 20 and 13; 20 and 14; 20 and 15; or 20 and 21, respectively.

In certain embodiments, the amino acid sequences of the heavy chain and light chain consist of amino acid sequences selected from the groups consisting of SEQ ID NOs: 11 and 13; 11 and 14; 11 and 15; 11 and 21; 12 and 13; 12 and 14;

12 and 15; 12 and 21; 19 and 13; 19 and 14; 19 and 15; 19 and 21; 20 and 13; 20 and 14; 20 and 15; or 20 and 21, respectively.

In certain embodiments, the antibody disclosed herein is conjugated to a cytotoxic agent, cytostatic agent, toxin, radionuclide, or detectable label. In certain embodiments, the cytotoxic agent is able to induce death or destruction of a cell in contact therewith. In certain embodiments, the cytostatic agent is able to prevent or substantially reduce proliferation and/or inhibits the activity or function of a cell in contact therewith. In certain embodiments, the cytotoxic agent or cytostatic agent is a chemotherapeutic agent. In certain embodiments, the radionuclide is selected from the group consisting of the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac, and $^{186}$Re. In certain embodiments, the detectable label comprises a fluorescent moiety or a click chemistry handle.

Any immunoglobulin (Ig) constant region can be used in the antibodies disclosed herein. In certain embodiments, the Ig region is a human IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_2$a and $IgG_2$b) of immunoglobulin molecule.

In certain embodiments, the instant disclosure provides an isolated antibody that specifically binds to TIGIT (e.g., human TIGIT or cynomolgus TIGIT), the antibody comprising a heavy chain constant region comprising the amino acid sequence of SEQ ID NO: 16 or 22. In certain embodiments, the instant disclosure provides an isolated antibody that specifically binds to TIGIT (e.g., human TIGIT or cynomolgus TIGIT), the antibody comprising a light chain constant region comprising the amino acid sequence of SEQ ID NO: 17 or 18.

In certain embodiments, one, two, or more mutations (e.g., amino acid substitutions) are introduced into an Fc region (e.g., a CH2 domain (residues 231-340 of human $IgG_1$) and/or a CH3 domain (residues 341-447 of human $IgG_1$), numbered according to the EU numbering system) and/or a hinge region (residues 216-230, numbered according to the EU numbering system) of an antibody described herein, to alter one or more functional properties of the antibody, such as serum half-life, complement fixation, Fc receptor binding, and/or antigen-dependent cellular cytotoxicity.

In certain embodiments, one, two, or more mutations (e.g., amino acid substitutions) are introduced into the hinge region of an antibody described herein, such that the number of cysteine residues in the hinge region is altered (e.g., increased or decreased) as described in, e.g., U.S. Pat. No. 5,677,425, herein incorporated by reference in its entirety. The number of cysteine residues in the hinge region may be altered to, e.g., facilitate assembly of the light and heavy chains, or to alter (e.g., increase or decrease) the stability of the antibody.

In a specific embodiment, one, two, or more amino acid mutations (e.g., substitutions, insertions, or deletions) are introduced into an IgG constant region, or FcRn-binding fragment thereof (preferably an Fc or hinge-Fc fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375, and 6,165,745, all of which are herein incorporated by reference in their entireties, for examples of mutations that will alter (e.g., decrease or increase) the half-life of an antibody in vivo. In certain embodiments, one, two or more amino acid mutations (e.g., substitutions, insertions, or deletions) are introduced into an IgG constant region, or FcRn-binding fragment thereof (preferably an Fc or hinge-Fc fragment) to decrease the half-life of the antibody in vivo. In other embodiments, one, two or more amino acid mutations (e.g., substitutions, insertions, or deletions) are introduced into an IgG constant region, or FcRn-binding fragment thereof (preferably an Fc or hinge-Fc fragment) to increase the half-life of the antibody in vivo. In a specific embodiment, the antibodies may have one or more amino acid mutations (e.g., substitutions) in the second constant (CH2) domain (residues 231-340 of human $IgG_1$) and/or the third constant (CH3) domain (residues 341-447 of human $IgG_1$), numbered according to the EU numbering system. In a specific embodiment, the constant region of the $IgG_1$ of antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant IgG, referred to as "YTE mutant" has been shown to display fourfold increased half-life as compared to wild-type versions of the same antibody (see Dall'Acqua W F et al., (2006) J Biol Chem 281: 23514-24, which is herein incorporated by reference in its entirety). In certain embodiments, an antibody comprises an IgG constant region comprising one, two, three, or more amino acid substitutions of amino acid residues at positions 251-257, 285-290, 308-314, 385-389, and 428-436, numbered according to the EU numbering system.

In certain embodiments, one, two, or more mutations (e.g., amino acid substitutions) are introduced into an Fc region (e.g., a CH2 domain (residues 231-340 of human $IgG_1$) and/or a CH3 domain (residues 341-447 of human $IgG_1$), numbered according to the EU numbering system) and/or a hinge region (residues 216-230, numbered according to the EU numbering system) of an antibody described herein, to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186; U.S. Pat. No. 6,737,056; and International Publication Nos. WO 02/060919; WO 98/23289; and WO 97/34631, all of which are herein incorporated by reference in their entireties.

In certain embodiments, the antibody comprises a heavy chain constant region that is a variant of a wild type heavy chain constant region, wherein the variant heavy chain constant region binds to FcγRIIB with higher affinity than the wild type heavy chain constant region binds to FcγRIIB In certain embodiments, the variant heavy chain constant region is a variant human heavy chain constant region, e.g., a variant human $IgG_1$, a variant human $IgG_2$, or a variant human $IgG_4$ heavy chain constant region. In certain embodiments, the variant human IgG heavy chain constant region comprises one or more of the following amino acid mutations, according to the EU numbering system: G236D, P238D, S239D, S267E, L328F, and L328E. In certain embodiments, the variant human IgG heavy chain constant region comprises a set of amino acid mutations selected from the group consisting of: S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F, according to the EU numbering system. In certain embodiments, the FcγRIIB is expressed on a cell selected from the group consisting of macrophages, monocytes, B cells, dendritic cells, endothelial cells, and activated T cells.

In a further embodiment, one, two, or more amino acid substitutions are introduced into an IgG constant region Fc region to alter the effector function(s) of the antibody. For example, one or more amino acids selected from amino acid residues 234, 235, 236, 237, 239, 243, 267, 292, 297, 300, 318, 320, 322, 328, 330, 332, and 396, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In certain embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant region and thereby increase tumor localization. In certain embodiments, one or more amino acid substitutions may be introduced into the Fc region of an antibody described herein to remove potential glycosylation sites on the Fc region, which may reduce Fc receptor binding (see, e.g., Shields R L et al., (2001) J Biol Chem 276: 6591-604, which is herein incorporated by reference in its entirety). In various embodiments, one or more of the following mutations in the constant region of an antibody described herein may be made: an N297A substitution; an N297Q substitution; an L234A substitution; an L234F substitution; an L235A substitution; an L235F substitution; an L235V substitution; an L237A substitution; an S239D substitution; an E233P substitution; an L234V substitution; an L235A substitution; a C236 deletion; a P238A substitution; an S239D substitution; an F243L substitution; a D265A substitution; an S267E substitution; an L328F substitution; an R292P substitution; a Y300L substitution; an A327Q substitution; a P329A substitution; an A330L substitution; an I332E substitution; or a P396L substitution, numbered according to the EU numbering system.

In certain embodiments, a mutation selected from the group consisting of D265A, P329A, and a combination thereof, numbered according to the EU numbering system, may be made in the constant region of an antibody described herein. In certain embodiments, a mutation selected from the group consisting of L235A, L237A, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein. In certain embodiments, a mutation selected from the group consisting of S239D, I332E, optionally A330L, and a combination thereof, numbered according to the EU numbering system, may be made in the constant region of an antibody described herein. In certain embodiments, a mutation selected from the group consisting of L235V, F243L, R292P, Y300L, P396L, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein.

In a specific embodiment, an antibody described herein comprises the constant region of an IgG$_1$ with an N297Q or N297A amino acid substitution, numbered according to the EU numbering system. In certain embodiments, an antibody described herein comprises the constant region of an IgG$_1$ with a mutation selected from the group consisting of D265A, P329A, and a combination thereof, numbered according to the EU numbering system. In another embodiment, an antibody described herein comprises the constant region of an IgG$_1$ with a mutation selected from the group consisting of L234A, L235A, and a combination thereof, numbered according to the EU numbering system. In another embodiment, an antibody described herein comprises the constant region of an IgG$_1$ with a mutation selected from the group consisting of L234F, L235F, N297A, and a combination thereof, numbered according to the EU numbering system. In certain embodiments, amino acid residues in the constant region of an antibody described herein in the positions corresponding to positions L234, L235, and D265 in a human IgG$_1$ heavy chain, numbered according to the EU numbering system, are not L, L, and D, respectively. This approach is described in detail in International Publication No. WO 14/108483, which is herein incorporated by reference in its entirety. In certain embodiments, the amino acids corresponding to positions L234, L235, and D265 in a human IgG$_1$ heavy chain are F, E, and A; or A, A, and A, respectively, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.), which is herein incorporated by reference in its entirety. In certain embodiments, one or more amino acid residues within amino acid positions 231 to 238 in the N-terminal region of the CH2 domain of an antibody described herein are altered to thereby alter the ability of the antibody to fix complement, numbered according to the EU numbering system. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In certain embodiments, an antibody described herein comprises a modified constant region of an IgG$_1$, wherein the modification increases the ability of the antibody to mediate antibody dependent cellular cytotoxicity (ADCC). In certain embodiments, 0.1, 1, or 10 μg/mL of the antibody is capable of inducing cell death of at least 20%, 25%, 30%, 35%, 40%, 45%, 50%, 55%, or 60% of TIGIT-expressing cells within 1, 2, or 3 hours, as assessed by methods described herein and/or known to a person of skill in the art. In certain embodiments, the modified constant region of an IgG$_1$ comprises S239D and I332E substitutions, numbered according to the EU numbering system. In certain embodiments, the modified constant region of an IgG$_1$ comprises S239D, A330L, and I332E substitutions, numbered according to the EU numbering system. In certain embodiments, the modified constant region of an IgG$_1$ comprises L235V, F243L, R292P, Y300L, and P396L substitutions, numbered according to the EU numbering system. In certain embodiments, the antibody is capable of inducing cell death in effector T cells and Tregs, wherein the percentage of Tregs that undergo cell death is higher than the percentage of effector T cells that undergo cell death by at least 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, or 5 fold.

In certain embodiments, an antibody described herein comprises the constant region of an IgG$_4$ antibody and the serine at amino acid residue 228 of the heavy chain, numbered according to the EU numbering system, is substituted for proline. In certain embodiments, the instant disclosure provides an isolated antibody that specifically binds to TIGIT (e.g., human TIGIT or cynomolgus TIGIT), the antibody comprising a heavy chain constant region comprising the amino acid sequence of SEQ ID NO: 16 or 22.

In certain embodiments, any of the constant region mutations or modifications described herein can be introduced into one or both heavy chain constant regions of an antibody described herein having two heavy chain constant regions.

In certain embodiments, the instant disclosure provides an isolated antibody that specifically binds to TIGIT (e.g., human TIGIT or cynomolgus TIGIT) and functions as an antagonist (e.g., decreases or inhibits TIGIT activity).

In certain embodiments, the instant disclosure provides an isolated antibody that specifically binds to TIGIT (e.g., human TIGIT or cynomolgus TIGIT) and decreases or inhibits TIGIT (e.g., human TIGIT or cynomolgus TIGIT) activity by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein and/or known to one of skill in the art, relative to TIGIT (e.g., human TIGIT or cynomolgus TIGIT) activity without any antibody or with an unrelated antibody (e.g., an antibody that does not specifically bind to TIGIT (e.g., human TIGIT or cynomolgus TIGIT)). In certain embodiments, the instant disclosure provides an isolated antibody that specifically binds to TIGIT (e.g., human TIGIT or cynomolgus TIGIT) and decreases or inhibits TIGIT (e.g., human TIGIT or cynomolgus TIGIT) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, or more, as assessed by methods described herein and/or known to one of skill in the art, relative to TIGIT (e.g., human TIGIT or cynomolgus TIGIT) activity without any antibody or with an unrelated antibody (e.g., an antibody that does not specifically bind to TIGIT (e.g., human TIGIT or cynomolgus TIGIT)). Non-limiting examples of TIGIT (e.g., human TIGIT or cynomolgus TIGIT) activity can include TIGIT (e.g., human TIGIT or cynomolgus TIGIT) signaling; TIGIT (e.g., human TIGIT or cynomolgus TIGIT) binding to its ligand ((e.g., CD155) or a fragment and/or fusion protein thereof); activation of a T cell (e.g., a T cell expressing human TIGIT); activation of a natural killer (NK) cell; decrease or inhibition of a Treg; increase of cytokine (e.g., IL-2) production; increase of the activity of CD155 (e.g., human CD155). In specific embodiments, an increase in a TIGIT (e.g., human TIGIT or cynomolgus TIGIT) activity is assessed as described in the Examples.

In specific embodiments, the instant disclosure provides an isolated antibody that specifically binds TIGIT (e.g., human TIGIT or cynomolgus TIGIT) and decreases or inhibits TIGIT (e.g., human TIGIT or cynomolgus TIGIT) binding to its ligand ((e.g., CD155) or a fragment and/or fusion protein thereof) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to TIGIT (e.g., human TIGIT or cynomolgus TIGIT) binding to this ligand without any antibody or with an unrelated antibody (e.g., an antibody that does not specifically bind to TIGIT (e.g., human TIGIT or cynomolgus TIGIT)). In specific embodiments, the instant disclosure provides an isolated antibody that specifically binds to TIGIT (e.g., human TIGIT or cynomolgus TIGIT) and increases TIGIT (e.g., human TIGIT or cynomolgus TIGIT) binding to its ligand (e.g., CD155 (e.g., human or cynomolgus CD155) or a fragment and/or fusion protein thereof) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to TIGIT (e.g., human TIGIT) binding to this ligand without any antibody or with an unrelated antibody (e.g., an antibody that does not specifically bind to TIGIT (e.g., human TIGIT or cynomolgus TIGIT)).

In specific embodiments, the instant disclosure provides an isolated antibody that specifically binds to TIGIT (e.g., human TIGIT or cynomolgus TIGIT) and activates a T cell (e.g., a T cell expressing human TIGIT). In certain embodiments, the T cell is a memory T cell. In certain embodiments, the T cell is a primary CD3-expressing T cell. In certain embodiments, the T cell is a TIGIT-expressing Jurkat cell. In certain embodiments, the antibody disclosed herein increases the activity of nuclear factor of activated T cells (NFAT) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to NFAT activity without any antibody or with an unrelated antibody (e.g., an antibody that does not specifically bind to TIGIT (e.g., human TIGIT or cynomolgus TIGIT)). In certain embodiments, the antibody disclosed herein increases the activity of NFAT by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to NFAT activity without any antibody or with an unrelated antibody (e.g., an antibody that does not specifically bind to TIGIT (e.g., human TIGIT or cynomolgus TIGIT)). In certain embodiments, the antibody increases NFAT activity in the presence of a ligand of TIGIT (e.g., CD155) or a fragment and/or fusion protein thereof, and/or a cell expressing a ligand of TIGIT (e.g., a monocyte or a dendritic cell).

In specific embodiments, the instant disclosure provides an isolated antibody that specifically binds to TIGIT (e.g., human TIGIT or cynomolgus TIGIT) and increases cytokine production (e.g., IL-2) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to cytokine production without any antibody or with an unrelated antibody (e.g., an antibody that does not specifically bind to TIGIT (e.g., human TIGIT or cynomolgus TIGIT)). In specific embodiments, the instant disclosure provides an isolated antibody that specifically binds to TIGIT (e.g., human TIGIT or cynomolgus TIGIT) and increases cytokine production (e.g., IL-2) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to cytokine production without any antibody or with an unrelated antibody (e.g., an antibody that does not specifically bind to TIGIT (e.g., human TIGIT or cynomolgus TIGIT)). In certain embodiments, the antibody increases cytokine production (e.g., IL-2) in the presence of a ligand of TIGIT ((e.g., CD155) or a fragment and/or fusion protein thereof), and/or a cell expressing a ligand of TIGIT (e.g., a monocyte or a dendritic cell). In certain embodiments, the antibody increases the production of IL-2 relative to IL-2 production without any antibody or with an unrelated antibody (e.g., an antibody that does not specifically bind to TIGIT (e.g., human TIGIT or cynomolgus TIGIT)).

In certain embodiments, the instant disclosure provides an isolated antibody that specifically binds to TIGIT (e.g., human TIGIT or cynomolgus TIGIT) and which either alone or in combination with an anti-PD-1 antibody (e.g., pembrolizumab or nivolumab), increases IFNγ and/or IL-2 production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to IFNγ and/or IL-2 production without any antibody or with an unrelated antibody (e.g., an antibody that does not specifically bind to TIGIT (e.g., human TIGIT or cynomolgus TIGIT)).

In certain embodiments, human peripheral blood mononuclear cells (PBMCs) stimulated with *Staphylococcus* Enterotoxin A (SEA) in the presence of an antibody described herein, which specifically binds to TIGIT (e.g., human TIGIT or cynomolgus TIGIT), have increased IFNγ and/or IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, relative to IFNγ and/or IL-2 production from PBMCs only stimulated with SEA without any antibody or with an unrelated antibody (e.g., an antibody that does not specifically bind to TIGIT (e.g., human TIGIT or cynomolgus TIGIT)), as assessed by methods described herein or known to one of skill in the art.

In certain embodiments, the instant disclosure provides an isolated antibody that specifically binds to TIGIT (e.g., human TIGIT or cynomolgus TIGIT) and increases or promotes memory recall of a memory T cell. In certain embodiments, the memory T cell is a CD8 effector memory T cell. In certain embodiments, the memory T cell is a CD4 effector memory T cell. In certain embodiments, the antibody increases the number of proliferating memory T cells when the memory T cells are in contact with their cognate antigen(s) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to the number of proliferating memory T cells when the memory T cells are in contact with their cognate antigen(s) in the absence of any antibody or in the presence of an unrelated antibody (e.g., an antibody that does not specifically bind to TIGIT (e.g., human TIGIT or cynomolgus TIGIT)). In certain embodiments, the antibody increases the production of a cytokine (e.g., IFNγ, TNFα) from a memory T cell when the memory T cell is in contact with its cognate antigen by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein or known to one of skill in the art, relative to the production of the cytokine from a memory T cell when the memory T cell is in contact with its cognate antigen in the absence of any antibody or in the presence of an unrelated antibody (e.g., an antibody that does not specifically bind to TIGIT (e.g., human TIGIT or cynomolgus TIGIT)).

In certain embodiments, the instant disclosure provides an isolated antibody that specifically binds to TIGIT (e.g., human TIGIT or cynomolgus TIGIT) and activates an NK cell. In certain embodiments, the NK cells are isolated. In certain embodiments, the NK cells are in a mixed culture of PBMCs. In certain embodiments, the antibody disclosed herein increases the expression level of CD107a in NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to the expression level of CD107a in NK cells without any antibody or with an unrelated antibody (e.g., an antibody that does not specifically bind to TIGIT (e.g., human TIGIT or cynomolgus TIGIT)). In certain embodiments, the antibody disclosed herein increases the expression level of CD107a in NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to the expression level of CD107a in NK cells without any antibody or with an unrelated antibody (e.g., an antibody that does not specifically bind to TIGIT (e.g., human TIGIT or cynomolgus TIGIT)). In certain embodiments, the antibody disclosed herein increases cytokine production (e.g., IFNγ and/or TNFα) from NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein or known to one of skill in the art, relative to cytokine production (e.g., IFNγ and/or TNFα)

from NK cells without any antibody or with an unrelated antibody (e.g., an antibody that does not specifically bind to TIGIT (e.g., human TIGIT or cynomolgus TIGIT)). In certain embodiments, the antibody disclosed herein increases cytokine production (e.g., IFNγ and/or TNFα) from NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein or known to one of skill in the art, relative to cytokine production (e.g., IFNγ and/or TNFα) from NK cells without any antibody or with an unrelated antibody (e.g., an antibody that does not specifically bind to TIGIT (e.g., human TIGIT or cynomolgus TIGIT)).

7.3 Pharmaceutical Compositions

Provided herein are compositions comprising an isolated anti-TIGIT antibody disclosed herein having the desired degree of purity in a physiologically acceptable carrier, excipient, or stabilizer (see, e.g., Remington's Pharmaceutical Sciences (1990) Mack Publishing Co., Easton, PA). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose, or sorbitol; salt-forming counter-ions such as sodium; metal complexes (e.g., Zn-protein complexes); and/or non-ionic surfactants such as TWEEN™, PLURONIC™ or polyethylene glycol (PEG).

In a specific embodiment, pharmaceutical compositions comprise an isolated anti-TIGIT antibody disclosed herein, and optionally one or more additional prophylactic or therapeutic agents, in a pharmaceutically acceptable carrier. In a specific embodiment, pharmaceutical compositions comprise an isolated anti-TIGIT antibody herein, and optionally one or more additional prophylactic or therapeutic agents, in a pharmaceutically acceptable carrier. In certain embodiments, the antibody is the only active ingredient included in the pharmaceutical composition. Pharmaceutical compositions described herein can be useful in increasing or promoting TIGIT (e.g., human TIGIT or cynomolgus TIGIT) activity and treating a condition, such as cancer or an infectious disease. In certain embodiments, the present invention relates to a pharmaceutical composition of the present invention comprising an isolated anti-TIGIT antibody of the present invention for use as a medicament. In another embodiment, the present invention relates to a pharmaceutical composition of the present invention for use in a method for the treatment of cancer or an infectious disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering, or chelating agents and other pharmaceutically acceptable substances. Examples of aqueous vehicles include Sodium Chloride Injection, Ringer's Injection, Isotonic Dextrose Injection, Sterile Water Injection, Dextrose and Lactated Ringer's Injection. Nonaqueous parenteral vehicles include fixed oils of vegetable origin, cottonseed oil, corn oil, sesame oil, and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride, and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose, and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol, and propylene glycol for water miscible vehicles; and sodium hydroxide, hydrochloric acid, citric acid, or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular, or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol, or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate, and cyclodextrins.

Preparations for parenteral administration of antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsion or the like and can be formulated as creams, gels, ointments, emulsions, solutions, elixirs, lotions, suspensions, tinctures, pastes, foams, aerosols, irrigations, sprays, suppositories, bandages, dermal patches, or any other formulations suitable for topical administration.

An isolated anti-TIGIT antibody disclosed herein can be formulated as an aerosol for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma and are herein incorporated by reference in their entireties). These formulations for administration to the respiratory tract can be in the form of an aerosol or solution for a nebulizer, or as a microtine powder for insufflations, alone or in combination with an inert carrier such as lactose. In such a case, the particles of the formulation will, in certain embodiments, have diameters of less than 50 microns, in certain embodiments less than 10 microns.

An isolated anti-TIGIT antibody disclosed herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, all of which are herein incorporated by reference in their entireties.

In certain embodiments, a pharmaceutical composition comprising antibody described herein is a lyophilized powder, which can be reconstituted for administration as solutions, emulsions, and other mixtures. It may also be reconstituted and formulated as solids or gels. The lyophilized powder is prepared by dissolving antibody described herein, or a pharmaceutically acceptable derivative thereof, in a suitable solvent. In certain embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose, or other suitable agent. The solvent may also contain a buffer, such as citrate, sodium or potassium phosphate or other such buffer known to those of skill in the art at, In certain embodiments, about neutral pH. Subsequent sterile filtration of the solution followed by lyophilization under standard conditions known to those of skill in the art provides the desired formulation. In certain embodiments, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The isolated anti-TIGIT antibodies disclosed herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542, and 5,709,874, all of which are herein incorporated by reference in their entireties. In a specific embodiment, an antibody described herein is targeted to a tumor.

The compositions to be used for in vivo administration can be sterile. This is readily accomplished by filtration through, e.g., sterile filtration membranes.

7.4 Methods of Use and Uses

In another aspect, the instant disclosure provides a method of treating a subject using the anti-TIGIT antibodies disclosed herein. Any disease or disorder in a subject that would benefit from decrease of TIGIT (e.g., human TIGIT or cynomolgus TIGIT) function can be treated using the isolated anti-TIGIT antibodies disclosed herein. In certain embodiments, the disease or disorder is resistant to a checkpoint targeting agent (e.g., an antagonist anti-CTLA-4 antibody, an antagonist anti-PD-L1 antibody, an antagonist anti-PD-L2 antibody, or an antagonist anti-PD-1 antibody). In certain embodiments, the disease or disorder is recurrent after treatment with a checkpoint targeting agent (e.g., an antagonist anti-CTLA-4 antibody, an antagonist anti-PD-L1 antibody, an antagonist anti-PD-L2 antibody, or an antagonist anti-PD-1 antibody).

The isolated anti-TIGIT antibodies disclosed herein are particularly useful for inhibiting immune system tolerance to tumors, and accordingly can be used as an immunotherapy for subjects with cancer. For example, in certain embodiments, the instant disclosure provides a method of increasing T cell (e.g., CD8$^+$ cytotoxic T cells, CD4$^+$ helper T cells, NKT cells, effector T cells, or memory T cells) activation in response to an antigen in a subject, the method comprising administering to the subject an effective amount of an isolated anti-TIGIT antibody or pharmaceutical composition thereof as disclosed herein. In certain embodiments, the instant disclosure provides a method of treating cancer in a subject, the method comprising administering to the subject an effective amount of the antibody or pharmaceutical composition, as disclosed herein.

Cancers that can be treated with the isolated anti-TIGIT antibodies or pharmaceutical compositions disclosed herein include, without limitation, a solid tumor, a hematological cancer (e.g., leukemia, lymphoma, myeloma, e.g., multiple myeloma), and a metastatic lesion. In certain embodiments, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, lung cancer (e.g., non-small cell lung cancer or small cell lung cancer), cancer of the small intestine and cancer of the esophagus. The cancer may be at an early, intermediate, late stage or metastatic cancer. In certain embodiments, the cancer is resistant to a checkpoint targeting agent (e.g., an antagonist anti-CTLA-4 antibody, an antagonist anti-PD-L1 antibody, an antagonist anti-PD-L2 antibody, or an antagonist anti-PD-1 antibody). In certain embodiments, the cancer is recurrent after treatment with a checkpoint targeting agent (e.g., an antagonist anti-CTLA-4 antibody, an antagonist anti-PD-L1 antibody, an antagonist anti-PD-L2 antibody, or an antagonist anti-PD-1 antibody).

In certain embodiments, the cancer is chosen from lung cancer (e.g., lung adenocarcinoma or non-small cell lung cancer (NSCLC) (e.g., NSCLC with squamous and/or non-squamous histology, or NSCLC adenocarcinoma)), melanoma (e.g., an advanced melanoma), renal cancer (e.g., a renal cell carcinoma), liver cancer (e.g., hepatocellular carcinoma), myeloma (e.g., a multiple myeloma), a prostate cancer, a breast cancer (e.g., a breast cancer that does not express one, two, or all of estrogen receptor, progesterone receptor, or Her2/neu, e.g., a triple negative breast cancer), an ovarian cancer, a colorectal cancer, a pancreatic cancer, a head and neck cancer (e.g., head and neck squamous cell carcinoma (HNSCC)), anal cancer, gastro-esophageal cancer (e.g., esophageal squamous cell carcinoma), mesothelioma, nasopharyngeal cancer, thyroid cancer, cervical cancer, epithelial cancer, peritoneal cancer, or a lymphoproliferative disease (e.g., a post-transplant lymphoproliferative disease). In a specific embodiment, the cancer is a cervical cancer.

In certain embodiments, the cancer is a hematological cancer, for example, a leukemia, a lymphoma, or a myeloma. In certain embodiments, the cancer is a leukemia, for example, acute lymphoblastic leukemia (ALL), acute myelogenous leukemia (AML), acute myeloblastic leukemia (AML), chronic lymphocytic leukemia (CLL), chronic myelogenous leukemia (CML), chronic myeloid leukemia (CML), chronic myelomonocytic leukemia (CMML), chronic lymphocytic leukemia (CLL), or hairy cell leukemia. In certain embodiments, the cancer is a lymphoma, for example, B cell lymphoma, diffuse large B cell lymphoma (DLBCL), activated B cell like (ABC) diffuse large B cell lymphoma, germinal center B cell (GCB) diffuse large B cell lymphoma, mantle cell lymphoma, Hodgkin lymphoma, non-Hodgkin lymphoma, relapsed non-Hodgkin lymphoma, refractory non-Hodgkin lymphoma, recurrent follicular non-Hodgkin lymphoma, Burkitt lymphoma, small lymphocytic lymphoma, follicular lymphoma, lymphoplasmacytic lymphoma, or extranodal marginal zone lymphoma. In certain embodiments the cancer is a myeloma, for example, multiple myeloma.

In another embodiment, the cancer is chosen from a carcinoma (e.g., advanced or metastatic carcinoma), melanoma or a lung carcinoma, e.g., a non-small cell lung carcinoma.

In certain embodiments, the cancer is a lung cancer, e.g., a lung adenocarcinoma, non-small cell lung cancer, or small cell lung cancer.

In certain embodiments, the cancer is a melanoma, e.g., an advanced melanoma. In certain embodiments, the cancer is an advanced or unresectable melanoma that does not respond to other therapies. In other embodiments, the cancer is a melanoma with a BRAF mutation (e.g., a BRAF V600 mutation). In yet other embodiments, the isolated anti-TIGIT antibodies or pharmaceutical composition disclosed herein is administered after treatment with an anti-CTLA-4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC, clear cell renal cell carcinoma (CCRCC), or kidney papillary cell carcinoma).

In yet another embodiment, the cancer is chosen from a lung cancer, a melanoma, a renal cancer, a breast cancer, a colorectal cancer, a leukemia, or a metastatic lesion of the cancer.

In certain embodiments, the instant disclosure provides a method of preventing or treating an infectious disease in a subject, the method comprising administering to the subject an effective amount of an isolated anti-TIGIT antibody, or pharmaceutical composition thereof, as disclosed herein. In certain embodiments, provided herein are methods for preventing and/or treating an infection (e.g., a viral infection, a bacterial infection, a fungal infection, a protozoal infection, or a parasitic infection). The infection prevented and/or treated in accordance with the methods can be caused by an infectious agent identified herein. In a specific embodiment, an isolated anti-TIGIT antibody described herein or a composition thereof is the only active agent administered to a subject. In certain embodiments, an isolated anti-TIGIT antibody described herein or a composition thereof is used in combination with anti-infective interventions (e.g., antivirals, antibacterials, antifungals, or anti-helminthics) for the treatment of infectious diseases. Therefore, in one embodiment, the present invention relates to an antibody and/or pharmaceutical composition of the present invention for use in a method of preventing and/or treating an infectious disease, optionally wherein the antibody or pharmaceutical composition is the only active agent administered to a subject, or wherein the antibody or pharmaceutical composition is used in combination with anti-infective interventions.

Infectious diseases that can be treated and/or prevented by isolated anti-TIGIT antibodies or pharmaceutical compositions disclosed herein are caused by infectious agents, including but not limited to bacteria, parasites, fungi, protozoae, and viruses. In a specific embodiment, the infectious disease treated and/or prevented by isolated anti-TIGIT antibodies or pharmaceutical compositions disclosed herein is caused by a virus. Viral diseases or viral infections that can be prevented and/or treated in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus, polio virus, small pox, Epstein-Barr virus, human immunodeficiency virus type I (HIV-I), human immunodeficiency virus type II (HIV-II), and agents of viral diseases such as viral meningitis, encephalitis, dengue, or small pox.

Bacterial infections that can be prevented and/or treated include infections caused by *Escherichia coli, Klebsiella pneumoniae, Staphylococcus aureus, Enterococcus faecalis, Proteus vulgaris, Staphylococcus viridans*, and *Pseudomonas aeruginosa*. Bacterial diseases caused by bacteria (e.g., *Escherichia coli, Klebsiella pneumoniae, Staphylococcus aureus, Enterococcus faecalis, Proteus vulgaris, Staphylococcus viridans*, and *Pseudomonas aeruginosa*) that can be prevented and/or treated in accordance with the methods described herein include, but are not limited to, *Mycobacteria rickettsia, Mycoplasma, Neisseria, S. pneumonia, Borrelia burgdorferi* (Lyme disease), *Bacillus anthracis* (anthrax), tetanus, *Streptococcus, Staphylococcus, mycobacterium*, pertussis, cholera, plague, diphtheria, chlamydia, *S. aureus*, and legionella.

Protozoal diseases or protozoal infections caused by protozoa that can be prevented and/or treated in accordance with the methods described herein include, but are not limited to, leishmania, coccidiosis, trypanosoma, schistosoma, or malaria. Parasitic diseases or parasitic infections caused by parasites that can be prevented and/or treated in accordance with the methods described herein include, but are not limited to, chlamydia and rickettsia.

Fungal diseases or fungal infections that can be prevented and/or treated in accordance with the methods described herein include, but are not limited to, those caused by *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium* keratitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis.

In certain embodiments, these methods further comprise administering an additional therapeutic agent to the subject. In certain embodiments, the additional therapeutic agent is a chemotherapeutic, a radiotherapeutic, or a checkpoint targeting agent. In certain embodiments, the chemotherapeutic agent is a hypomethylating agent (e.g., azacitidine). In certain embodiments, the chemotherapeutic agent is a DNA damage-inducing agent (e.g., gemcitabine). In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-VISTA antibody, an antagonist anti-CD96 antibody, an antagonist anti-CEACAM1 antibody, an agonist anti-CD137 antibody, an agonist anti-GITR antibody, and an agonist anti-OX40 antibody. In certain embodiments, the checkpoint targeting agent is selected from the group consisting of an antagonist anti-CTLA-4 antibody, an antagonist anti-PD-L1 antibody, an antagonist anti-PD-L2 antibody, and an antagonist anti-PD-1 antibody, wherein the TIGIT (e.g., human TIGIT or cynomolgus TIGIT) antibodies or pharmaceutical compositions disclosed herein synergize with the checkpoint targeting agent.

In certain embodiments, the present invention relates to an antibody and/or pharmaceutical composition of the present invention for use in a method of the present invention, wherein the method further comprises administering an additional therapeutic agent to the subject. In certain embodiments, the present invention relates to (a) an antibody and/or pharmaceutical composition of the present invention, and (b) an additional therapeutic agent for use as a medicament. In certain embodiments, the present invention relates to (a) an antibody and/or pharmaceutical composition of the present invention, and (b) an additional therapeutic agent for use in a method for the treatment of cancer. In a further embodiment, the present invention relates to a pharmaceutical composition, kit or kit-of-parts comprising (a) an antibody and/or pharmaceutical composition of the present invention, and (b) an additional therapeutic agent. In certain embodiments, the additional therapeutic agent is a chemotherapeutic, a radiotherapeutic, or a checkpoint targeting agent.

In certain embodiments, an anti-PD-1 antibody is used in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by MedImmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, all of which are herein incorporated by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene, and MedImmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, all of which are herein incorporated by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, an anti-CTLA-4 antibody is used in methods disclosed herein. In certain embodiments, the anti-CTLA-4 antibody is ipilimumab developed by Bristol-Myers Squibb.

In certain embodiments, an isolated anti-TIGIT antibody disclosed herein is administered to a subject in combination with a compound that targets an immunomodulatory enzyme (s) such as IDO (indoleamine-(2,3)-dioxygenase) and/or TDO (tryptophan 2,3-dioxygenase). Therefore, in certain embodiments, the additional therapeutic agent is a compound that targets an immunomodulatory enzyme(s), such as an inhibitor of indoleamine-(2,3)-dioxygenase (IDO). In certain embodiments, such compound is selected from the group consisting of epacadostat (Incyte Corp; see, e.g., WO 2010/005958 which is herein incorporated by reference in its entirety), F001287 (Flexus Biosciences/Bristol-Myers Squibb), indoximod (NewLink Genetics), and NLG919 (NewLink Genetics). In certain embodiments, the compound is epacadostat. In another embodiment, the compound is F001287. In another embodiment, the compound is indoximod. In another embodiment, the compound is NLG919. In a specific embodiment, an isolated anti-TIGIT antibody disclosed herein is administered to a subject in combination with an IDO inhibitor for treating cancer. The IDO inhibitor as described herein for use in treating cancer is present in a solid dosage form of a pharmaceutical composition such as a tablet, a pill, or a capsule, wherein the pharmaceutical composition includes an IDO inhibitor and a pharmaceutically acceptable excipient. As such, the antibody as described herein and the IDO inhibitor as described herein can be administered separately, sequentially, or concurrently as separate dosage forms. In certain embodiments, the antibody is administered parenterally, and the IDO inhibitor is administered orally. In certain embodiments, the inhibitor is selected from the group consisting of epacadostat (Incyte Corporation), F001287 (*Flexus* Biosciences/Bristol-Myers Squibb), indoximod (NewLink Genetics), and NLG919 (NewLink Genetics). Epacadostat has been described in PCT Publication No. WO 2010/005958, which is herein incorporated by reference in its entirety for all purposes. In certain embodiments, the inhibitor is epacadostat. In another embodiment, the inhibitor is F001287. In another embodiment, the inhibitor is indoximod. In another embodiment, the inhibitor is NLG919.

In certain embodiments, an isolated anti-TIGIT antibody disclosed herein is administered to a subject in combination with a vaccine. The vaccine can be, e.g., a peptide vaccine, a DNA vaccine, or an RNA vaccine. In certain embodiments, the vaccine is a heat shock protein-based tumor vaccine or a heat shock protein-based pathogen vaccine. In a specific embodiment, an isolated anti-TIGIT antibody disclosed herein is administered to a subject in combination with a heat shock protein-based tumor vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress, or glucose deprivation. Five families have been classified according to molecular weight: HSP-110, -90, -70, -60, and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject. Therefore, in certain embodiments, the present invention relates to (a) an antibody and/or pharmaceutical composition of the present invention and (b) a vaccine for use as a medicament, for example for use in a method for the treatment of cancer. In certain embodiments, the present invention relates to a pharmaceutical composition, kit or kit-of-parts comprising (a) an antibody and/or pharmaceutical composition of the present invention and (b) a vaccine. In certain embodiments, the vaccine is a heat shock protein-based tumor vaccine. In certain embodiments, the vaccine is a heat shock protein-based pathogen vaccine. In certain embodiments, the vaccine is as described in WO 2016/183486, incorporated herein by reference in its entirety.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to toll-like receptors. HSPPC internalization results in functional maturation of the APCs with chemokine and cytokine production leading to activation of natural killer cells (NK), monocytes and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, the heat shock protein peptide complex (HSPPC) comprises recombinant heat shock proteins (e.g., hsp70 or hsc70) or a peptide-binding region thereof complexed with recombinant antigenic peptides. Recombinant heat shock proteins can be produced by recombinant DNA technology, for example, using human hsc70 sequence as described in Dworniczak and Mirault, Nucleic Acids Res. 15:5181-5197 (1987) and GenBank accession no. P11142 and/or Y00371, each of which is incorporated herein by reference in its entirety. In certain embodiments, Hsp70 sequences are as described in Hunt and Morimoto Proc. Natl. Acad. Sci. U.S.A. 82 (19), 6455-6459 (1985) and GenBank accession no. PODMV8 and/or M11717, each of which is incorporated herein by reference in its entirety. Antigenic peptides can also be prepared by recombinant DNA methods known in the art.

In certain embodiments, the antigenic peptides comprise a modified amino acid. In certain embodiments, the modified amino acid comprises a post-translational modification. In certain embodiments, the modified amino acid comprises a mimetic of a post-translational modification. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser, Thr, Arg, Lys, or His amino acid that has been phosphorylated on a side chain hydroxyl or amine.

In a specific embodiment, an isolated anti-TIGIT antibody disclosed herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells, and injection of the vaccine is intended to stimulate the subject's immune system to recognize and attack any cells with the specific cancer fingerprint. Therefore, in certain embodiments, the present invention relates to an antibody and/or pharmaceutical composition of the present invention in combination with a heat shock protein peptide complex (HSPPC) for use as a medicament and/or for use in a method for the treatment of cancer.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In certain embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, all of which are herein incorporated by reference in their entireties: U.S. Pat. Nos. 6,391,306, 6,383,492, 6,403,095, 6,410,026, 6,436,404, 6,447,780, 6,447,781, and 6,610,659.

In certain embodiments, an isolated anti-TIGIT antibody disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), montanide ISA (incomplete Seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, 3 De-O-acylated monophosphoryl lipid A (3 D-MPL), immunostimulatory oligonucleotides, toll-like receptor (TLR) ligands, mannan-binding lectin (MBL) ligands, STING agonists, immunostimulating complexes such as saponins, Quil A, QS-21, QS-7, ISCOMATRIX, and others. Other adjuvants include CpG oligonucleotides and double stranded RNA molecules, such as poly(A) and poly(U). Combinations of the above adjuvants may also be used. See, e.g., U.S. Pat. Nos. 6,645,495; 7,029,678; and 7,858,589, all of which are incorporated herein by reference in their entireties. In certain embodiments, the adjuvant used herein is QS-21 STIMU-LON.

In certain embodiments, an isolated anti-TIGIT antibody disclosed herein is administered to a subject in combination with an additional therapeutic agent comprising a TCR. In certain embodiments, the additional therapeutic agent is a soluble TCR. In certain embodiments, the additional therapeutic agent is a cell expressing a TCR. Therefore, in certain embodiments, the present invention relates to an antibody and/or pharmaceutical composition of the present invention in combination with an additional therapeutic agent comprising a TCR for use as a medicament and/or for use in a method for the treatment of cancer.

In certain embodiments, an isolated anti-TIGIT antibody disclosed herein is administered to a subject in combination with a cell expressing a chimeric antigen receptor (CAR). In certain embodiments, the cell is a T cell.

In certain embodiments, an isolated anti-TIGIT antibody disclosed herein is administered to a subject in combination with a TCR mimic antibody. In certain embodiments, the TCR mimic antibody is an antibody that specifically binds to a peptide-MHC complex. For non-limiting examples of TCR mimic antibodies, see, e.g., U.S. Pat. No. 9,074,000 and U.S. Publication Nos. US 2009/0304679 A1 and US 2014/0134191 A1, all of which are incorporated herein by reference in their entireties.

In certain embodiments, an isolated anti-TIGIT antibody disclosed herein is administered to a subject in combination with a bispecific T-cell engager (BiTE) (e.g., as described in WO2005061547A2, which is incorporated by reference herein in its entirety) and/or a dual-affinity re-targeting antibody (DART) (e.g., as described in WO2012162067A2, which is incorporated by reference herein in its entirety). In certain embodiments, the BiTE and/or DART specifically binds to a tumor-associated antigen (e.g., a polypeptide overexpressed in a tumor, a polypeptide derived from an oncovirus, a polypeptide comprising a post-translational modification specific to a tumor, a polypeptide specifically mutated in a tumor) and a molecule on an effector cell (e.g., CD3 or CD16). In certain embodiments, the tumor-associated antigen is EGFR (e.g., human EGFR), optionally wherein the BiTE and/or DART comprises the VH and VL sequences of cetuximab. In certain embodiments, the tumor-associated antigen is Her2 (e.g., human Her2), optionally wherein the BiTE and/or DART comprises the VH and VL sequences of trastuzumab. In certain embodiments, the tumor-associated antigen is CD20 (e.g., human CD20).

The isolated anti-TIGIT antibody and the additional therapeutic agent (e.g., chemotherapeutic, radiotherapeutic, checkpoint targeting agent, IDO inhibitor, vaccine, adjuvant, a soluble TCR, a cell expressing a TCR, a cell expressing a chimeric antigen receptor, and/or a TCR mimic antibody) can be administered separately, sequentially, or concurrently as separate dosage forms. In certain embodiments, an isolated anti-TIGIT antibody is administered parenterally, and an IDO inhibitor is administered orally.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intra-arterial, and subcutaneous routes. Pulmonary administration can also be employed, e.g., by use of an inhaler or nebulizer, and formulation with an aerosolizing agent for use as a spray. In certain embodiments, the antibody or pharmaceutical composition described herein is delivered subcutaneously or intravenously. In certain embodiments, the antibody or pharmaceutical composition described herein is delivered intra-arterially. In certain embodiments, the antibody or pharmaceutical composition described herein is delivered intratumorally. In certain embodiments, the antibody or pharmaceutical composition described herein is delivered into a tumor draining lymph node.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, and health), whether the patient is human or an animal, other medications administered, or whether treatment is prophylactic or therapeutic. Usually, the patient is a human, but non-human mammals, including transgenic mammals, can also be treated. Treatment dosages are optimally titrated to optimize safety and efficacy.

An isolated anti-TIGIT antibody described herein can also be used to assay TIGIT (e.g., human TIGIT or cynomolgus TIGIT) protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an isolated anti-TIGIT antibody described herein can be labeled and used in combination with an isolated anti-TIGIT antibody to detect TIGIT (e.g., human TIGIT or cynomolgus TIGIT) protein levels. Therefore, in certain embodiments, the present invention relates to the use of an isolated anti-TIGIT antibody of the present invention for in vitro detection of TIGIT (e.g., human TIGIT or cynomolgus TIGIT) protein in a biological sample. In a further embodiment, the present invention relates to the use of an isolated anti-TIGIT antibody of the invention, for assaying and/or detecting TIGIT (e.g., human TIGIT or cynomolgus TIGIT) protein levels in a biological sample in vitro, optionally wherein the anti-TIGIT antibody is conjugated to a radio-nuclide or detectable label, and/or carries a label described herein, and/or wherein an immunohistological method is used.

Assaying for the expression level of TIGIT (e.g., human TIGIT or cynomolgus TIGIT) protein is intended to include qualitatively or quantitatively measuring or estimating the level of TIGIT (e.g., human TIGIT or cynomolgus TIGIT) protein in a first biological sample either directly (e.g., by determining or estimating absolute protein level) or relatively (e.g., by comparing to the disease associated protein level in a second biological sample). TIGIT (e.g., human TIGIT or cynomolgus TIGIT) polypeptide expression level in the first biological sample can be measured or estimated and compared to a standard TIGIT (e.g., human TIGIT or cynomolgus TIGIT) protein level, the standard being taken, for example, from a second biological sample obtained from an individual not having the disorder or being determined by averaging levels from a population of individuals not having the disorder. As will be appreciated in the art, once the "standard" TIGIT (e.g., human TIGIT or cynomolgus TIGIT) polypeptide level is known, it can be used repeatedly as a standard for comparison. Therefore, in a further embodiment, the present invention relates to an in vitro method for assaying and/or detecting TIGIT protein levels, for example human TIGIT protein levels, in a biological sample, comprising qualitatively or quantitatively measuring or estimating the level of TIGIT protein, for example of human TIGIT protein, in a biological sample, by an immunohistological method.

As used herein, the term "biological sample" refers to any biological sample obtained from a subject, cell line, tissue, or other source of cells potentially expressing TIGIT (e.g., human TIGIT or cynomolgus TIGIT). Methods for obtaining tissue biopsies and body fluids from animals (e.g., humans or cynomolgus monkeys) are well known in the art. Biological samples include peripheral blood mononuclear cells (PBMCs).

An isolated anti-TIGIT antibody described herein can be used for prognostic, diagnostic, monitoring, and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose, and monitor to evaluate patient samples, including those known to have or suspected of having an immune system-dysfunction or with regard to an anticipated or desired immune system response, antigen response, or vaccine response. The assessment and evaluation of immune system status and/or immune response is also useful in determining the suitability of a patient for a clinical trial of a drug or for the administration of a particular chemotherapeutic agent, a radiotherapeutic agent, or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses. Therefore, in certain embodiments, the present invention relates to an anti-TIGIT antibody and/or pharmaceutical composition of the present invention for use as a diagnostic. In certain embodiments, the present invention relates to an isolated anti-TIGIT antibody, and/or pharmaceutical composition of the present invention for use in a method for the prediction, diagnosis, and/or monitoring of a subject having or suspected to have an immune system-dysfunction and/or with regard to an anticipated or desired immune system response, antigen response or vaccine response. In another embodiment, the present invention relates to the use of an isolated anti-TIGIT antibody of the invention, for predicting, diagnosing, and/or monitoring of a subject having or suspected to have an immune system-dysfunction and/or with regard to an anticipated or desired immune system response, antigen response, or vaccine response by assaying and/or detecting human TIGIT protein levels in a biological sample of the subject in vitro.

In certain embodiments, an isolated anti-TIGIT antibody can be used in immunohistochemistry of biopsy samples. In certain embodiments, the method is an in vitro method. In another embodiment, an isolated anti-TIGIT antibody can be used to detect levels of TIGIT (e.g., human TIGIT or cynomolgus TIGIT), or levels of cells which contain TIGIT (e.g., human TIGIT or cynomolgus TIGIT) on their membrane surface, the levels of which can then be linked to certain disease symptoms. Isolated anti-TIGIT antibodies described herein may carry a detectable or functional label and/or may be conjugated to a radionuclide or detectable label. When fluorescence labels are used, currently available microscopy and fluorescence-activated cell sorter analysis (FACS) or combination of both methods procedures known in the art may be utilized to identify and to quantitate the specific binding members. Isolated anti-TIGIT antibodies described herein may carry or may be conjugated to a fluorescence label. Exemplary fluorescence labels include, for example, reactive and conjugated probes, e.g., Aminocoumarin, Fluorescein and Texas red, Alexa Fluor dyes, Cy dyes and DyLight dyes. An isolated anti-TIGIT antibody may carry or may be conjugated to a radioactive label or radionuclide, such as the isotopes $^3$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac, and $^{186}$Re. When radioactive labels are used, currently available counting procedures known in the art may be utilized to identify and quantitate the specific binding of an isolated anti-TIGIT antibody to TIGIT (e.g., human TIGIT or cynomolgus TIGIT). In the instance where the label is an enzyme, detection may be accomplished by any of the presently utilized colorimetric, spectrophotometric, fluorospectrophotometric, amperometric, or gasometric techniques as known in the art. This can be achieved by contacting a sample or a control sample with an isolated anti-TIGIT antibody under conditions that allow for the formation of a complex between the anti-TIGIT antibody and TIGIT (e.g., human TIGIT or cynomolgus TIGIT). Any complexes formed between the anti-TIGIT antibody and TIGIT (e.g., human TIGIT or cynomolgus TIGIT), are detected and compared in the sample and the control. In light of the specific binding of the anti-TIGIT antibodies described herein for TIGIT (e.g., human TIGIT or cynomolgus TIGIT), the anti-TIGIT antibodies can be used to specifically detect TIGIT (e.g., human TIGIT or cynomolgus TIGIT). The anti-TIGIT antibodies described herein can also be used to purify TIGIT (e.g., human TIGIT or cynomolgus TIGIT) via immunoaffinity purification. Also included herein is an assay system which may be prepared in the form of a test kit, kit, or kit-of-parts for the quantitative analysis of the extent of the presence of, for instance, TIGIT (e.g., human TIGIT or cynomolgus TIGIT)/TIGIT (e.g., human TIGIT or cynomolgus TIGIT) ligand complexes. The system, test kit, kit or kit-of-parts may comprise a labeled component, e.g., a labeled antibody, and one or more additional immunochemical reagents.

7.5 Polynucleotides, Vectors, and Methods of Producing Antibodies

In another aspect, provided herein are polynucleotides comprising a nucleotide sequence encoding an antibody, or a portion thereof, described herein or a fragment thereof (e.g., a VL and/or VH; and a light chain and/or heavy chain) that specifically binds to a TIGIT (e.g., human TIGIT or cynomolgus TIGIT) antigen, and vectors, e.g., vectors comprising such polynucleotides for recombinant expression in host cells (e.g., *E. coli* and mammalian cells). Provided herein are polynucleotides comprising nucleotide sequences encoding a heavy and/or light chain of any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular, less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies, which specifically bind to a TIGIT (e.g., human TIGIT or cynomolgus TIGIT) polypeptide and comprises an amino acid sequence as described herein, as well as antibodies which compete with such antibodies for binding to a TIGIT (e.g., human TIGIT or cynomolgus TIGIT) polypeptide (e.g., in a dose-dependent manner), or which bind to the same epitope as that of such antibodies.

In certain aspects, provided herein are polynucleotides comprising a nucleotide sequence encoding the light chain or heavy chain of antibody described herein. The polynucleotides can comprise nucleotide sequences encoding a light chain comprising the VL FRs and CDRs of antibodies described herein (see, e.g., Table 1) or nucleotide sequences encoding a heavy chain comprising the VH FRs and CDRs of antibodies described herein (see, e.g., Table 1). In certain embodiments, a polynucleotide encodes a VH, VL, heavy chain, and/or light chain of a described herein. In another embodiment, a polynucleotide encodes the first VH and the first VL of a described herein. In another embodiment, a polynucleotide encodes the second VH and the second VL of a described herein. In another embodiment, a polynucleotide encodes the first heavy chain and the first light chain of a described herein. In another embodiment, a polynucleotide encodes the second heavy chain and the second light chain of a described herein. In another embodiment, a polynucleotide encodes the VH and/or the VL, or the heavy chain and/or the light chain, of an isolated antibody described herein.

Also provided herein are polynucleotides encoding an isolated anti-TIGIT antibody that are optimized, e.g., by codon/RNA optimization, replacement with heterologous signal sequences, and elimination of mRNA instability elements. Methods to generate optimized nucleic acids encoding an isolated anti-TIGIT antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In certain embodiments, it can be desirable to alter one or more codons to encode a conservative mutation, e.g., a similar amino acid with similar chemical structure and properties and/or function as the original amino acid. Such methods can increase expression of an isolated anti-TIGIT antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an isolated anti-TIGIT antibody encoded by polynucleotides that have not been optimized.

In certain embodiments, an optimized polynucleotide sequence encoding an isolated anti-TIGIT antibody described herein or a fragment thereof (e.g., VL domain and/or VH domain) can hybridize to an antisense (e.g., complementary) polynucleotide of an unoptimized polynucleotide sequence encoding an isolated anti-TIGIT antibody described herein or a fragment thereof (e.g., VL domain and/or VH domain). In specific embodiments, an optimized nucleotide sequence encoding an isolated anti-TIGIT antibody described herein or a fragment hybridizes under high stringency conditions to antisense polynucleotide of an unoptimized polynucleotide sequence encoding an isolated anti-TIGIT antibody described herein or a fragment thereof. In a specific embodiment, an optimized nucleotide sequence encoding an isolated anti-TIGIT antibody described herein or a fragment thereof hybridizes under high stringency, intermediate, or lower stringency hybridization conditions to an antisense polynucleotide of an unoptimized nucleotide sequence encoding an isolated anti-TIGIT antibody described herein or a fragment thereof. Information regarding hybridization conditions has been described, see, e.g., U.S. Patent Application Publication No. US 2005/0048549 (e.g., paragraphs 72-73), which is herein incorporated by reference in its entirety.

The polynucleotides can be obtained, and the nucleotide sequence of the polynucleotides determined, by any method known in the art. Nucleotide sequences encoding antibodies described herein, e.g., antibodies described in Table 1, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6, herein incorporated by reference in its entirety), which, briefly, involves the synthesis of overlapping oligonucleotides containing portions of the sequence encoding the antibody, annealing, and ligating of those oligonucleotides, and then amplification of the ligated oligonucleotides by PCR.

Alternatively, a polynucleotide encoding an antigen-binding region described herein or an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning.

If a clone containing a nucleic acid encoding a particular antigen-binding region or antibody is not available, but the sequence of the antigen-binding region or antibody molecule is known, a nucleic acid encoding the immunoglobulin can be chemically synthesized or obtained from a suitable source (e.g., an antibody cDNA library or a cDNA library generated from, or nucleic acid, preferably poly A+RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding isolated anti-TIGIT (e.g., human TIGIT or cynomolgus TIGIT) antibodies described herein can be readily isolated and sequenced using conventional procedures (e.g., by using oligonucleotide probes that are capable of binding specifically to genes encoding the heavy and light chains of the anti-TIGIT (e.g., human TIGIT or cynomolgus TIGIT) antibodies). Hybridoma cells can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-TIGIT antibodies in the recombinant host cells.

To generate whole antibodies or antigen-binding regions, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 1 or human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant regions, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant regions in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate, or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, which is herein incorporated by reference in its entirety.

In certain aspects, provided herein are cells (e.g., host cells) expressing (e.g., recombinantly) antibodies described herein which specifically bind to TIGIT (e.g., human TIGIT or cynomolgus TIGIT), and related polynucleotides and expression vectors. Provided herein are vectors (e.g., expression vectors) comprising polynucleotides comprising nucleotide sequences encoding anti-TIGIT antibodies or a fragment for recombinant expression in host cells, preferably in mammalian cells (e.g., CHO cells). Also provided herein are host cells comprising such vectors for recombinantly expressing anti-TIGIT antibodies described herein (e.g., human or humanized antibody). In a particular aspect, provided herein are methods for producing an antibody described herein, comprising expressing the antibody from a host cell.

Recombinant expression of an antibody described herein (e.g., a full-length antigen-binding region or antibody or heavy and/or light chain of an antibody described herein) that specifically binds to TIGIT (e.g., human TIGIT or cynomolgus TIGIT) generally involves construction of an expression vector containing a polynucleotide that encodes the antibody. Once a polynucleotide encoding an antibody molecule, heavy and/or light chain of an antibody, or a fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing an antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable region of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122, 464, which are herein incorporated by reference in their entireties) and variable regions of the antibody can be cloned into such a vector for expression of the entire heavy, the entire light chain, or both the entire heavy and light chains.

In certain embodiments, a vector comprises a polynucleotide encoding a VH, VL, heavy chain, and/or light chain of an antibody described herein. In another embodiment, a vector comprises a polynucleotide encoding the VH and the VL of an antibody described herein. In another embodiment, a vector comprises a polynucleotide encoding the heavy chain and the light chain of an antibody described herein.

An expression vector can be transferred to a cell (e.g., host cell) by conventional techniques and the resulting cells can then be cultured by conventional techniques to produce containing an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell.

In certain embodiments, a host cell comprises a polynucleotide encoding the VH and VL of an isolated antibody described herein. In another embodiment, a host cell comprises a vector comprising a polynucleotide encoding the VH and VL of an isolated antibody described herein. In another embodiment, a host cell comprises a first polynucleotide encoding the VH of an isolated antibody described herein, and a second polynucleotide encoding the VL of an isolated antibody described herein. In another embodiment, a host cell comprises a first vector comprising a first polynucleotide encoding the VH of an isolated antibody described herein, and a second vector comprising a second polynucleotide encoding the VL of an isolated antibody described herein.

In specific embodiments, a heavy chain/heavy chain variable region expressed by a first cell associated with a light chain/light chain variable region of a second cell to form an anti-TIGIT (e.g., human TIGIT or cynomolgus TIGIT) antibody described herein. In certain embodiments, provided herein is a population of host cells comprising such first host cell and such second host cell.

In certain embodiments, provided herein is a population of vectors comprising a first vector comprising a polynucleotide encoding a light chain/light chain variable region of an anti-TIGIT (e.g., human TIGIT or cynomolgus TIGIT) antibody described herein, and a second vector comprising a polynucleotide encoding a heavy chain/heavy chain variable region of an anti-TIGIT (e.g., human TIGIT or cynomolgus TIGIT) antibody described herein.

A variety of host-expression vector systems can be utilized to express antibody molecules described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with, e.g., recombinant bacteriophage DNA, plasmid DNA, or cosmid DNA expression vectors containing antibody coding sequences; yeast (e.g., *Saccharomyces* and *Pichia*) transformed with, e.g., recombinant yeast expression vectors containing antibody coding sequences; insect cell systems infected with, e.g., recombinant virus expression vectors (e.g., baculovirus) containing antibody coding sequences; plant cell systems (e.g., green algae such as *Chlamydomonas reinhardtii*) infected with, e.g., recombinant virus expression vectors (e.g., cauliflower mosaic virus, CaMV; tobacco mosaic virus, TMV) or transformed with, e.g., recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20, and BMT10 cells) harboring, e.g., recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are Chinese hamster ovary (CHO) cells, for example CHO cells from the CHO GS System™ (Lonza). In certain embodiments, the heavy chain and/or light chain of an antibody produced by a CHO cell may have an N-terminal glutamine or glutamate residue replaced by pyroglutamate. In certain embodiments, cells for expressing antibodies described herein are human cells, e.g., human cell lines. In a specific embodiment, a mammalian expression vector is pOptiVEC™ or pcDNA3.3. In certain embodiments, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as CHO cells, in conjunction with a vector such as the major intermediate early gene promoter element from human cytomegalovirus, is an effective expression system for antibodies (Foecking M K & Hofstetter H (1986) Gene 45: 101-5; and Cockett M I et al., (1990) Biotechnology 8(7): 662-7, each of which is herein incorporated by reference in its entirety). In certain embodiments, antibodies described herein are produced by CHO cells or NS0 cells. In a specific embodiment, the expression of nucleotide sequences encoding antibodies described herein which specifically bind to TIGIT (e.g., human TIGIT or cynomolgus TIGIT) is regulated by a constitutive promoter, inducible promoter, or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear poly-hedrosis virus (AcNPV), for example, can be used as a vector to express foreign genes. The virus grows in *Spo-doptera frugiperda* cells. The coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the molecule in infected hosts (see, e.g., Logan J & Shenk T (1984) PNAS 81(12): 3655-9, which is herein incorporated by reference in its entirety). Specific initiation signals can also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544, which is herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10, and HsS78Bst cells. In certain embodiments, anti-TIGIT (e.g., human TIGIT or cynomolgus TIGIT) antibodies described herein are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-TIGIT (e.g., human TIGIT or cynomolgus TIGIT) antibody described herein can be engineered. In specific embodiments, a cell provided herein stably expresses a light chain/light chain variable region and a heavy chain/heavy chain variable region which associate to form an antigen-binding region or an antibody described herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-TIGIT (e.g., human TIGIT or cynomolgus TIGIT) described herein or a fragment thereof. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32); hypoxanthine-guanine phosphoribosyltransferase (Szybalska E H & Szybalski W (1962) PNAS 48(12): 2026-2034); and adenine phosphoribosyltransferase (Lowy I et al., (1980) Cell 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbère-Garapin F et al., (1981) J Mol Biol 150: 1-14, all of which are herein incorporated by reference in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is herein incorporated by reference in its entirety). When a marker in the vector system is amplifiable, increase in the level of inhibitor present in culture of host cell will increase the number of copies of the marker gene. Since the amplified region is associated with the gene of interest, production of the protein will also increase (Crouse G F et al., (1983) Mol Cell Biol 3: 257-66, which is herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: about 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Köhler G (1980) PNAS 77: 2197-2199, each of which is herein incorporated by reference in its entirety). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10, or more genes/nucleotide sequences, or in the range of 2-5, 5-10, or 10-20 genes/nucleotide sequences. For example, a bicistronic nucleic acid construct can comprise, in the following order, a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. In certain embodiments, an isolated antibody is one that is substantially free of other antibodies with different antigenic specificities than the isolated antibody. For example, in certain embodiments, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Anti-TIGIT (e.g., human TIGIT or cynomolgus TIGIT) antibodies or fragments thereof can be produced by any method known in the art for the synthesis of proteins or antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates); Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press, all of which are herein incorporated by reference in their entireties.

In a specific embodiment, an antibody described herein is prepared, expressed, created, or isolated by any means that involves creation, e.g., via synthesis, genetic engineering of DNA sequences. In certain embodiments, such an antibody comprises sequences (e.g., DNA sequences or amino acid sequences) that do not naturally exist within the antibody germline repertoire of an animal or mammal (e.g., human) in vivo.

In one aspect, provided herein is a method of making an anti-TIGIT (e.g., human TIGIT or cynomolgus TIGIT) antibody comprising culturing a cell or host cell described herein. In certain embodiments, the method is performed in vitro. In a certain aspect, provided herein is a method of making an anti-TIGIT (e.g., human TIGIT or cynomolgus TIGIT) antibody comprising expressing (e.g., recombinantly expressing) the antibody using a cell or host cell described herein (e.g., a cell or a host cell comprising polynucleotides encoding an antibody described herein). In certain embodiments, the cell is an isolated cell. In certain embodiments, the exogenous polynucleotides have been introduced into the cell. In certain embodiments, the method further comprises the step of purifying the antibody obtained from the cell or host cell.

In certain embodiments, an isolated antibody is produced by expressing in a cell a polynucleotide encoding the VH and VL of an antibody described herein under suitable conditions so that the polynucleotides are expressed and the antibody is produced. In another embodiment, an isolated antibody is produced by expressing in a cell a polynucleotide encoding the heavy chain and light chain of an antibody described herein under suitable conditions so that the polynucleotides are expressed and the antibody is produced. In certain embodiments, an isolated antibody is produced by expressing in a cell a first polynucleotide encoding the VH of an antibody described herein, and a second polynucleotide encoding the VL of an antibody described herein, under suitable conditions so that the polynucleotides are expressed and the antibody is produced. In certain embodiments, an isolated antibody is produced by expressing in a cell a first polynucleotide encoding the heavy chain of an antibody described herein, and a second polynucleotide encoding the light chain of an antibody described herein, under suitable conditions so that the polynucleotides are expressed and the antibody is produced.

Methods for producing polyclonal antibodies are known in the art (see, for example, Chapter 11 in: Short Protocols in Molecular Biology, (2002) 5th Ed., Ausubel F M et al., eds., John Wiley and Sons, New York, which is herein incorporated by reference in its entirety).

Monoclonal antibodies can be prepared using a wide variety of techniques known in the art, including the use of hybridoma, recombinant, and phage display technologies, or a combination thereof. For example, monoclonal antibodies can be produced using hybridoma techniques, including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), each of which is herein incorporated by reference in its entirety. The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to TIGIT (e.g., human TIGIT or cynomolgus TIGIT) as determined, e.g., by ELISA or other antigen-binding or competitive binding assay known in the art or in the examples provided herein. In certain embodiments, a monoclonal antibody can be a chimeric antibody or a humanized antibody. In certain embodiments, a monoclonal antibody is a monovalent antibody or multivalent (e.g., bivalent) antibody. In certain embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256: 495, which is herein incorporated by reference in its entirety, or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

As used herein, an antibody binds to an antigen multivalently (e.g., bivalently) when the antibody comprises at least two (e.g., two or more) monovalent binding regions, each monovalent binding region capable of binding to an epitope on the antigen. Each monovalent binding region can bind to the same or different epitopes on the antigen.

Methods for producing and screening for specific antibodies using hybridoma technology are routine and well known in the art. For example, in the hybridoma method, a mouse or other appropriate host animal, such as a sheep, goat, rabbit, rat, hamster, or macaque monkey, is immunized to elicit lymphocytes that produce or are capable of producing antibodies that will specifically bind to the protein (e.g., TIGIT (e.g., human TIGIT or cynomolgus TIGIT)) used for immunization. Alternatively, lymphocytes may be immunized in vitro. Lymphocytes then are fused with myeloma cells using a suitable fusing agent, such as polyethylene glycol, to form a hybridoma cell (Goding J W (ed.), Monoclonal Antibodies: Principles and Practice, pp. 59-103 (Academic Press, 1986), herein incorporated by reference in its entirety). Additionally, a RIMMS (repetitive immunization multiple sites) technique can be used to immunize an animal (Kilpatrick K E et al., (1997) Hybridoma 16:381-9, herein incorporated by reference in its entirety).

In certain embodiments, mice (or other animals, such as rats, monkeys, donkeys, pigs, sheep, hamster, or dogs) can be immunized with an antigen (e.g., TIGIT (e.g., human TIGIT or cynomolgus TIGIT)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example, cells from cell line SP20 available from the American Type Culture Collection (ATCC®) (Manassas, VA), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as the NSO cell line or those derived from MOPC-21 and MPC-11 mouse tumors available from the Salk Institute Cell Distribution Center, San Diego, CA, USA, and SP-2 or X63-Ag8.653 cells available from the American Type Culture Collection, Rockville, MD, USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp.

51-63 (Marcel Dekker, Inc., New York, 1987), each of which is herein incorporated by reference in its entirety).

Culture medium in which hybridoma cells are growing is assayed for production of monoclonal antibodies directed against TIGIT (e.g., human TIGIT or cynomolgus TIGIT). The binding specificity of monoclonal antibodies produced by hybridoma cells is determined by methods known in the art, for example, immunoprecipitation or by an in vitro binding assay, such as radioimmunoassay (RIA) or enzyme-linked immunosorbent assay (ELISA).

After hybridoma cells are identified that produce antibodies of the desired specificity, affinity, and/or activity, the clones may be subcloned by limiting dilution procedures and grown by standard methods (Goding J W (ed.), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include, e.g., antibody fragments which recognize TIGIT (e.g., human TIGIT or cynomolgus TIGIT), and can be generated by any technique known to those of skill in the art. For example, Fab and $F(ab')_2$ fragments described herein can be produced by proteolytic cleavage of immunoglobulin molecules, using enzymes such as papain (to produce Fab fragments) or pepsin (to produce $F(ab')_2$ fragments). A Fab fragment corresponds to one of the two identical arms of an antibody molecule and contains the complete light chain paired with the VH and CH1 domains of the heavy chain. A $F(ab')_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage, including fd and M13, and the VH and VL domains are usually recombinantly fused to either the phage gene III or gene VIII. Phage expressing an antigen-binding region that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108, all of which are herein incorporated by reference in their entireties.

As described in the above references, after phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produce antibody fragments such as Fab, Fab', and $F(ab')_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043, all of which are herein incorporated by reference in their entireties.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415, all of which are herein incorporated by reference in their entireties.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In certain embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA, and IgE, and any isotype, including $IgG_1$, $IgG_2$, $IgG_3$, and $IgG_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10; and Pedersen J T et al., (1994) J Mol Biol 235(3): 959-73, all of which are herein incorporated by reference in their entireties. See also, U.S. Application Publication No. US 2005/0042664 A1 (Feb. 24, 2005), which is herein incorporated by reference in its entirety.

Methods for making multispecific antibodies (e.g., bispecific antibodies) have been described, see, for example, U.S. Pat. Nos. 7,951,917; 7,183,076; 8,227,577; 5,837,242; 5,989,830; 5,869,620; 6,132,992; and 8,586,713, all of which are herein incorporated by reference in their entireties.

Bispecific, bivalent antibodies, and methods of making them, are described, for instance in U.S. Pat. Nos. 5,731, 168; 5,807,706; 5,821,333; and U.S. Appl. Publ. Nos. 2003/020734 and 2002/0155537, each of which is herein incorporated by reference in its entirety. Bispecific tetravalent antibodies, and methods of making them are described, for instance, in Int. Appl. Publ. Nos. WO02/096948 and WO00/44788, the disclosures of both of which are herein incorporated by reference in its entirety. See generally, Int. Appl. Publ. Nos. WO93/17715, WO92/08802, WO91/00360, and WO92/05793; Tutt et al., J. Immunol. 147:60-69 (1991); U.S. Pat. Nos. 4,474,893; 4,714,681; 4,925,648; 5,573,920; and 5,601,819; and Kostelny et al., J. Immunol. 148:1547-1553 (1992), each of which is herein incorporated by reference in its entirety.

A bispecific antibody as described herein can be generated according to the DuoBody technology platform (Genmab A/S) as described, e.g., in International Publication Nos. WO 2011/131746, WO 2011/147986, WO 2008/119353, and WO 2013/060867, and in Labrijn A F et al., (2013) PNAS 110(13): 5145-5150. The DuoBody technology can be used to combine one half of a first monospecific antibody, or first antigen-binding region, containing two heavy and two light chains with one half of a second monospecific antibody, or second antigen-binding region, containing two heavy and two light chains. The resultant heterodimer contains one heavy chain and one light chain from the first antibody, or first antigen-binding region, paired with one heavy chain and one light chain from the second antibody, or second antigen-binding region. When both of the monospecific antibodies, or antigen-binding regions, recognize different epitopes on different antigens, the resultant heterodimer is a bispecific antibody.

The DuoBody technology requires that each of the monospecific antibodies, or antigen-binding regions includes a heavy chain constant region with a single point mutation in the CH3 domain. The point mutations allow for a stronger interaction between the CH3 domains in the resultant bispecific antibody than between the CH3 domains in either of the monospecific antibodies, or antigen-binding regions. The single point mutation in each monospecific antibody, or antigen-binding region, is at residue 366, 368, 370, 399, 405, 407, or 409, numbered according to the EU numbering system, in the CH3 domain of the heavy chain constant region, as described, e.g., in International Publication No.

WO 2011/131746. Moreover, the single point mutation is located at a different residue in one monospecific antibody, or antigen-binding region, as compared to the other monospecific antibody, or antigen-binding region. For example, one monospecific antibody, or antigen-binding region, can comprise the mutation F405L (i.e., a mutation from phenylalanine to leucine at residue 405), while the other monospecific antibody, or antigen-binding region, can comprise the mutation K409R (i.e., a mutation from lysine to arginine at residue 409), numbered according to the EU numbering system. The heavy chain constant regions of the monospecific antibodies, or antigen-binding regions, can be an $IgG_1$, $IgG_2$, $IgG_3$, or $IgG_4$ isotype (e.g., a human $IgG_1$ isotype), and a bispecific antibody produced by the DuoBody technology can retain Fc-mediated effector functions.

Another method for generating bispecific antibodies has been termed the "knobs-into-holes" strategy (see, e.g., Intl. Publ. WO2006/028936). The mispairing of Ig heavy chains is reduced in this technology by mutating selected amino acids forming the interface of the CH3 domains in IgG. At positions within the CH3 domain at which the two heavy chains interact directly, an amino acid with a small side chain (hole) is introduced into the sequence of one heavy chain and an amino acid with a large side chain (knob) into the counterpart interacting residue location on the other heavy chain. In some embodiments, compositions of the invention have immunoglobulin chains in which the CH3 domains have been modified by mutating selected amino acids that interact at the interface between two polypeptides so as to preferentially form a bispecific antibody. The bispecific antibodies can be composed of immunoglobulin chains of the same subclass (e.g., $IgG_1$ or $IgG_3$) or different subclasses (e.g., $IgG_1$ and $IgG_3$, or $IgG_3$ and $IgG_4$).

Bispecific antibodies can, in some instances contain, $IgG_4$ and $IgG_1$, $IgG_4$ and $IgG_2$, $IgG_4$ and $IgG_2$, $IgG_4$ and $IgG_3$, or $IgG_1$ and $IgG_3$ chain heterodimers. Such heterodimeric heavy chain antibodies can routinely be engineered by, for example, modifying selected amino acids forming the interface of the CH3 domains in human $IgG_4$ and the $IgG_1$ or $IgG_3$ so as to favor heterodimeric heavy chain formation.

In certain embodiments, an antibody described herein, which binds to the same epitope of TIGIT (e.g., human TIGIT or cynomolgus TIGIT) as an anti-TIGIT (e.g., human TIGIT or cynomolgus TIGIT) antibody described herein, is a human antibody. In certain embodiments, an antibody described herein, which competitively blocks (e.g., in a dose-dependent manner) any one of the antibodies described herein, from binding to TIGIT (e.g., human TIGIT or cynomolgus TIGIT), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., TIGIT (e.g., human TIGIT or cynomolgus TIGIT)). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM, and IgE antibodies. For an overview of this technology for producing human antibodies, see Lonberg N & Huszar D (1995) Int Rev Immunol 13:65-93, herein incorporated by reference in its entirety. For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569, 825, 5,661,016, 5,545,806, 5,814,318, and 5,939,598, all of which are herein incorporated by reference in their entireties. Examples of mice capable of producing human antibodies include the XenoMouse™ (Abgenix, Inc.; U.S. Pat. Nos. 6,075,181 and 6,150,184), the HuAb-Mouse™ (Medarex, Inc./Gen Pharm; U.S. Pat. Nos. 5,545,806 and 5,569, 825), the Trans Chromo Mouse™ (Kirin) and the KM Mouse™ (Medarex/Kirin), all of which are herein incorporated by reference in their entireties.

Human antibodies that specifically bind to TIGIT (e.g., human TIGIT or cynomolgus TIGIT) can be made by a variety of methods known in the art including the phage display methods described above using antibody libraries derived from human immunoglobulin sequences. See also, U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741, all of which are herein incorporated by reference in their entireties.

In certain embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., TIGIT (e.g., human TIGIT or cynomolgus TIGIT)). Such methods are known and are described in the art, see, e.g., Shinmoto H et al., (2004) Cytotechnology 46: 19-23; Naganawa Y et al., (2005) Human Antibodies 14: 27-31, each of which is herein incorporated by reference in its entirety.

7.6 Kits

Also provided are kits comprising one or more antibodies described herein, or pharmaceutical compositions or conjugates thereof. In a specific embodiment, provided herein is a pharmaceutical pack or kit comprising one or more containers filled with one or more of the ingredients of the pharmaceutical compositions described herein, such as one or more antibodies provided herein. In certain embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use, or sale of pharmaceuticals or biological products, which notice reflects approval by the agency of manufacture, use, or sale for human administration.

Also provided, are kits that can be used in the above methods. In certain embodiments, a kit comprises an antibody described herein, preferably purified antibody, in one or more containers. In a specific embodiment, kits described herein contain a substantially isolated TIGIT (e.g., human TIGIT or cynomolgus TIGIT) antigen as a control. In another specific embodiment, the kits described herein further comprise a control antibody which does not react with TIGIT (e.g., human TIGIT or cynomolgus TIGIT) antigen. In another specific embodiment, kits described herein contain one or more elements for detecting the binding of an antibody to a TIGIT (e.g., human TIGIT or cynomolgus TIGIT) antigen (e.g., the antibody can be conjugated to a detectable substrate such as a fluorescent compound, an enzymatic substrate, a radioactive compound, or a luminescent compound, or a second antibody which recognizes the first antibody can be conjugated to a detectable substrate). In specific embodiments, a kit provided herein can include a recombinantly produced or chemically synthesized TIGIT (e.g., human TIGIT or cynomolgus TIGIT) antigen. The TIGIT (e.g., human TIGIT or cynomolgus TIGIT) antigen provided in the kit can also be attached to a solid support. In a more specific embodiment, the detecting means of the above-described kit includes a solid support to which a TIGIT (e.g., human TIGIT or cynomolgus TIGIT) antigen is attached. Such a kit can also include a non-attached reporter-labeled anti-human antibody or anti-mouse/rat antibody. In this embodiment, binding of the antibody to the TIGIT (e.g., human TIGIT or cynomolgus TIGIT) antigen can be detected by binding of the said reporter-labeled antibody. In certain embodiments, the present invention relates to the use of a kit of the present invention for in vitro assaying and/or detecting TIGIT (e.g., human TIGIT or cynomolgus TIGIT) antigen in a biological sample.

8. EXAMPLES

The examples in this Section (i.e., Section 8) are offered by way of illustration and not by way of limitation.

8.1 Example 1: Charge State of BA159 and an Anti-TIGIT Reference Antibody

The charge states of BA159 and an anti-TIGIT reference antibody were assessed using cation exchange chromatography.

Briefly, an Agilent 1260 HPLC and a Propac WCX-10 Column (Thermo) were used to separate each antibody based on its surface charge. Each antibody was diluted to 1.0 mg/ml in a 10 mM Histidine pH 6, 115 mM NaCl solution. Then 10 µl was injected onto a Propac WCX-10 Column (Thermo) equilibrated in 20 mM sodium citrate pH 5.5. A gradient elution was run at 1 ml/min over 20 minutes into a 20 mM sodium citrate pH 6.0, 250 mM NaCl solution. Molecules eluted from the column were detected using absorbance at 280 nm.

Figures 1A, 1B:
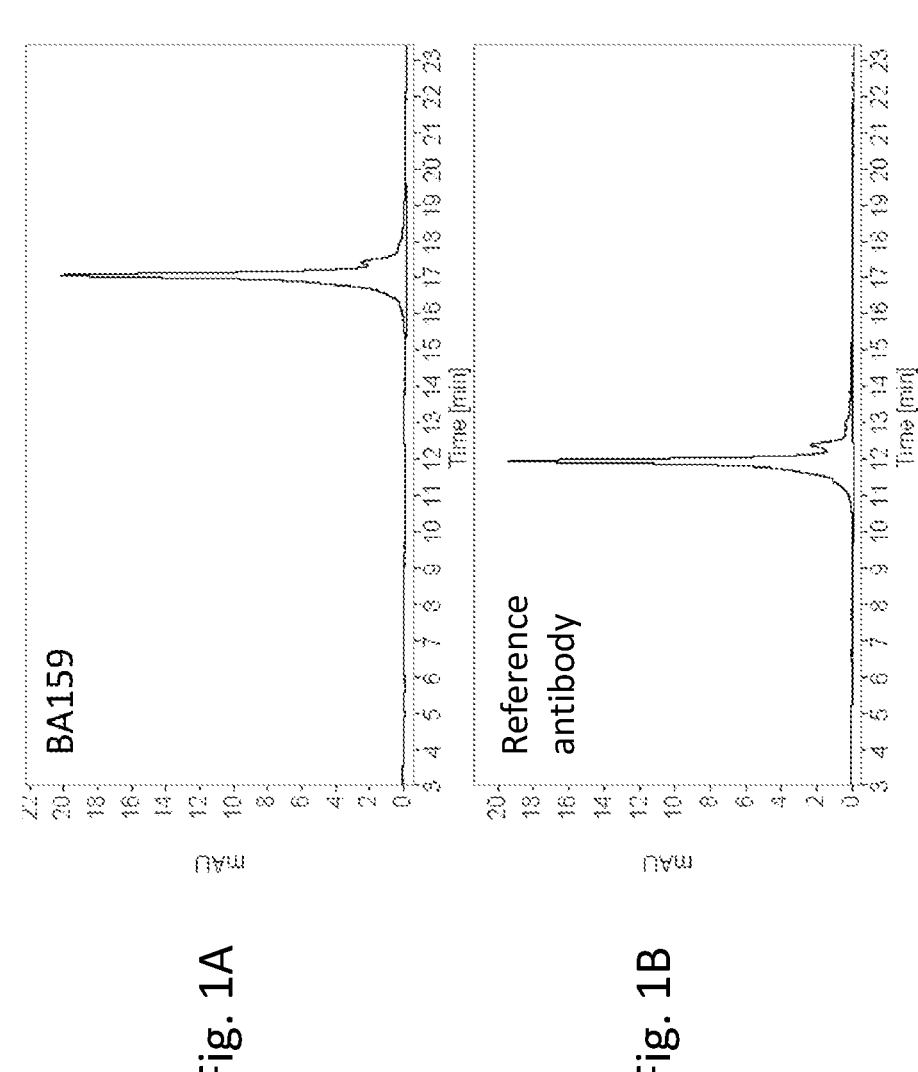
FIG. 1A and FIG. 1B are cation exchange chromatography traces showing the elution time for BA159 (FIG. 1A) and an anti-TIGIT reference antibody (FIG. 1B). The absorbance at 280 nm is plotted against retention time.

As shown in FIGS. 1A and 1B, BA159 elutes at a higher ionic strength (17.1 min) than the anti-TIGIT reference antibody (11.9 min), indicating that BA159 has a higher charge state at pH 5.5-6.0 and is less acidic than the anti-TIGIT reference antibody.

8.2 Example 2: Thermal Stability of BA159 and an Anti-TIGIT Reference Antibody The thermal stability of BA159 and an anti-TIGIT reference antibody was assessed using thermal melts.

Briefly, an Uncle protein stability platform from Unchained Labs was used to increase the sample temperature and then the intrinsic fluorescence and aggregation were measured. Each antibody was diluted to 1.0 mg/ml in a 10 mM Histidine pH 6, 115 mM NaCl solution. Samples were then spun at 13,000 rpm for 10 minutes to remove any dust particles or very large aggregates. 9.0 μl of diluted antibody was loaded in duplicate into a Uni, which was inserted into the Uncle, and the thermal melt protocol "Tm & Tagg with optional DLS" was run. The temperature of the sample was increased from 20-90° C. at 1° C./minute, while the sample was illuminated with a 266 nm laser, and the intrinsic fluorescence of the sample was measured to follow sample unfolding. The florescence data was analyzed by using the barycentric mean (BCM). Samples were run in duplicate and the mean unfolding temperature (Tm) was calculated for each antibody. The static light scattering (SLS) of the 266 nm laser by the sample was also measured at 90° to the light source. Samples were run in duplicate and the mean aggregation temperature (Tagg) was calculated for each antibody. All calculations were performed using Uncle software. Data quality was verified using visual inspection.

Figures 2A, 2B:
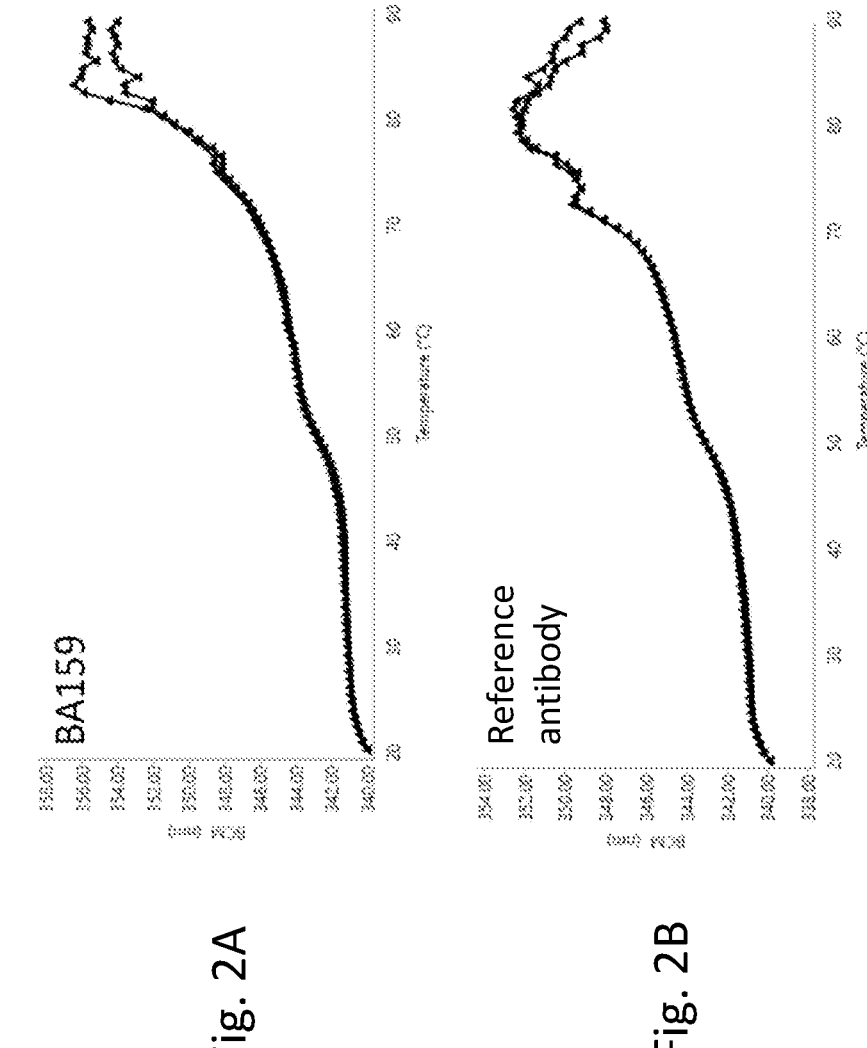
FIG. 2A and FIG. 2B are thermal melt traces showing the unfolding of BA159 (FIG. 2A) and an anti-TIGIT reference antibody (FIG. 2B). The barycentric mean of the intrinsic fluorescence is plotted against temperature.
Figures 3A, 3B:
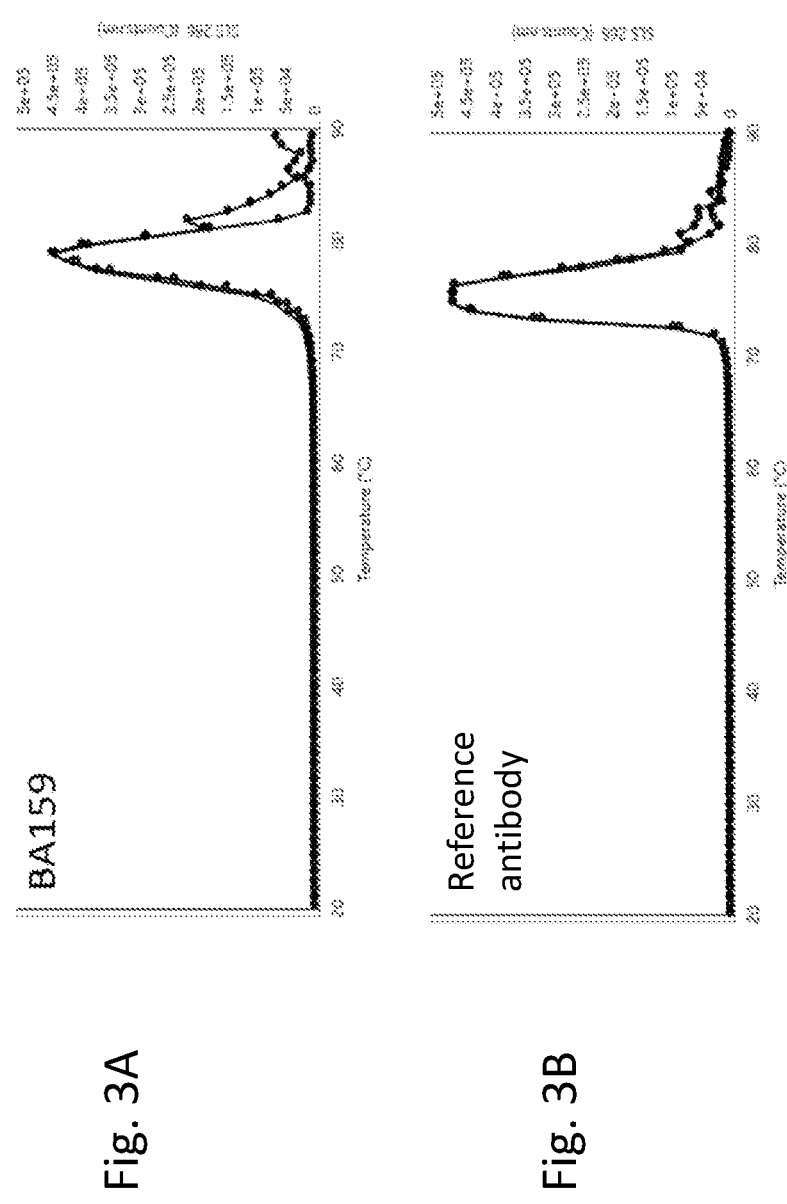
FIG. 3A and FIG. 3B are thermal melt traces showing the aggregation of BA159 (FIG. 3A) and an anti-TIGIT reference antibody (FIG. 3B). The static light scattering at 266 nm is plotted against temperature.
Figures 4A, 4B:
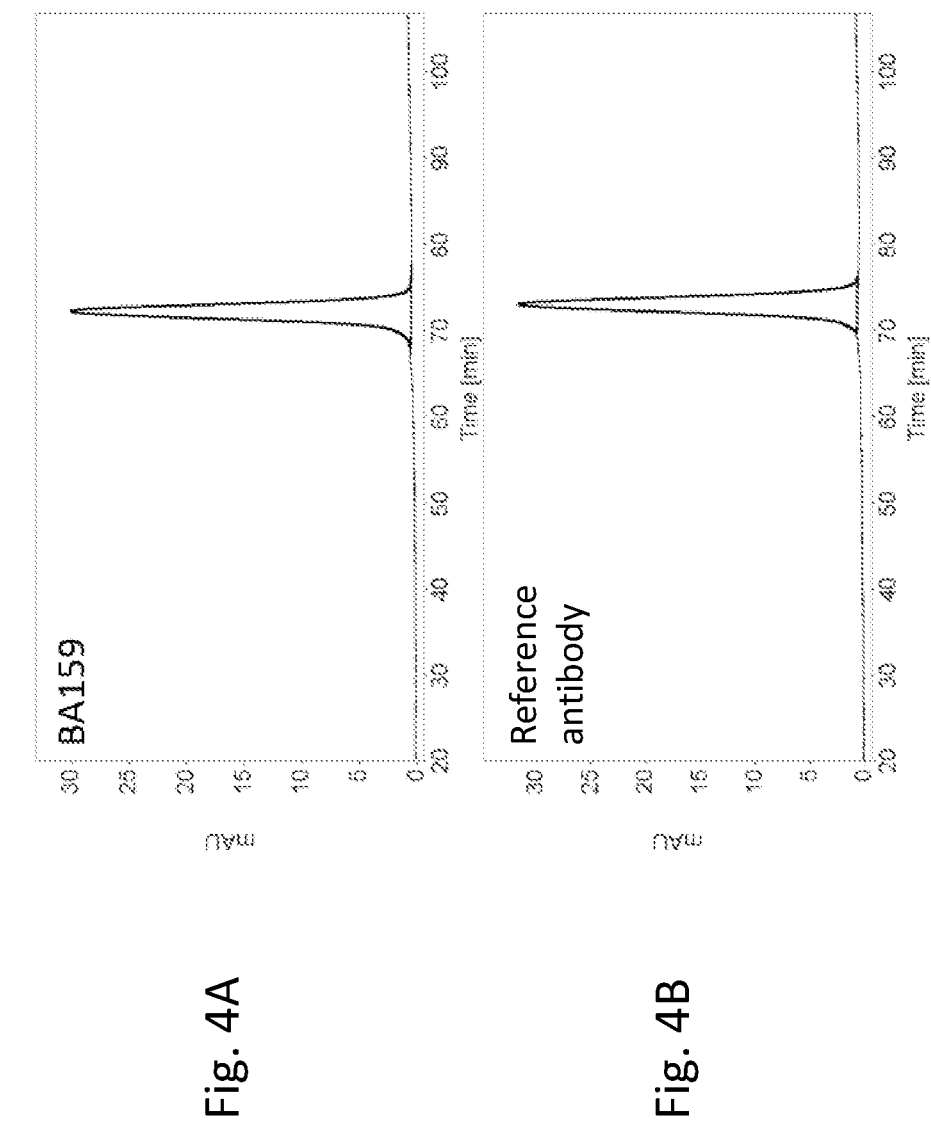
FIG. 4A-FIG. 4D are FcRn affinity chromatography traces showing the elution time for BA159 (FIG. 4A), an anti-TIGIT reference antibody (FIG. 4B), a control $IgG_1$ mAb (FIG. 4C), and a polyclonal IgG mixture (FIG. 4D). The absorbance at 280 nm is plotted against retention time.
Figures 4C, 4D:
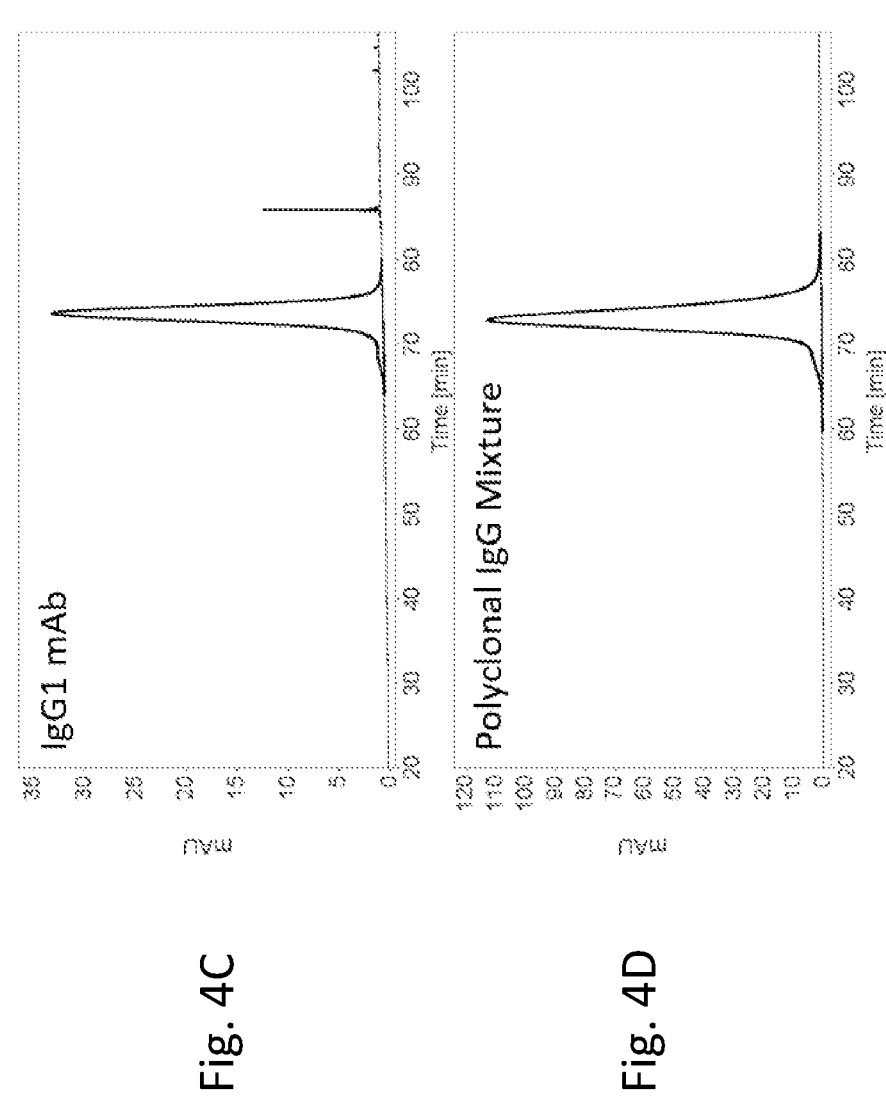

The results shown in FIG. 2A, FIG. 2B, and Table 3 demonstrate that both BA159 and the anti-TIGIT reference antibody have two unfolding transitions, and that the second unfolding transition for the anti-TIGIT reference antibody occurs at a lower temperature, indicating that BA159 is more thermally stable than the anti-TIGIT reference antibody. FIG. 3A and FIG. 3B show that the aggregation profiles of BA159 and the anti-TIGIT reference antibody are comparable.

TABLE 3

Unfolding and aggregation temperatures of BA159 and an anti-TIGIT reference antibody.

|  | BA159 | anti-TIGIT reference antibody |
|---|---|---|
| Tm1 (° C.) | 50 | 50 |
| Tm2 (° C.) | 77 | 71 |
| Tagg (° C.) | 73 | 71 |

8.3 Example 3: FcRn Binding Profile of BA159 and an Anti-TIGIT Reference Antibody The pH dependence of antibody binding to a recombinant version of the human neonatal Fc receptor was assessed for BA159 and an anti-TIGIT reference antibody using affinity chromatography.

Briefly, an Agilent 1260 HPLC and an FcRn affinity column (Roche) were used to separate BA159 and an anti-TIGIT reference antibody based on the pH that the antibody elutes from FcRn. Each molecule was diluted to 1.0 mg/ml in a 10 mM Histidine pH 6, 115 mM NaCl solution and then 10 μl was injected onto an FcRn Affinity Column (Roche) equilibrated in 20 mM IVIES pH 5.5, 140 mM NaCl. A gradient elution was run at 0.1 ml/min over 77 minutes into 20 mM TRIS pH 8.8, 140 mM NaCl. Molecules eluting from the column were detected using absorbance at 280 nm. Data quality was verified using a well-characterized control IgG$_1$ antibody and a polyclonal mixture of IgG from human serum (Sigma-Aldrich) as assay controls, as well as using visual inspection.

As shown in FIGS. 4A-4D, and Table 4, BA159 and the anti-TIGIT reference antibody eluted from the column with a similar retention time and pH as the control IgG$_1$ antibody and the polyclonal IgG mixture.

TABLE 4

Retention time for BA159, an anti-TIGIT reference antibody, a control IgG$_1$ mAb, and a polyclonal IgG mixture.

|  | BA159 | anti-TIGIT reference antibody | Control IgG$_1$ mAb | Polyclonal IgG Mixture |
|---|---|---|---|---|
| Retention Time (min) | 73 | 72 | 73 | 74 |

8.4 Example 4: Interchain Disulphide Bond Formation for BA159 and BA160

The extent of interchain disulphide bonding for BA159 and BA160 was assessed using non-reducing CE SDS. BA159 and BA160 have the same heavy and light chain sequences, except that the light chain of BA160 lacks a C-terminal serine.

Briefly, a Perkin Elmer Lab Chip GTX II Touch HT and a Protein Express Assay Kit were used to unfold the antibodies. Non-covalent interactions were disrupted using a protocol designed to probe the stability of the Heavy Chain-Light Chain disulphide bond, then to separate the molecules based on size using a voltage applied across a sieving matrix.

Each antibody was diluted to 0.1 mg/ml in Protein Express Sample Buffer, then heated at 100° C. for 5 minutes. Each sample was sipped by the Lab Chip into the microfluidics of the instrument, mixed with Protein Express Dye solution, and then a few μl were pulled into the separating channel by an applied voltage. Once separated, the samples were destained using the Destaining Solution and the separated molecules were detected by the fluorescence of the dye using a laser. The size of the molecules was determined using a ladder supplied with the Protein Express Kit. Data quality was verified using parameters determined by the Lab Chip and by visual inspection.

Figures 5A, 5B:
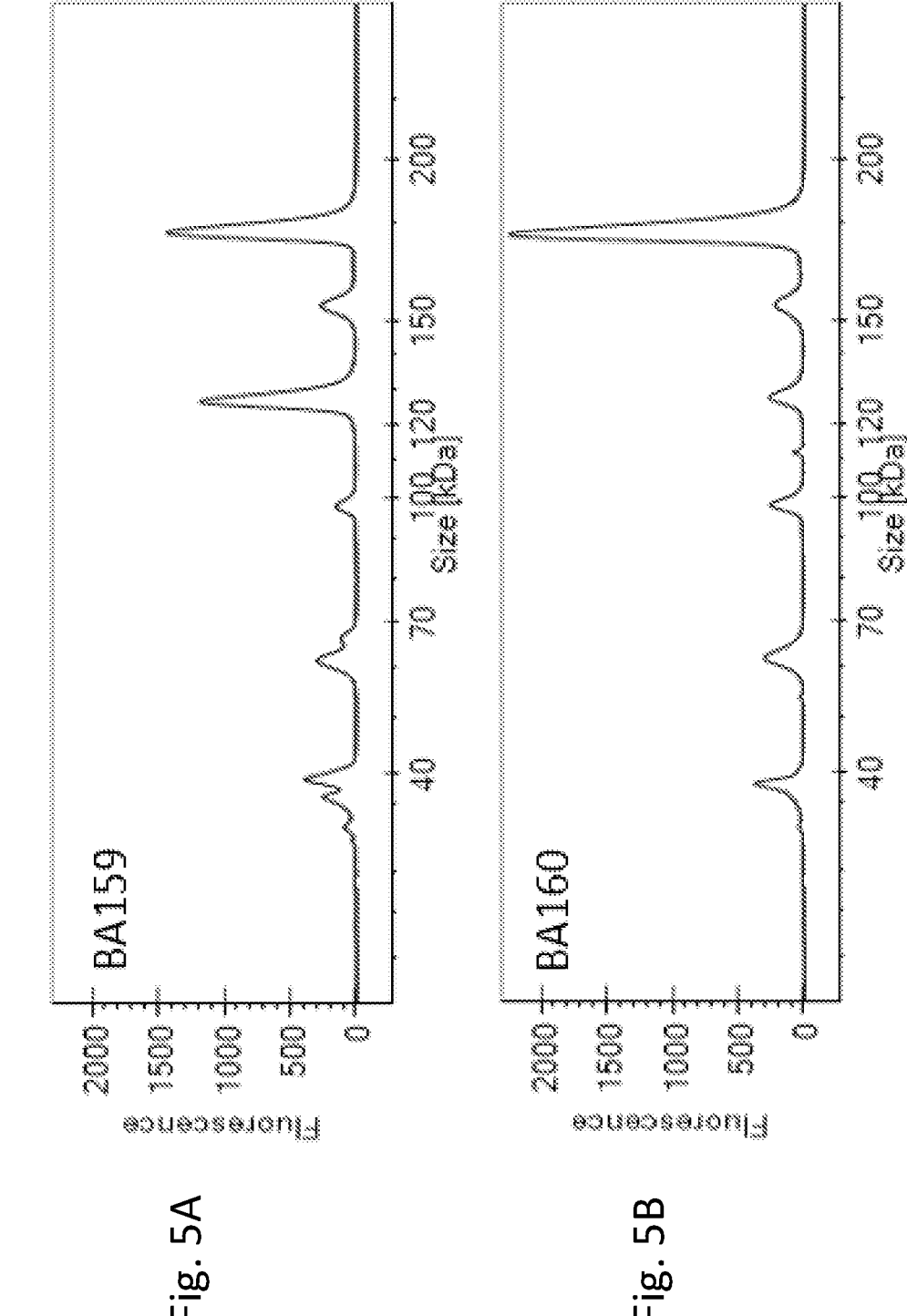
FIG. 5A and FIG. 5B are capillary electrophoresis sodium dodecyl sulfate (CE SDS) electropherograms showing the extent of interchain disulphide bonding for BA159 (FIG. 5A) and BA160 (FIG. 5B) under non-reducing conditions. The fluorescence of molecules running at different sizes is shown.

As shown in FIG. 5A and FIG. 5B, and Table 5, BA160 has more molecules with fully formed heavy chain-light chain disulphide bonds (LHHL) than BA159.

TABLE 5

Interchain disulphide bonding for BA159 and BA160 molecules.

| Chains linked by disulphide bonds | Approx. Size (kDa) | BA159 | BA160 |
|---|---|---|---|
| LHHL | 176 | 43% | 69% |
| HHL | 154 | 8% | 7% |
| HH | 127 | 30% | 7% |
| HL | 98 | 3% | 5% |
| H | 62 | 8% | 6% |
| L | 38 | 9% | 6% |

8.5 Example 5: Other Biophysical Properties of
BA159 and BA160

8.5.1 Charge State of Anti-TIGIT Antibodies

The charge states of BA159, BA160, and an anti-TIGIT reference antibody were assessed using cation exchange chromatography. Methods were followed as described in Example 1.

Figures 6A, 6B:
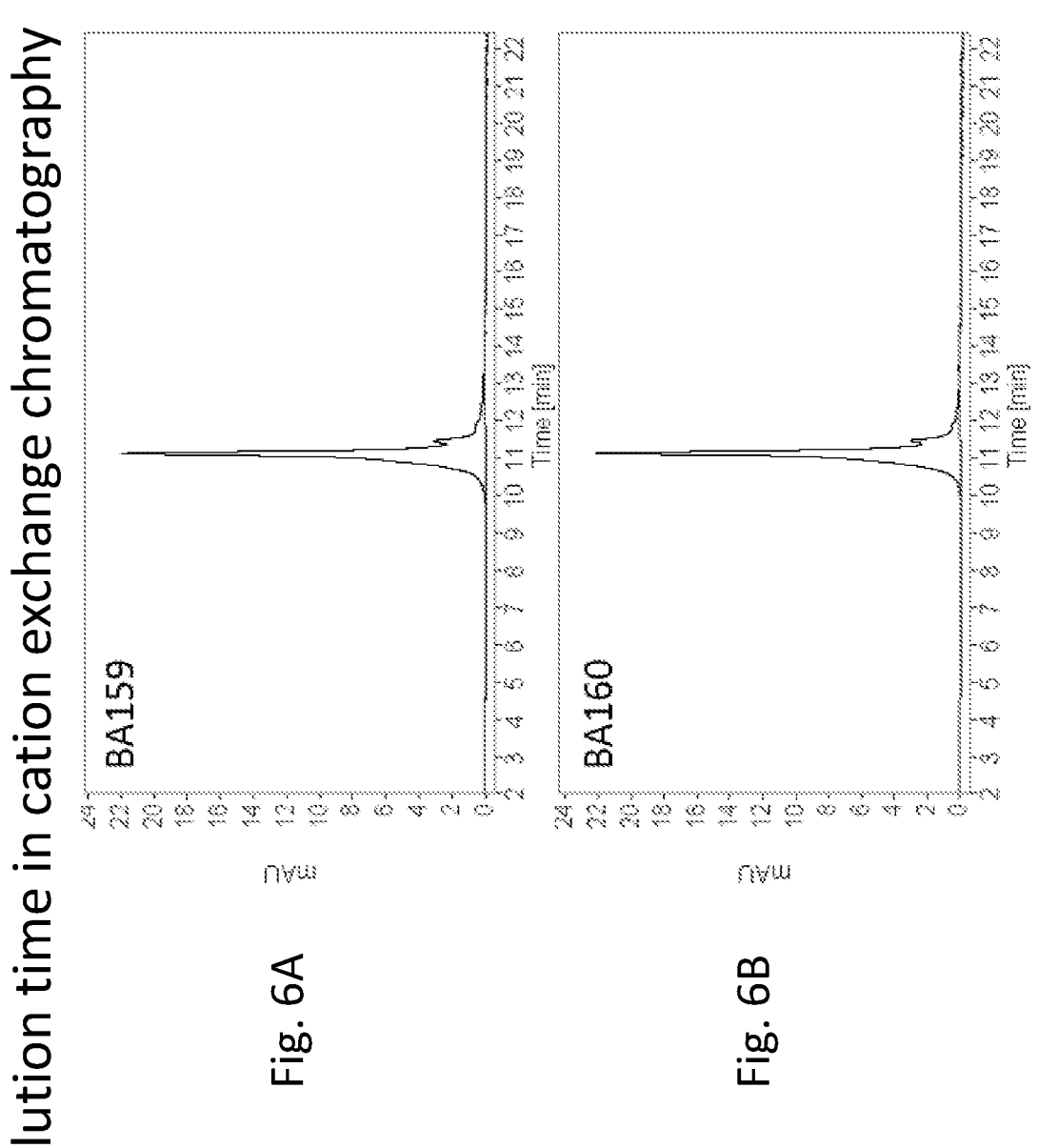
FIG. 6A and FIG. 6B are cation exchange chromatography traces showing the elution time for BA159 (FIG. 6A) and BA160 (FIG. 6B). The absorbance at 280 nm is plotted against retention time.

As shown in FIG. 6A and FIG. 6B, BA159 (11.1 min) and BA160 (11.1 min) elute at a similar ionic strength, indicating that both antibodies have comparable surface charges.

8.5.2 Thermal Stability of Anti-TIGIT Antibodies

The thermal stability of BA159, BA160, and an anti-TIGIT reference antibody was assessed using thermal melts. Methods were followed as described in Example 2.

Figures 7A, 7B:
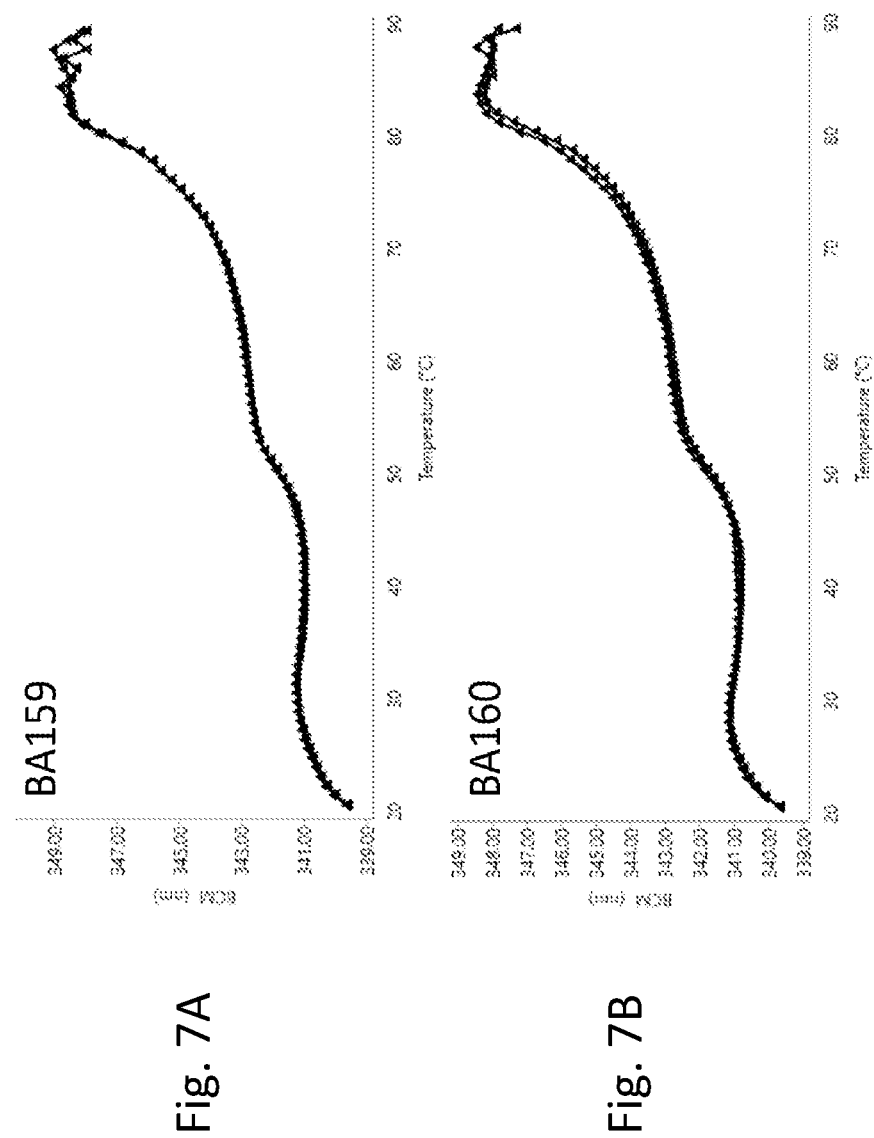
FIG. 7A and FIG. 7B are thermal melt traces showing the unfolding of BA159 (FIG. 7A) and BA160 (FIG. 7B). The barycentric mean of the intrinsic fluorescence is plotted against temperature.
Figures 8A, 8B:
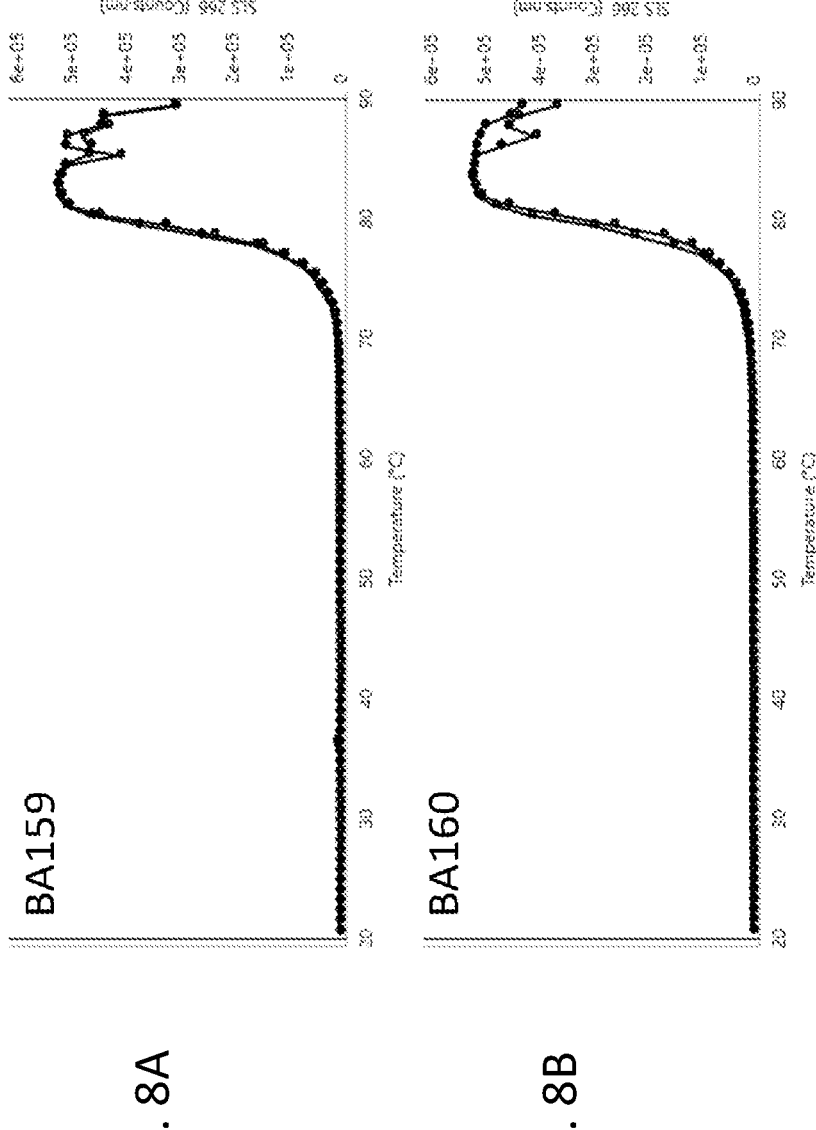
FIG. 8A and FIG. 8B are thermal melt traces showing the aggregation of BA159 (FIG. 8A) and BA160 (FIG. 8B). The static light scattering at 266 nm is plotted against temperature.
Figures 9A, 9B:
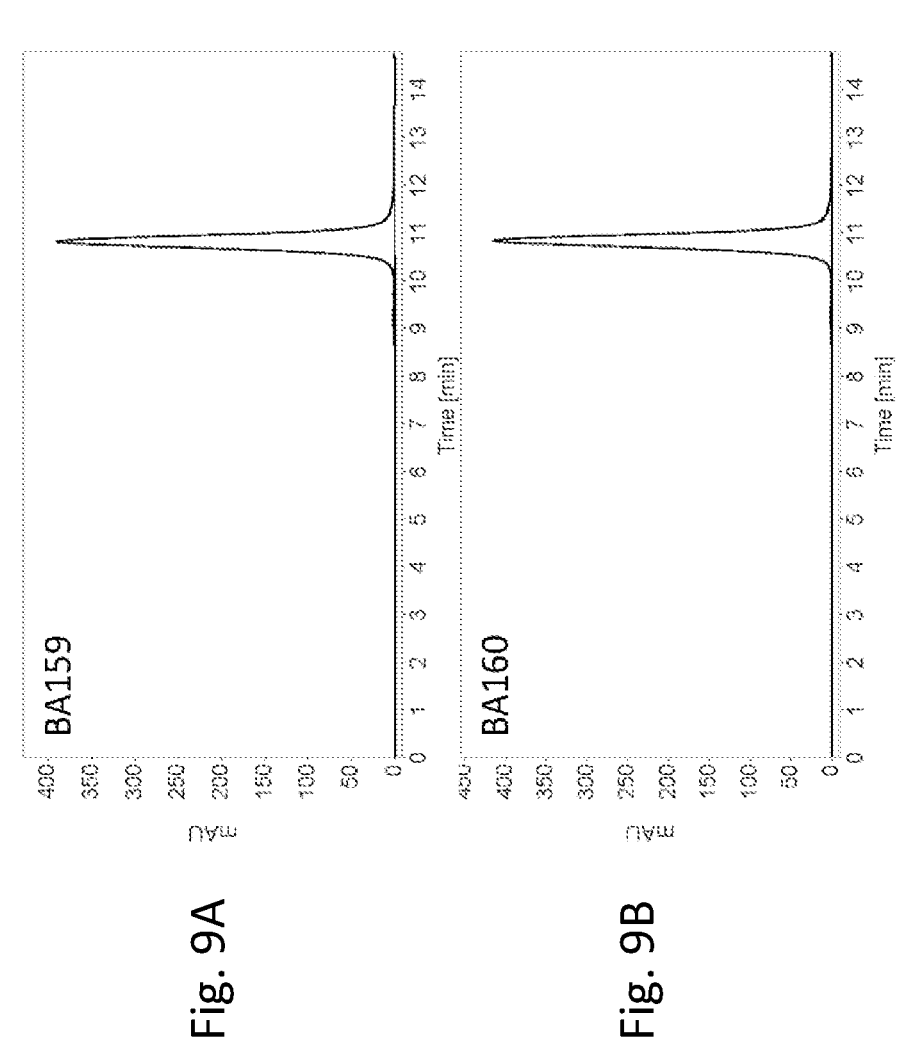
FIG. 9A-FIG. 9C are a series of size exclusion chromatography traces showing the elution time for BA159 (FIG. 9A), BA160 (FIG. 9B), and an anti-TIGIT reference antibody (FIG. 9C). The absorbance at 214 nm is plotted against retention time.
Figure 9C:
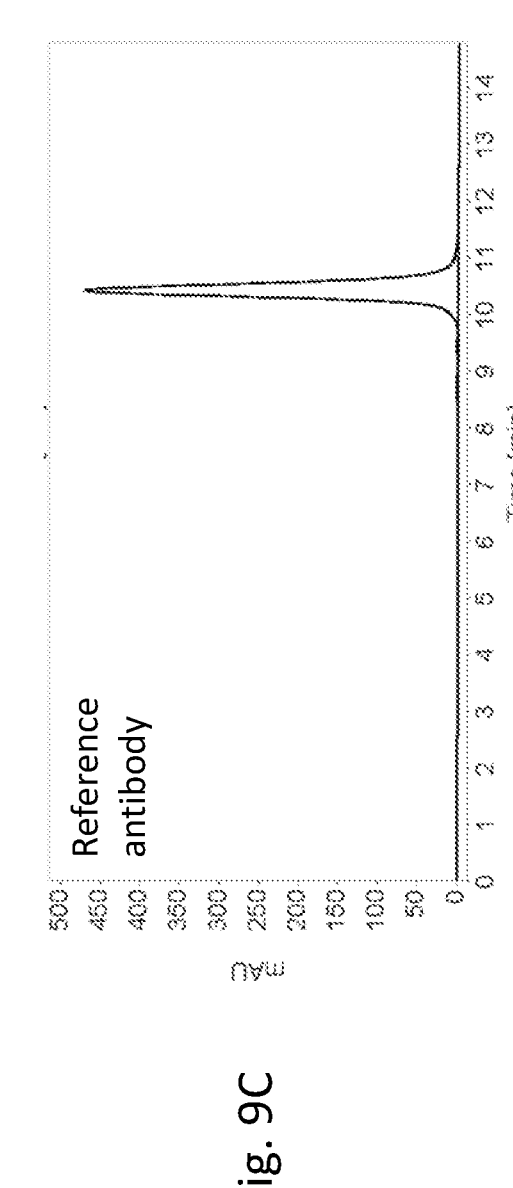

As shown in FIG. 7A, FIG. 7B, and Table 6, BA159 and BA160 have comparable unfolding profiles with two unfolding transitions. BA159 and BA160 also have comparable aggregation profiles, as shown in FIGS. 8A and 8B, respectively.

TABLE 6

Unfolding and aggregation temperatures of BA159 and BA160.

|  | BA159 | BA160 |
|---|---|---|
| Tm1 (° C.) | 51 | 51 |
| Tm2 (° C.) | 80 | 80 |
| Tagg (° C.) | 74 | 74 |

8.5.3 Size Exclusion Chromatography Profiles of Anti-TIGIT Antibodies

The size and extent of monomer formation for BA159, BA160, and an anti-TIGIT reference antibody was assessed using analytical size exclusion chromatography.

Briefly, an Agilent 1260 HPLC and a TSKGel SuperSW mAb HR Column (Tosoh) were used to separate each antibody based on size and to determine whether high molecular weight, low molecular weight, and monomer species were present.

Each antibody was diluted to 1.0 mg/ml in a 10 mM Histidine pH 6, 115 mM NaCl solution and then 10 μl was injected onto a TSKGel SuperSW mAb HR Column (Tosoh) equilibrated in 50 mM sodium phosphate pH 6.7, 150 mM NaCl. 50 mM sodium phosphate pH 6.7, 150 mM NaCl was then pumped into the column at 0.8 ml/min. Molecules eluting from the column were detected using absorbance at 214 nm, and the area under the curve was used to quantify each peak. Data quality was verified by using visual inspection.

As shown in FIGS. 9A, 9B, and 9C, 99% of BA159, BA160, and the anti-TIGIT reference antibody, respectively, eluted at the retention times of a monomer (i.e., 10.8 minutes for BA159 and BA160, and 10.4 minutes for the anti-TIGIT reference antibody).

8.5.4 Dynamic Light Scattering Profiles of Anti-Human TIGIT Antibodies

The presence of high molecular weight species was assessed using dynamic light scattering.

Briefly, an Uncle protein stability platform from Unchained Labs was used to measure the size of particles in a sample of BA159, BA160, and an anti-TIGIT reference antibody.

Each antibody was diluted to 1 mg/ml in 1×PBS pH 7.4 (11.9 mM $PO_4$, 137 mM NaCl, 2.7 KCl). Samples were then spun at 13,000 rpm for 10 minutes to remove any dust particles or very large aggregates. 9.0 μl of diluted antibody was loaded in duplicate into a Uni, and run in the Uncle using the DLS "Sizing and Polydispersity" protocol. Scattering of light by particles moving through the sample by Brownian motion was detected at 90° to the light source. A diffusion coefficient was calculated by fitting the autocorrelation function to a single exponential, then the Stokes-Einstein equation and the diffusion coefficient were used to calculate the average hydrodynamic diameter of a hypothetical sphere of the sample. The Polydispersity Index (PDI), a measure of sample monodispersity, was also calculated. Samples with PDIs below 0.25 were considered monodisperse. All calculations were performed using the Uncle software. Data quality was verified using visual inspection.

As shown in FIGS. 10A-10C, each sample had a hydrodynamic diameter of 10 nm, the approximate size of a monomeric antibody. Each antibody also had 100% of the sample in the main monomer peak. In duplicate experiments, the PDIs were 0.189 and 0.151 for BA159, 0.198 and 0.233 for BA160, and 0.247 and 0.030 for the anti-TIGIT reference antibody.

8.5.5 Hydrophobic Interaction Chromatography Profiles of Anti-Human TIGIT Antibodies The hydrophobicity of BA159, BA160, and an anti-TIGIT reference antibody was assessed using hydrophobic interaction chromatography.

Briefly, an Agilent 1260 HPLC and a TSKGel Butyl-NPR Column (Tosoh) were used to separate each antibody based on the surface hydrophobicity of each molecule.

Each antibody was diluted to 1.0 mg/ml in a 10 mM Histidine pH 6, 115 mM NaCl solution and then 10 μl injected onto a TSKGel Butyl-NPR Column (Tosoh) equilibrated in 25 mM sodium phosphate pH 7.0, 1.5 M $(NH_4)_2SO_4$. A gradient elution was run at 1 ml/min into 25 mM sodium phosphate pH 7.0 over 21 minutes. Molecules eluting from the column were detected using absorbance at 229 nm. Data quality was verified using visual inspection.

As shown in FIGS. 11A-11C, BA159, BA160, and the anti-TIGIT reference antibody eluted at a similar ionic strength (i.e., at 10.8 min, 10.9 min, and 11.3 min, respectively), indicating that all antibodies have a comparable hydrophobicity.

8.5.6 Anti-Human TIGIT Antibodies Resistance to Stress Conditions

The resistance of BA159, BA160, and an anti-TIGIT reference antibody to interchain disulphide bond breakage, clipping, and aggregation under high temperature hold and repeated freeze-thaw cycles was tested.

Briefly, each antibody was subjected to 28 days at 40° C. or 5 freeze-thaw cycles, and a control sample was held at −80° C. Each sample was then analyzed by non-reducing CE SDS, reducing CE SDS, and size exclusion chromatography.

Each antibody was diluted to 1 mg/ml in 1×PBS pH 7.4 (11.9 mM $PO_4$, 137 mM NaCl, 2.7 KCl) and split into three 200 μl aliquots. One aliquot was stored at −80° C. as a control, one was stored at 40° C. for 28 days, and one was subjected to 5 cycles of freezing to −80° C. and thawing to room temperature. Size exclusion chromatography was performed as described in Example 5. CE SDS was performed as described in Example 4 except that 1) two samples were diluted to 0.1 mg/ml in Protein Express Sample Buffer, one sample as described above and one sample with 1:10 volume of 0.4 M DTT added to the Protein Express Sample Buffer before dilution, and 2) all samples (reduced and non-reduced) were heated at 80° C. for 5 minutes.

FIGS. 12A-12I, 13A-13I, and 14A-14I, and Tables 7-13, show changes to interchain disulphide bond breakage, clipping, and aggregation for BA159, BA160, and the anti- TIGIT reference antibody following high temperature hold conditions and repeated freeze-thaw cycles. Only small changes were observed under high temperature hold conditions and these were similar for BA159, BA160, and the anti-TIGIT reference antibody. No changes were observed for any of the molecules following repeated freeze-thaw cycles.

TABLE 7

Interchain disulphide bonding in BA159
molecules under stress conditions.

| Chains linked by disulphide bonds | Approx. Size (kDa) | BA159 Control | BA159 40 degrees/ 28 days | BA159 5x Freeze-thaw |
|---|---|---|---|---|
| Unknown | 255 | 0% | 0% | 0% |
| LHHL | 179 | 94% | 86% | 93% |
| Unknown | 170 | 0% | 4% | 1% |
| HHL | 158 | 2% | 3% | 2% |
| HH | 128 | 3% | 2% | 3% |
| HL | 99 | 0% | 1% | 0% |
| H | 65 | 0% | 2% | 0% |
| L | 39 | 0% | 1% | 1% |

TABLE 8

Interchain disulphide bonding in BA160
molecules under stress conditions.

| Chains linked by disulphide bonds | Approx. Size (kDa) | BA160 Control | BA160 40 degrees/ 28 days | BA160 5x Freeze-thaw |
|---|---|---|---|---|
| Unknown | 255 | 0% | 0% | 2% |
| LHHL | 179 | 98% | 92% | 95% |
| Unknown | 170 | 0% | 5% | 0% |
| HHL | 158 | 1% | 2% | 1% |
| HH | 128 | 0% | 0% | 0% |
| HL | 99 | 0% | 0% | 0% |
| H | 65 | 0% | 0% | 0% |
| L | 39 | 0% | 0% | 0% |

TABLE 9

Interchain disulphide bonding in the anti-TIGIT reference
antibody molecules under stress conditions.

| Chains linked by disulphide bonds | Approx. Size (kDa) | anti-TIGIT reference antibody Control | anti-TIGIT reference antibody 40 degrees/ 28 days | anti-TIGIT reference antibody 5x Freeze-thaw |
|---|---|---|---|---|
| LHHL | 166 | 89% | 79% | 88% |
| Unknown | 158 | 1% | 7% | 1% |
| HHL | 142 | 3% | 6% | 4% |
| HH | 115 | 1% | 4% | 4% |
| HL | 85 | 4% | 1% | 1% |
| H | 61 | 1% | 2% | 1% |
| L | 36 | 1% | 1% | 1% |

TABLE 10

Full-length BA159 heavy and light chains
present under stress conditions.

| Chains linked by disulphide bonds | Approx. Size (kDa) | BA159 Control | BA159 40 degrees/ 28 days | BA159 5x Freeze-thaw |
|---|---|---|---|---|
| HL | 102 | 0% | 5% | 0% |
| H | 63 | 75% | 70% | 75% |
| Unknown | 50 | 0% | 0% | 0% |
| L | 38 | 25% | 24% | 25% |

TABLE 11

Full-length BA160 heavy and light chains
present under stress conditions.

| Chains linked by disulphide bonds | Approx. Size (kDa) | BA160 Control | BA160 40 degrees/ 28 days | BA160 5x Freeze-thaw |
|---|---|---|---|---|
| HL | 102 | 0% | 1% | 0% |
| H | 63 | 75% | 72% | 75% |
| Unknown | 50 | 0% | 1% | 0% |
| L | 38 | 25% | 25% | 25% |

TABLE 12

Full-length anti-TIGIT reference antibody heavy
and light chains present under stress conditions.

| Chains linked by disulphide bonds | Approx. Size (kDa) | anti-TIGIT reference antibody Control | anti-TIGIT reference antibody 40 degrees/ 28 days | anti-TIGIT reference antibody 5x Freeze-thaw |
|---|---|---|---|---|
| HL | 103 | 1% | 8% | 1% |
| H | 102 | 73% | 66% | 72% |
| Unknown | 104 | 0% | 1% | 0% |
| L | 109 | 26% | 25% | 27% |

TABLE 13

BA159, BA160, and anti-TIGIT reference antibody
species present under stress conditions.

| | % High molecular weight | % Monomer | % Low molecular weight |
|---|---|---|---|
| BA159 Control | 1.2 | 98.8 | 0 |
| BA159 high temperature hold | 3.4 | 94.9 | 1.7 |
| BA159 5x freeze-thaw | 1.1 | 98.9 | 0 |
| BA160 Control | 1.6 | 98.3 | 0 |
| BA160 high temperature hold | 3.4 | 94.9 | 1.7 |
| BA160 5x freeze-thaw | 1.3 | 98.7 | 0 |
| anti-TIGIT reference antibody Control | 3.6 | 96.4 | 0 |
| anti-TIGIT reference antibody high temperature hold | 3.8 | 93.7 | 2.6 |
| anti-TIGIT reference antibody 5x freeze-thaw | 1.8 | 98.2 | 0 |

8.6 Example 6: Binding of BA159 to Activated Human T Cells

The ability of BA159 to bind to activated human T cells was tested and compared to the binding of an isotype control antibody.

To generate activated T cells, a frozen aliquot of healthy donor human PBMC was retrieved from liquid nitrogen and immediately thawed in 37° C. water until floating ice was observed. Cells were then transferred to 10 mL of pre-warmed R10 media. 20 µL was removed and added to 380 µL of viability dye. Cells were counted and viability was checked using a Muse apparatus. Samples were then centrifuged at 1200 rpm for five minutes and suspended to a final concentration of $1 \times 10^6$ cells/mL with R10 media. Cells were stimulated with 1 µg/ml of anti-CD3 and 100 µL of stimulated cells were pipetted into each well of a 96-well round-bottom tissue culture plate. Plates were incubated at 37° C. in 5% $CO_2$ for four days.

After four days, the sample plates were centrifuged for two minutes at 2000 rpm and then supernatants were discarded. Samples were blocked with FcγR Block prepared in FACs buffer at 5 µL per 100 µL for 10 minutes. Sample plates were then centrifuged for two minutes at 2000 rpm and the supernatant was discarded. The cells were then resuspended in 100 µL of BA159 or a relevant isotype control antibody. To prepare antibodies, each antibody was diluted to 40 µg/mL in buffer for a final volume of 200 µL. Antibodies were then serially diluted 1 to 4 for a total of 12 dilutions ranging from 40 µg/mL to 0.00000954 µg/mL.

Sample plates were incubated for 30 minutes at 4° C. Cells were washed by addition of cold sample buffer, centrifuged for two minutes at 2000 rpm, and the supernatant was discarded. This wash was repeated once.

Cells were then resuspended in a cocktail of fluorescently labeled antibodies prepared in FACs buffer. 100 µL of antibody was add per well of a round-bottom 96-well plate. The sample plate was incubated for 20 minutes on ice. Cells were then washed by addition of cold sample buffer, centrifuged for two minutes at 2000 rpm, and supernatants were discarded. This wash was repeated once. A final cocktail of PE-labeled secondary anti-human IgG antibody was prepared in 11 mL of FACs buffer. 100 µL of secondary antibody was added per well to a round-bottom 96-well plate. The sample plate was then incubated for 5 minutes on ice. Cells were washed by addition of cold sample buffer, centrifuged for two minutes at 2000 rpm, and the supernatants were discarded. This wash was repeated once.

Antibody binding was measured by flow cytometry using a BD LSR Fortessa Flow Cytometer. Unstained control cells were used to gate on the lymphocyte population using a plot of forward scatter-area (FSC-A) versus side scatter area (SSC-A) and another plot of FSC-A versus FSC-Height (FSC-H) for selection of single cells. Tubes of cells stained with each individual antibody were used to calculate compensation of the various colors used in the experiment. 100,000 events were recorded for each sample. Samples were analyzed by sequentially gating on the following populations: FSC-A vs SSC-A, FSC-H vs FSC-A, SSC-A vs LIVE/DEAD, and CD4 vs CD8 Mean fluorescence intensity (MFI) was calculated.

As shown in FIGS. 15A and 15B, BA159 bound to activated CD4+ T cells (FIG. 15A) and activated CD8+ T cells (FIG. 15B) in a dose dependent manner.

8.7 Example 7: Blocking of TIGIT/PVR Binding by BA159 and BA160

8.7.1 Blocking of TIGIT/PVR Binding by Anti-TIGIT Antibody BA159

In this example, the capacity of BA159 to block TIGIT/CD155 inhibitory signaling was analyzed and compared to blocking by an isotype control antibody.

The reporter assay was performed according to the manufacturer's protocol (Promega). Jurkat effector T cells engineered to express human TIGIT with a luciferase reporter were used. The luciferase reporter is driven by a native promoter that can respond to both TCR activation and CD226 co-stimulation. Cells were retrieved from liquid nitrogen and immediately thawed in 37° C. water until floating ice was observed. Cells were then transferred to 12 mL of pre-warmed (37° C.) assay buffer (90% RPMI 1640/10% FBS) in a conical tube. The cell suspension was gently mixed, transferred to a sterile reservoir, and 80 µL of cell suspension transferred to the inner 60 wells of a 96-well, white, flat-bottom assay plate. 120 µl of prewarmed (37° C.) assay buffer was added to each of the outside wells of the assay plates. Cells were then incubated for 16-20 hours at 37° C. in 5% $CO_2$.

A dose range of each antibody was prepared from a 6× concentrated intermediate stock in 1.2 mL bullet tubes. First, a 50 µg/mL intermediate stock was prepared in assay buffer and then antibodies were serially diluted 1 to 2.5. A total of 10 dilutions ranging from 50 µg/mL to 0.0131 µg/mL were prepared in assay buffer. 20 µL of diluted antibody was added per well to the pre-plated TIGIT effector cells.

CHO-K1 cells engineered to express human CD155 with an engineered cell-surface protein (CD155 aAPC/CHO-K1 cells) were used. The cell surface protein activates the TCR complex in an antigen-independent manner. Cells were retrieved from liquid nitrogen and immediately thawed in 37° C. water until floating ice was observed. Cells were then transferred to a 15 ml conical tube containing 3 ml of assay buffer. The cell suspension was gently mixed, transferred to a sterile reservoir, and then 20 µL of cell suspension was transferred to the pre-plated TIGIT effector cells and antibody mixture. The final assay volume was 120 µL.

Cells were then incubated for 6 hours at 37° C. in 5% $CO_2$. After incubation, assay plates were removed from the incubator and allowed to equilibrate to ambient temperature for 10 minutes. 120 µL of Bio-Glo™ reagent was then added to each well and the plates were incubated for 5 minutes at room temperature. Relative light units (RLU) were measured using a luminescence EnVision Plate Reader. Results were plotted in GraphPad Prism and curves were fit using non-linear regression.

As shown in FIGS. 16A and 16B, BA159 elicited a dose dependent increase in luciferase production, a surrogate for TCR activation and CD226 pathway activation, as measured by relative light units (RLUs). FIG. 16A and FIG. 16B represent independent experiments performed on two different days.

8.7.2 Blocking of TIGIT/PVR Binding by Anti-TIGIT Antibodies BA159 and BA160

In this example, the capacity of BA159, BA160, and an isotype control antibody to block TIGIT/CD155 inhibitory signaling was analyzed.

The assay was performed according to the manufacturer's protocol (Promega). Jurkat effector T cells engineered to express human TIGIT with a luciferase reporter were used. The luciferase reporter is driven by a native promoter that can respond to both TCR activation and CD226 co-stimulation. Cells were retrieved from liquid nitrogen and immediately thawed in 37° C. water until floating ice was observed. Cells were then transferred to 12 mL of pre-warmed (37° C.) assay buffer (90% RPMI 1640/10% FBS) in a conical tube. The cell suspension was gently mixed, transferred to a sterile reservoir, and 80 µL of cell suspension was transferred to the inner 60 wells of a 96-well, white, flat-bottom assay plate. 120 µL of prewarmed (37° C.) assay buffer was added to each of the outside wells of the assay plates. Cells were then incubated for 16-20 hours in at 37° C. in 5% $CO_2$.

A dose range of each antibody was prepared at 6× concentrated intermediate stock in 1.2 mL bullet tubes. First, a 50 µg/mL intermediate stock was prepared in assay buffer and antibodies were serially diluted 1 to 2.5 by serial dilution. A total of 10 dilutions ranging from 50 µg/mL to 0.0131 µg/mL were prepared in assay buffer. 20 µL of antibody was added per well to the pre-plated TIGIT effector cells.

CHO-K1 cells engineered to express human CD155 with an engineered cell-surface protein (CD155 aAPC/CHO-K1 cells) were used. The cell-surface protein activates the TCR complex in an antigen-independent manner. Cells were retrieved from liquid nitrogen and immediately thawed in 37° C. water until floating ice was observed. Cells were then transferred to a 15 ml conical tube containing 3 ml of assay buffer. The cell suspension was gently mixed, transferred to a sterile reservoir, and 20 µL of cell suspension was transferred to the pre-plated TIGIT effector cells and antibody mixture. The final assay volume was 120 µL.

Cells were then incubated for 6 hours at 37° C. in 5% $CO_2$. After incubation, assay plates were removed from the incubator and allowed to equilibrate to ambient temperature for 10 minutes. 120 µL of Bio-Glo™ reagent was then added to each well and the plates were incubated for 5 minutes at room temperature. Relative light units (RLU) were measured using a luminescence EnVision Plate Reader. Results were plotted in GraphPad Prism and curves were fit using non-linear regression.

FIG. 17 shows that both BA159 and BA160 blocked binding between TIGIT and PVR in a dose dependent manner.

8.8 Example 8: Stimulation of IL-2 Production by BA159, BA260, BA261, BA262, and BA160

8.8.1 Stimulation of IL-2 Production by Anti-TIGIT Antibodies BA159, BA260, BA261, and BA262

This example shows the ability of anti-TIGIT antibodies BA159, BA260, BA261, and BA262, and an IgG₁ isotype control antibody to stimulate IL-2 production in SEA-stimulated PBMCs.

Each antibody was prepared at a 5× concentration of 50 µg/mL (final concentration of 10 µg/mL) in R10 media. 20 µL of each anti-TIGIT antibody or isotype control antibody was added to the corresponding wells of a 96-well round bottom plate.

Frozen aliquots of human PBMC from three independent healthy donors were retrieved from liquid nitrogen and immediately thawed in 37° C. water until floating ice was observed. Cells were transferred to 10 mL of pre-warmed R10 media and immediately centrifuged at 1200 rpm for five minutes. To count cells and check viability, 20 µL of sample was removed and added to 380 of viability dye, mixed, and read using a Muse apparatus. Cells were then centrifuged at 1200 rpm for five minutes and resuspended in R10 media.

An intermediate stock concentration of SEA was made by adding 10 µL of 10 µg/mL SEA to 90 µL R10 to make an intermediate concentration of 1 µg/mL. Cells were first stimulated with SEA peptide and 80 µL cells and SEA mixture were added into corresponding wells with antibodies and incubated in a tissue culture incubator at 37° C. in 5% $CO_2$ within a humidified chamber for four days. A total of 100,000 cells/well and a final concentration of 1 ng/mL of SEA were used.

After four days of incubation, plates were removed from the incubator. The plates were then centrifuged for two minutes at 2000 rpm. 5 µL of supernatant was transferred to a 384-well AlphaLISA plate for cytokine analysis. AlphaLISA kits (Perkin Elmer) were used for measurement of IL-2 secretion. Briefly, assay buffer was prepared by adding 2.5 mL of 10× AlphaLISA Immunoassay Buffer to 22.5 mL water. Human IL-2 analyte was used to prepare a standard dilution. A mixture of 1.6× AlphaLISA anti-IL-2 acceptor beads and biotinylated anti-IL-2 antibody was prepared in assay buffer. 8 µL was added to each well and incubated in darkness at room temperature. AlphaLISA plates were briefly centrifuged at 2000 rpm. A 2.3× Streptavidin Donor Bead intermediate stock was prepared in assay buffer. Then 10 µL was added to each well and incubated in darkness at room temperature. AlphaLISA plates were briefly centrifuged at 2000 rpm. Relative light units (RLU) were then measured using the AlphaScreen protocol on an EnVision Plate Reader. Results were plotted in GraphPad Prism and statistical analyses were performed using an unpaired t-test.

As shown in FIGS. 18A-18C, BA159, BA260, BA261, and BA262 stimulated IL-2 production.

8.8.2 Stimulation of IL-2 Production by a Combination of Anti-TIGIT Antibodies BA159, BA260, BA261, and BA262 and an Anti-PD-1 Antibody This example shows the ability of anti-TIGIT antibodies BA159, BA260, BA261, and BA262, and an IgG₁ isotype control antibody to stimulate IL-2 production in SEA-stimulated PBMCs in the presence or absence of an anti-PD-1 antibody.

Each antibody was prepared at a 5× concentration of 50 µg/mL (final concentration of 10 µg/mL) in R10 media. For combinations, anti-TIGIT or isotype control antibodies were mixed with an equal concentration of an anti-PD-1 antibody (nivolumab) at a 5× concentration of 50 µg/mL (final concentration of 10 µg/mL) in R10 media. 20 µL of each anti-TIGIT antibody or isotype control antibody was added to the corresponding wells of a 96-well round bottom plate. For combinations with anti-PD-1 antibody, 20 µl anti-PD-1 antibody was also added to the well.

Frozen aliquots of human PBMC from two independent healthy donors were retrieved from liquid nitrogen and immediately thawed in 37° C. water until floating ice was observed. Cells were transferred to 10 mL of pre-warmed R10 media and immediately centrifuged at 1200 rpm for five minutes. To count cells and check viability, 20 µL of sample was removed and added to 380 of viability dye, mixed, and read using a Muse apparatus. Cells were then centrifuged at 1200 rpm for five minutes and resuspended in R10 media.

An intermediate stock concentration of SEA was made by adding 10 µL of 10 µg/mL SEA to 90 µL R10 to make an intermediate concentration of 1 µg/mL. Cells were first stimulated with SEA peptide and 80 µL cells and SEA mixture were added into corresponding wells with antibodies and incubated in a tissue culture incubator at 37° C. in 5% $CO_2$ within a humidified chamber for four days. A total of 100,000 cells/well and final concentration of 1 ng/mL of SEA was used.

After four days of incubation, plates were removed from the incubator. The plates were then centrifuged for two minutes at 2000 rpm. 5 µL of supernatant was transferred to a 384-well AlphaLISA plate for cytokine analysis. AlphaLISA kits (Perkin Elmer) were used for measurement of IL-2 secretion. Briefly, assay buffer was prepared by adding 2.5 mL of 10× AlphaLISA Immunoassay Buffer to 22.5 mL water. Human IL-2 analyte was used to prepare a standard dilution. A mixture of 1.6× AlphaLISA anti-IL-2 acceptor beads and biotinylated anti-IL-2 antibody was prepared in assay buffer. 8 μL was added to each well and incubated in darkness at room temperature. AlphaLISA plates were briefly centrifuged at 2000 rpm. A 2.3× Streptavidin Donor Bead intermediate stock was prepared in assay buffer. Then 10 μL was added to each well and incubated in darkness at room temperature. AlphaLISA plates were briefly centrifuged at 2000 rpm. Relative light units (RLU) were then measured using the AlphaScreen protocol on an EnVision Plate Reader. Results were plotted in GraphPad Prism and statistical analyses were performed using an unpaired t-test.

As shown in FIGS. 19A and 19B, BA159, BA260, BA261, and BA262 stimulated IL-2 production. This effect was enhanced when cells were treated with both an anti-TIGIT antibody and an anti-PD-1 antibody.

8.8.3 Stimulation of IL-2 Production by BA159 and BA160

In this example, the ability of BA159, BA160, and an isotype control antibody to promote IL-2 secretion by SEA-stimulated PBMCs was demonstrated over a range of antibody concentrations in two different donors.

A dose range of each anti-TIGIT antibody, or a relevant isotype control antibody, were prepared at 5× concentrated intermediate stock in 1.2 mL bullet tubes. First, a 50 μg/mL intermediate stock was prepared in R10 media and antibodies were serially diluted 1 to 10 by serial dilution. A total of 8 dilutions ranging from 50 μg/mL to 0.000005 μg/mL were prepared in R10 media. 20 μL of antibody was added per well to a round-bottom 96-well plate.

Frozen aliquots of human PBMCs from two healthy donors were retrieved from liquid nitrogen and immediately thawed in 37° C. water until floating ice was observed. Cells were transferred to 10 mL of pre-warmed R10 media and immediately centrifuged at 1500 rpm for five minutes. The supernatant was discarded and cells were resuspended in fresh R10 media. To count cells and check viability, 20 μL of sample was removed and added to 380 μL of viability dye, mixed, and read using a Muse apparatus.

Cells were resuspended to an intermediate concentration. An intermediate stock concentration of SEA was made by adding 10 μL of 10 μg/mL SEA to 90 μL R10 to make an intermediate concentration of 1 μg/mL. Cells were first stimulated with SEA peptide and 80 μL cells and SEA mixture were added into corresponding wells and incubated in tissue culture incubator at 37° C. in 5% $CO_2$ within a humidified chamber for four days. A total of 100,000 cells/well and final concentration of 1 ng/mL of SEA was used.

After four days of incubation, plates were removed from the incubator. The plates were then centrifuged for two minutes at 2000 rpm. 5 μL of supernatant was transferred to a 384-well AlphaLISA plate for cytokine analysis. AlphaLISA kits (Perkin Elmer) were used for measurement of IL-2 secretion. Briefly, assay buffer was prepared by adding 2.5 mL of 10× AlphaLISA Immunoassay Buffer to 22.5 mL water. Human IL-2 analyte was used to prepare a standard dilution. A mixture of 1.6× AlphaLISA anti-IL-2 acceptor beads and biotinylated anti-IL-2 antibody was prepared in assay buffer. 8 μL was added to each well and incubated in darkness at room temperature. AlphaLISA plates were briefly centrifuged at 2000 rpm. A 2.3× Streptavidin Donor Bead intermediate stock was prepared in assay buffer. Then 10 μL was added to each well and incubated in darkness at room temperature. AlphaLISA plates were briefly centrifuged at 2000 rpm. Relative light units (RLU) were then measured using the AlphaScreen protocol on an EnVision Plate Reader. Results were plotted in GraphPad Prism and curves were fit using non-linear regression.

As shown in FIGS. 20A and 20B, both BA159 and BA160 promoted IL-2 secretion by SEA-stimulated PBMCs in a dose dependent manner in two different donors.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed:

1. An isolated antibody that specifically binds to human TIGIT, the antibody comprising a VH comprising the amino acid sequence of SEQ ID NO: 7 or 8, and a VL comprising the amino acid sequence of SEQ ID NO: 9 or 10.

2. The isolated antibody of claim 1, wherein the antibody comprises the VH and VL amino acid sequences of SEQ ID NOs: 7 and 9.

3. The isolated antibody of claim 1, wherein the antibody comprises a heavy chain constant region selected from the group consisting of human IgG$_1$, IgG$_2$, IgG$_3$, IgG$_4$, IgA$_1$, and IgA$_2$.

4. The isolated antibody of claim 3, wherein the antibody comprises an IgG$_1$ heavy chain constant region, wherein:
   (a) the IgG$_1$ heavy chain constant region comprises the amino acid sequence of SEQ ID NO: 16;
   (b) the amino acid sequence of the IgG$_1$ heavy chain constant region comprises an N297A mutation, numbered according to the EU numbering system;
   (c) the amino acid sequence of the IgG$_1$ heavy chain constant region comprises S267E and L328F mutations, numbered according to the EU numbering system;
   (d) the amino acid sequence of the IgG$_1$ heavy chain constant region comprises at least one mutation selected from the group consisting of S239D, A330L, and I332E mutations, numbered according to the EU numbering system; or
   (e) the amino acid sequence of the IgG$_1$ heavy chain constant region comprises S239D, A330L, and I332E mutations, numbered according to the EU numbering system.

5. The isolated antibody of claim 3, wherein the antibody comprises a heavy chain constant region that is a variant of a wild type heavy chain constant region, wherein the variant heavy chain constant region binds to an FcγR with higher affinity than the wild type heavy chain constant region binds to the FcγR, wherein the FcγR is FcγRIIB or FcγRIIIA.

6. The isolated antibody of claim 1, wherein the antibody comprises a heavy chain comprising the amino acid sequence of SEQ ID NO: 11, 12, 19, or 20, and/or a light chain comprising the amino acid sequence of SEQ ID NO: 13, 14, 15, or 21.

7. The isolated antibody of claim 1, wherein the antibody comprises a light chain constant region comprising the amino acid sequence of SEQ ID NO: 17 or 18.

8. The isolated antibody of claim 1, wherein:
   (a) the antibody is multispecific;
   (b) the antibody is conjugated to a cytotoxic agent, cytostatic agent, toxin, radionuclide, or detectable label; or
   (c) the antibody is conjugated to an antibody.

9. The isolated antibody of claim 1, wherein the antibody comprises the VH and VL amino acid sequences of SEQ ID NOs: 7 and 10, respectively.

10. A composition comprising the isolated antibody of claim 1 and a pharmaceutically acceptable carrier or excipient.

11. The isolated antibody of claim 1, wherein the antibody comprises the VH and VL amino acid sequences of SEQ ID NOs: 8 and 9.

12. The isolated antibody of claim 1, wherein the antibody comprises the VH and VL amino acid sequences of SEQ ID NOs: 8 and 10.

13. The isolated antibody of claim 1, wherein the antibody has a thermal melting temperature of about 77° to 80° C.

14. An isolated antibody that specifically binds to human TIGIT, wherein the antibody comprises a heavy chain comprising the amino acid sequence of SEQ ID NO: 11, 12, 19, or 20, and a light chain comprising the amino acid sequence of SEQ ID NO: 13, 14, 15, or 21.

15. The isolated antibody of claim 14, wherein the heavy chain and light chain comprise the amino acid sequences of SEQ ID NOs: 11 and 13; 11 and 14; 11 and 15; 11 and 21; 12 and 13; 12 and 14; 12 and 15; 12 and 21; 19 and 13; 19 and 14; 19 and 15; 19 and 21; 20 and 13; 20 and 14; 20 and 15; or 20 and 21, respectively.

16. The isolated antibody of claim 15, wherein the heavy chain and light chain comprise the amino acid sequences of SEQ ID NOs: 11 and 13, or 19 and 13, respectively.

17. A composition comprising the isolated antibody of claim 14 and a pharmaceutically acceptable carrier or excipient.

18. The isolated antibody of claim 14, wherein the antibody has a thermal melting temperature of about 77° to 80° C.

* * * * *